(12) United States Patent
Blade et al.

(10) Patent No.: US 8,198,441 B2
(45) Date of Patent: Jun. 12, 2012

(54) PROCESS FOR THE PREPARATION OF NOVEL PYRIDOPYRAZINES AS MTOR KINASE INHIBITORS

(75) Inventors: Helen Blade, Macclesfield (GB); Gwydion Huw Churchill, Macclesfield (GB); Angela Charlotte Currie, Macclesfield (GB); Benjamin Charles Dobson, Macclesfield (GB); Martin Neal Kenworthy, Macclesfield (GB); Lyn Powell, Macclesfield (GB); Steven Anthony Raw, Macclesfield (GB); Peter Samuel Hynes, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 236 days.

(21) Appl. No.: 12/487,294

(22) Filed: Jun. 18, 2009

(65) Prior Publication Data

US 2009/0318434 A1 Dec. 24, 2009

Related U.S. Application Data

(60) Provisional application No. 61/074,188, filed on Jun. 20, 2008, provisional application No. 61/152,350, filed on Feb. 13, 2009.

(51) Int. Cl.
C07D 471/02 (2006.01)

(52) U.S. Cl. ........................................ 544/279

(58) Field of Classification Search .................. 544/279
See application file for complete search history.

(56) References Cited

U.S. PATENT DOCUMENTS

| | | | |
|---|---|---|---|
| 4,560,685 | A | 12/1985 | Roch et al. |
| 5,990,117 | A | 11/1999 | Pamukcu et al. |
| 2003/0187026 | A1 | 10/2003 | Li et al. |

FOREIGN PATENT DOCUMENTS

| | | |
|---|---|---|
| EP | 0185259 A2 | 6/1986 |
| EP | 1277738 A1 | 1/2003 |
| WO | 0117972 A2 | 3/2001 |
| WO | 2004052890 A1 | 6/2004 |
| WO | 2004099159 A1 | 11/2004 |
| WO | 2006069805 A2 | 7/2006 |
| WO | 2006135993 A1 | 12/2006 |
| WO | 2007060404 A1 | 5/2007 |
| WO | 2008023161 A1 | 2/2008 |
| WO | 2009050506 A1 | 4/2009 |

OTHER PUBLICATIONS

Sarbassov et al, Rictor, a Novel Binding Partner of mTor, Defines a Rapamycin-Insensitive and Raptor-Independent Pathway that regulates the Cytoskeleton. Current Biology, 2004,pp. 1296-1302, vol. 14.
Choo & Blenis, 'TORgeting oncogene addiction for cancer therapy', Cancer Cell, 2006, pp. 77-79, vol. 9.
Thomas et al, 'Hypoxia-inducible factor determines sensitivity to inhibitors of mTOR in kidney cancer'. Nature Medicine, 2006, pp. 122-127, vol. 12.
Hay, 'The Akt-mTOR tango and its relevance to cancer', Cancer Cell, 2005, pp. 179-183, vol. 8.
Bernadi et al, 'PML inhibits HIF-1 alpha translation and neoangiogensesis through repression of Mtor' Nature, 2006, pp. 779-785, vol. 442.
Easton and Houghton, 'Therapeutic potential of target of rapamycin inhibitors', Expert Opinion on Therapeutic Targets, 2004, pp. 551-564, 2004, vol. 8.
Sehgal, 'Sirolimus, its discovery, biological properties, and mechanism of action', Transplantation Proceedings, 2003, pp. 7S-14S, vol. 35(3).
Morice et al, 'A Randomised Comparison of a Sirolimus-eluting stent with a standard stent for coronary revascularisation', New England Journal of Medicine, 2002, pp. 1773-1780, vol. 346.
Eisen et al, 'Everolimus for the Prevention of Allograft Rejection and Vasculopathy in Cardiac-Transplant Recipients', New England Journal of Medicine, 2003, pp. 847-858, vol. 349.
Tee & Blenis, 'mTOR, Translational control and human disease', Seminars in Cell and Developmental Biology, pp. 29-37, 2005, vol. 16 (1).
Brown et al, 'A mammalian protein targeted by G1-arresting rapamycin-receptor complex', Nature,1994, pp. 756-758, vol. 369.
Chiu et al, 'RAPTI, a mammalian homolog of yeast Tor, interacts with the FKBP12/rapamycin complex', Proceedings of the National Academy of Sciences of the United States of America, 1994, pp. 12574-12578, vol. 91(26).
Sabatini, et al, RAFT1: A Mammalian Protein That Binds to FKBP12 in a Rapamycin-Dependent Fashion and Is Homologous to Yeast TORs, Cell, 1994, pp. 35-43, vol. 78.
Sabers et al, 'Isolation of a Protein Target of the FKBP12-Rapamycin Complex in Mammalian Cells', The Journal of Biological Chemistry, 1995, pp. 815-822 , vol. 270(2).
Abraham, 'Phosphatidylinositol 3-kinase related kinases', Current Opinions in Immunology, 1996, pp. 412-418, vol. 8.

(Continued)

Primary Examiner — James O Wilson
Assistant Examiner — Brian McDowell
(74) Attorney, Agent, or Firm — AstraZeneca AB; Julie Anne Knight

(57) ABSTRACT

There is provided a process for the preparation of a compound of Formula 1,

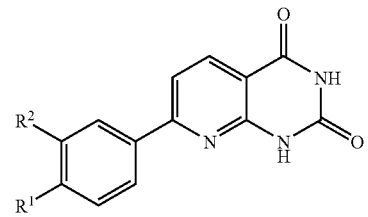

the use of said process in the preparation of a compound of Formula 5

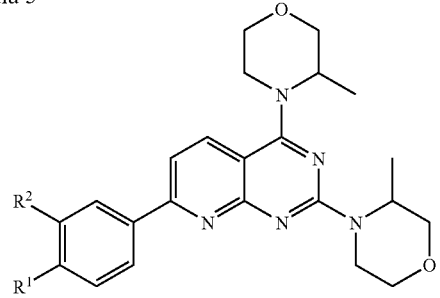

or a phosphate, sulphate, hydrogensulphate, malate, citrate, tartrate or fumarate salt thereof, and the use of the fumarate salt in a composition for use in therapy.

3 Claims, 8 Drawing Sheets

OTHER PUBLICATIONS

Schmelze & ,Hall, 'TOR, a Central Controller of Cell Growth', Cell, 2000, pp. 253-262, vol. 103.
Burnett et al, 'RAFT1 phosphorylation of the translational regulators p70 S6 kinase and 4E-BpI' Proceedings of the National Academy of Sciences of the United States of America, 1998, pp. 1432-1437, vol. 95 (4).
Terada et al, 'Rapamycin selectively inhibits translation of mRNAs encoding elongation factors and ribosomal proteins', Proceedings of the National Academy of Sciences of the United States of America, 1994, pp. 11477-11481, vol. 91(24).
Jeffries et al, 'Rapamycin suppresses 5' TOP mRNA translation through inhibition of p70 S6K', The EMBO Journal, 1997 pp. 3693-3704, vol. 16(12).
Bjornsti and Houghton, 'The Tor Pathway: A Target for Cancer Therapy', Nature Reviews Cancer, 2004, pp. 335-348, vol. 4.
Gingras et al, 'Regulation of 4E-BP1 phosphorylation: a novel two-step mechanism', Genes Development, 1999, pp. 1422-1437, vol. 13.
Gingras et al, 'Regulation of translation initiation by FRAP/mTOR', Genes Development, 2001, pp. 807-826 vol. 15.
Neuhaus et al, mTOR Inhibitors: An Overview, Liver Transplantation, 2001, pp, 473-484, vol. 7(6).
Woods & Marks, 'Drug-Eluting Stents', Annu Rev Med, 2004 pp. 169-178, 55.
Dahia, 'PTEN, a unique tumour suppressor gene', Endocrine-Related Cancer, 2000, pp. 115-129, vol. 7.
Cristofano and Pandolfi, 'The Multiple Roles of PTEN in Tumour Suppression', Cell, 2000, pp. 387-390, vol. 100.
Samuels, 'High Frequency of Mutations of the PIK3CA Gene in Human Cancers', Science, 2004, p. 554, vol. 304.
Huang et Houghton, 'Targeting mTOR signalling for cancer therapy', Current Opinion in Pharmacology, 2003, pp. 371-377, vol. 3.
Sawyers, 'Will mTor inhibitors make it as cancer drugs?', Cancer Cell, 2003, pp. 343-348, vol. 4.
Huang et Houghton, 'Inhibitors of mammalian target of rapamycin as novel antitumour agents: from bench to clinic', Current Opinion in Investigational Drugs, 2000, pp. 295-304, vol. 3 (2).
Brunn et al, 'Direct Inhibition of the signaling functions of the mammalian target of rapamycin by the phosphoinositide 3-kinase inhibitors, wortmannin and LY294002', EMBO Journal, 1996, pp. 5256-5267, vol. 15.
Edinger et al, 'Different Effects of Rapamycin on Mammalian Target of Rapmycin Signalling Functions in Mammalian Cells', Journal of Cancer Research, 2003, 8451-8460, vol. 63.
Lawrence et al, 'Modulation of the Protein Kinase Activity of mTOR', Curr Top Microbiol Immunol, 2004, pp. 199-213, vol. 279.
Eshelman et al, 'Inhibition of the Mammalian Target of Rapmycin Sensitizes U87 Xenografts to Fractionated Radiation Therapy' Cancer Research, 2002, pp. 7291-7297, vol. 62.
Berge et al, 'Pharmaceutical Salts', Journal of Pharmaceutical Sciences, 1977, pp. 1-19, vol. 66.
Griffin et al, Selective Benzopyranone and Pyrimido [2,1 - alpha]isoquinolin-4-one Inhibitors of DNA-Dependent Protein Kinase: Synthesis, Structure—Activity Studies and Radiosensitization of a Human Tumour Cell Line in Vitro, Journal of Medicinal Chemistry, 2005, pp. 569-585, vol. 48.
Nishikawa, 'Structure-Activity of the Diuretic Activity of Triaza- and Tetraaza-napthalene Compounds' , Chem Pharma Bull, 1976, pp. 2057-2077, vol. 24(9).
Hayakawa et al, 'Synthesis and biological evaluation of 4-morpholino-2-phenylquinazolines and related derivatives as novel PI3 kinase p110 alpha inhibitors'—Bioorganic and Medicinal Chemistry, 2006, pp. 6847-6858, vol. 14.
Deutsch, 'In vitro and in vivo experiences with an antiaggregating agent SH-869 SU', International Congress Series, 1974, pp. 319-323, vol. 357.
Sugimoto, 'An Improved Method for Chlorination of Nitrogen-containing pi-deficient heteroaromatics using triphenylphosphine and trichloroisocyanuric acid', Heterocycles, 2005, pp. 181-185, vol. 65(1).
Charier, 'An Efficient Fluorescent Probe for Ratiometric pH measurements in Aqueous Solutions', Angewandte Chemie, 2004, pp. 4785-4788, vol. 43.
Lellek, 'Straightforward Synthesis of Axially Chiral 1,4-Napthodiazepine Derivatives', Synlett, 2000, pp. 1616-1618, vol. 11.
JAGTAP, The discovery and synthesis of novel adenoside substituted 2,3-dihydro-1H-isoindo1-1-ones; potent inhibitors of poly(ADP-ribose) polymerase-1 (PARP-1), Bioorganic & Medicinal Chemistry Letters, 2004, pp. 81-85, vol. 14.
Stocks et al, 'Structure-driven HtL: Design and synthesis of novel aminoindazole inhibitors of c-Jun N-terminal kinase activity', Bioorganic & Medicinal Chemistry Letters, 2005, pp. 3459-3462, vol. 15.
Tanaka et al, 'Inhibitors of Acyl-CoA: Cholesterol O-Acyltransferase 2. Identification and Structure-Activity Relationships of a Novel Series of N-Alkyl-N-(heteroaryl-substituted benzyl)-N-arylureas', Journal of Medical Chemistry, 1998, pp. 2390-2410, vol. 41.
Yin et al 'Pd-Catalysed N-Arylation of Heteroarylamines', Organic Letters, 2002, pp. 3481-3484, vol. 4(20).
Junek et al, 'Beitrage zur Chemie der Enaminoketone, 4, Mitt: 1,2,3,4-Tetrahydro-pyrido [2,3-d]pyrimidin-2,4-dione',
Monatshefte Fur Chemie—Chemical Monthly, 1970, pp. 1130-1135, vol. 101(4).
Anderson , 'Regioselective Synthesis of Pyrid[2,3-d]pyrimidines', Journal of Heterocyclic Chemistry, 1985, pp. 1469-1470, vol. 22.
Kuwada et al, 'A New Synthesis of 6-substituted pyrido[2,3-d] Pyrimidines', Heterocycles, 2002, pp. 2081-2090, vol. 57(11).
Tominaga, 'Reaction of 6-Aminouracils with Keternthioacetals', Chem Pharm Bull, 1984, pp. 122-129, vol. 32(1).
Gangjee et al, Synthesis of Some 2,4-Disubstituted Tetrahydropyrimido (4,5-b)quinolines as Potential Antitumour Agents (1), Journal of Hetercyclic Chemistry, 1985, pp. 1149-1151, vol. 22.
Brinker et al, 'Pyridinderivate aus 3-Chlor-2-propeniminiumsalzen und Enaminen', Arch Pharm (Weinhem) 1987, pp. 520-527, vol. 320.
Manpadi, 'Three-component synthesis and anticancer evaluation of polycyclic indenopyridines lead to the discovery of a novel indenoheterocycle with potent apoptosis including properties', Organic & Biomolecular Chemistry, 2007, pp. 3865-3872, vol. 5.
Girreser et al, 'Synthesis of 6-substituted 7-aryl-5,6-dihydropyrido [2,3-d]pyrimidine (1H,3H)-2,4-diones using the Vilsmeier reaction', Tetrahedron, 2004, pp. 11511-11517, vol. 60.
Ryabukhin, 'Chlorotrimethylsilane-Mediated Synthesis of Functionalised Fused Pyridines: Reaction of 3-Formylchromones with Electron-Rich Aminoheterocycles', Synthesis, 2007, pp. 1861-1871, vol. 12.
Takahashi, 'Synthesis of Trifluoromethylated Pyrido [2,3-d]pyrimidine-2,4-diones from 6 Aminouracils and Trifluoromethylated Pyrazolo [3,4-b]-pyridines from 5-Aminopyrazoles', Journal of Heterocyclic Chemistry, 2004, pp. 525-530, vol. 41.
Ma et al, 'A Novel Regio- and Stereospecific Hydrohalogenation Reaction of 2-Propynoic Acid and its derivatives', Journal of Organic Chemistry, 1992, pp. 709-713, vol. 57.
Conde et al, 'A novel method for the synthesis of aromatic E-beta-chlorovinylketones', Tetrahedron Letters, 2000, pp. 4709-4711, vol. 41.
Hughes et al, One or Two-Step Bohlmann-Rahtz, Heteroannulation of 6-Aminouracil Derivatives for the Synthesis of Pyrido[2,3-d]pyrimidines, Syntlett, 2002, pp. 1332-1334, vol. 8.
R K Robins, Studies on Condensed Pyrimidine Systems. XIX. A New Synthesis of Pyrido [2,3-d} pyrimidines. The Condensation of 1,3-Diketones and 3-Ketoaldehydes with 4-Aminopyrimidines' Journal of American Chemical Society, 1958, pp. 3449-3454, vol. 80.
Troschutz et al, 'Versuche zur Synthese von pharmakologisch wirksamen Heterocyclen via Mannich-Reaktion, 3 Mitt', Arch Pharm (Weinheim), 1978, pp. 406-414, vol. 311.
Churchill et al. 'Improved Synthesis of Substituted Pyrido[2,3-d]pyrimidinediones' Tetrahedron Letters (2011); vol. 52; pp. 3657-3661.
Nishio et al. Reduction of beta-Arylthio- or beta-Alkylthio-alpha beta-Unsaturated Ketones, J C S Perkin, 1980, pp. 934-938, vol. 1.

X-Ray diffraction pattern of the D-tartrate salt after drying overnight

X-Ray diffraction pattern the fumarate salt

Form B

(powder pattern collected at 5% relative humidity)

Bioaccessibility of Formula 5a free base and fumarate salt using TIM-1 in vitro model

__US 8,198,441 B2__

PROCESS FOR THE PREPARATION OF NOVEL PYRIDOPYRAZINES AS MTOR KINASE INHIBITORS

This application claims the benefit under 35 U.S.C. §119 (e) of Application No. U.S. 61/074,188 filed on 20 Jun. 2008 and of Application No U.S. 61/152,350 filed on 13 Feb. 2009.

The present invention relates to a process and intermediates useful in the preparation of certain pyrido-pyrimidine compounds, which act as mTOR kinase inhibitors, to salt forms thereof, and their formulation, particularly in tablet form, and use thereof.

BACKGROUND

Growth factor/mitogenic activation of the phosphatidylinositol 3-kinase (PI3K)/AKT signalling pathway ultimately leads to the key cell cycle and growth control regulator mTOR, the mammalian target of rapamycin (alternatively referred to as FRAP (FKBP12 and rapamycin associated protein), RAFT1 (rapamycin and FKBP12 target 1), RAPT1 (rapamycin target 1)—all derived from the interaction with the FK-506-binding protein FKBP12, and SEP (sirolimus effector protein)). mTOR is a mammalian serine/threonine kinase of approximately 289 kDa in size and a member of the evolutionary conserved eukaryotic TOR kinases (refs. 1-4). The mTOR protein is a member of the PI3-kinase like kinase (PIKK) family of proteins due to its C-terminal homology (catalytic domain) with PI3-kinase and the other family members, e.g. DNA-PKcs (DNA dependent protein kinase), ATM (Ataxia-telangiectasia mutated). In addition to a catalytic domain in the C-terminus, mTOR contains a FKBP12/rapamycin complex binding domain (FRB). At the N-terminus up to 20 HEAT (Huntingtin, EF3, alpha regulatory subunit of PP2A and TOR) motifs are found whilst more C-terminal is a FAT (FRAP-ATM-TRRAP) domain, and at the extreme C-terminus of the protein an additional FAT domain is found (FAT-C) (refs. 5,6).

TOR has been identified as a central regulator of both cell growth (size) and proliferation, which is in part governed by translation initiation. TOR dependant phosphorylation of S6-kinase (S6K1) allows translation of ribosomal proteins involved in cell cycle progression (refs. 7-9). Cap-dependant translation is regulated by the phosphorylation of the eukaryotic translation initiation factor 4E (eIF4E)-binding protein 1 (4E-BP1 (PHAS-1)). This modification prevents PHAS-1 binding eIF4E, thereby permitting formation of an active eIF4F translation complex (reviewed in refs. 10, 11, 12). Activation of these signalling elements is dependant on insulin, other growth factors and nutrients suggesting a gatekeeper role for mTOR in the control of cell cycle progression only under favourable environmental conditions. The PI3K/AKT signalling cascade lies upstream of mTOR and this has been shown to be deregulated in certain cancers and results in growth factor independent activation in, for example, PTEN deficient cells. mTOR lies at the axis of control for this pathway and inhibitors of this kinase (e.g. sirolimus (rapamycin or Rapamune™) and everolimus (RAD001 or Certican™)) are already approved for immunosuppression and drug eluting stents (reviewed in refs. 13, 14), and are now receiving particular interest as novel agents for cancer treatment.

Tumour cell growth arises from the deregulation of normal growth control mechanisms such as the loss of tumour suppressor function(s). One such tumour suppressor is the phosphatase and tensin homologue deleted from chromosome ten (PTEN). This gene, also known as mutated in multiple advanced cancers (MMAC), has been shown to play a significant role in cell cycle arrest and is the most highly mutated tumour suppressor after p53. Up to 30% of glioblastoma, endometrial and prostate cancers have somatic mutations or deletions of this locus (refs. 15, 16).

PI3K converts phosphatidylinositol 4,5, bisphosphate (PIP2) to phosphatidylinositol 3,4,5, triphosphate (PIP3) whilst PTEN is responsible for removing the 3' phosphate from PIP3 producing PIP2. PI3-K and PTEN act to maintain an appropriate level of PIP3 which recruits and thus activates AKT (also known as PKB) and the downstream signalling cascade that is then initiated. In the absence of PTEN, there is inappropriate regulation of this cascade, AKT becomes effectively constitutively activated and cell growth is deregulated. An alternative mechanism for the deregulation of this cell signalling process is the recent identification of a mutant form of the PI3K isoform, p110alpha (ref 17). The apparent increased activity of this mutant is thought to result in increased PIP3 production, presumably in excess of that which the function of PTEN can counteract. Increased signalling from PI3K, thus results in increased signalling to mTOR and consequently, its downstream activators.

In addition to the evidence linking mTOR with cell cycle regulation (from G1 to S-phase) and that inhibition of mTOR results in inhibition of these regulatory events it has been shown that down regulation of mTOR activity results in cell growth inhibition (Reviewed in refs. 7, 18, 19). The known inhibitor of mTOR, rapamycin, potently inhibits proliferation or growth of cells derived from a range of tissue types such as smooth muscle, T-cells as well as cells derived from a diverse range of tumour types including rhabdomyosarcoma, neuroblastoma, glioblastoma and medulloblastoma, small cell lung cancer, osteosarcoma, pancreatic carcinoma and breast and prostate carcinoma (reviewed in ref 20). Rapamycin has been approved and is in clinical use as an immunosuppressant, its prevention of organ rejection being successful and with fewer side effects than previous therapies (refs. 20, 21). Inhibition of mTOR by rapamycin and its analogues (RAD001, CCI-779) is brought about by the prior interaction of the drug with the FK506 binding protein, FKBP12. Subsequently, the complex of FKBP12/rapamycin then binds to the FRB domain of mTOR and inhibits the downstream signalling from mTOR.

The potent but non-specific inhibitors of PI3K, LY294002 and wortmannin, also have been shown to inhibit the kinase function of mTOR but act through targeting the catalytic domain of the protein (ref. 21). Further to the inhibition of mTOR function by small molecules targeted to the kinase domain, it has been demonstrated that kinase dead mTOR cannot transmit the upstream activating signals to the downstream effectors of mTOR, PHAS-1 or p70S6 kinase (ref. 22). It is also shown that not all functions of mTOR are rapamycin sensitive and this may be related to the observation that rapamycin alters the substrate profile of mTOR rather than inhibiting its activity per se (ref. 23). Analysis of the interactions of mTOR with other cellular factors has revealed that in addition to the mTOR-Raptor complex, there is also an mTOR-Rictor complex representing a rapamycin insensitive activity of mTOR (B) (Sarbassov et al. *Current Biology* (2004) 14, 1296-1302). This activity likely accounts for the discrepancy between kinase dead mTOR and the alteration of mTOR signalling by rapamycin and its derivatives. The discrepancy also identifies the possibility of a therapeutic advantage in inhibiting directly the catalytic activity of mTOR. It has been suggested that a catalytic inhibitor of mTOR may be a more effective antagonist of cancer cell proliferation and survival and that rapamycin may be more useful in combination with agents that can compensate for its failure to completely disrupt pathway signalling (Choo and Blenis, *Cancer Cell*

(2006) 9, 77-79; Hay, *Cancer Cell* (2005) 8, 179-183). Therefore, it is proposed that a kinase domain directed inhibitor of mTOR may be a more effective inhibitor of mTOR.

In addition to rapamycin's ability to induce growth inhibition (cytostasis) in its own right, rapamycin and its derivatives have been shown to potentiate the cytotoxicity of a number of chemotherapies including cisplatin, camptothecin and doxorubicin (reviewed in ref. 20). Potentiation of ionising radiation induced cell killing has also been observed following inhibition of mTOR (ref. 24). Experimental and clinical evidence has shown that rapamycin analogues are showing evidence of efficacy in treating cancer, either alone or in combination with other therapies (see refs. 10, 18, 20). These findings suggest that pharmacological inhibitors of mTOR kinase should be of therapeutic value for treatment of the various forms of cancer comprising solid tumours such as carcinomas and sarcomas and the leukaemias and lymphoid malignancies. In particular, inhibitors of mTOR kinase should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

Renal cell carcinoma in particular, has been identified as sensitive to the rapamycin derivative CCI-779, resulting from a loss of VHL expression (Thomas et al. *Nature Medicine* (2006) 12, 122-127). Tumours that have lost the promyelocytic leukaemia (PML) tumour suppressor, have also been shown to be sensitive to inhibition of mTOR by rapamycin as a consequence of disruption of the regulation of the mTOR signalling pathway (Bernadi, *Nature* (2006) 442, 779-785) and the use of an mTOR kinase inhibitor in these diseases should be of therapeutic value. These latter examples in addition to those of PTEN deficiency or PI3K mutation indicate where a targeted approach to the use of mTOR inhibitors may prove particularly effective due to an underlying genetic profile, but are not considered to be exclusive targets.

Recent studies have revealed a role for mTOR kinase in other diseases (Easton & Houghton, *Expert Opinion on Therapeutic Targets* (2004) 8, 551-564). Rapamycin has been demonstrated to be a potent immunosuppressant by inhibiting antigen-induced proliferation of T cells, B cells and antibody production (Sehgal, *Transplantation Proceedings* (2003) 35, 7S-14S) and thus mTOR kinase inhibitors may also be useful immunosuppressives. Inhibition of the kinase activity of mTOR may also be useful in the prevention of restenosis, that is the control of undesired proliferation of normal cells in the vasculature in response to the introduction of stents in the treatment of vasculature disease (Morice et al., *New England Journal of Medicine* (2002) 346, 1773-1780). Furthermore, the rapamycin analogue, everolimus, can reduce the severity and incidence of cardiac allograft vasculopathy (Eisen et al., *New England Journal of Medicine* (2003) 349, 847-858). Elevated mTOR kinase activity has been associated with cardiac hypertrophy, which is of clinical importance as a major risk factor for heart failure and is a consequence of increased cellular size of cardiomyocytes (Tee & Blenis, *Seminars in Cell and Developmental Biology* (2005) 16, 29-37). Thus mTOR kinase inhibitors are expected to be of value in the prevention and treatment of a wide variety of diseases in addition to cancer.

The vast majority of mTOR pharmacology to date has focused on inhibition of mTOR via rapamycin or its analogues. However, as noted above, the only non-rapamycin agents that have been reported to inhibit mTOR's activity via a kinase domain targeted mechanism are the small molecule LY294002 and the natural product wortmannin (ref. 21).

Certain mTOR inhibitors have been described in WO2007/060404 and WO2008/023161. There is a need for processes and intermediates that are useful in the preparation of certain pyrido-pyrimidine derivatives, which act as mTOR kinase inhibitors, and also to formulations, particularly in tablet form for use in the prevention and treatment of a wide variety of conditions.

SUMMARY OF THE INVENTION

According to a first aspect of the present invention there is provided a process for the preparation of a compound of Formula 1,

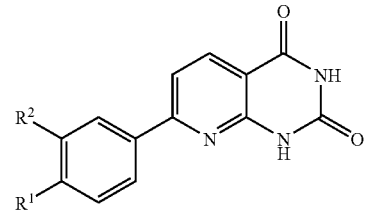

wherein
$R^1$ is hydrogen or $OR^3$;
$R^2$ is $CH_2OR^4$, $CN$, $CO_2R^5$ or $CONR^6R^7$;
$R^3$ is $C_{1-4}$alkyl group;
$R^4$ is a $—COR^8$ group wherein $R^5$ is a secondary $C_{3-6}$alkyl or tertiary $C_{4-6}$alkyl group;
$R^5$ is a $C_{1-4}$alkyl, a carbocyclyl, a carbocyclyl$C_{1-4}$alkyl, a heterocyclyl or heterocyclyl$C_{1-4}$alkyl group which is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ is hydrogen or $C_{1-4}$ alkyl group which is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl; and $R^7$ is $C_{1-4}$ alkyl group which is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl, comprising reacting a compound of Formula 2

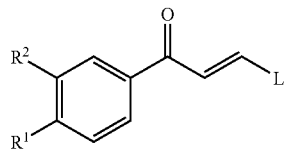

wherein
$R^1$ is hydrogen or $OR^3$;
$R^2$ is $CH_2OR^4$, CN, $CO_2R^5$ or $CONR^6R^7$;
$R^3$ is $C_{1-4}$ alkyl group;
$R^4$ is a —$COR^8$ group wherein $R^8$ is a secondary $C_{3-6}$alkyl or $C_{4-6}$tertiary alkyl group;
$R^5$ is a $C_{1-4}$alkyl, a carbocyclyl, a carbocyclyl$C_{1-4}$alkyl, a heterocyclyl or heterocyclyl$C_{1-4}$alkyl group which is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_6$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ is hydrogen or $C_{1-4}$ alkyl group which is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl; and $R^7$ is $C_{1-4}$ alkyl group which is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl; and L is a leaving group,
with a 6-substituted uracil equivalent.

In one embodiment L is a leaving group selected from $NR^aR^b$, $OR^c$, $SR^d$ and halogen, and wherein $R^a$, $R^b$, $R^c$ and $R^d$ are each independently hydrogen or a group selected from $C_{1-6}$alkyl, a carbocyclyl, a carbocyclyl$C_{1-6}$alkyl, a heterocyclyl and heterocyclyl$C_{1-6}$alkyl group which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl, or $R^a$ and $R^b$ together with the nitrogen atom to which they are attached form a 4- to 10-membered heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl.

In one embodiment the 6-substituted uracil equivalent is a 6-aminouracil or 6-aminothiouracil or derivatives thereof.

For example, 6-aminouracil, and derivatives thereof, include compounds of formula

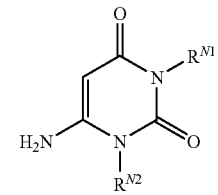

wherein $R^{N1}$ and $R^{N2}$ each independently are hydrogen or a protecting group, for example a benzyl group.

For example, 6-aminothiouracil, and derivatives thereof, include compounds of formula

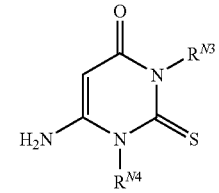

wherein $R^{N3}$ and $R^{N4}$ each independently are hydrogen or a protecting group, for example a benzyl group.

When a 6-aminothiouracil or 6 aminouracil derivative is employed any protecting groups may be optionally removed in a further step to give a compound of formula 1.

In another embodiment the 6-substituted uracil equivalent may result from the reaction of ammonia, and a 6-substituted uracil wherein the substituent is $C_{1-6}$alkyloxy, a carbocycly-loxy, a carbocyclyl$C_{1-6}$alkyloxy, $C_{1-6}$alkylthio, a carbocy-clylthio, a carbocyclyl$C_{1-6}$alkylthio group.

In one embodiment, the process may be carried out in the presence of a solvent, for example water miscible polar solvents such as dimethylformamide, N-methylpyrrollidone, dimethylsulphoxide or sulpholane.

In a further embodiment, the process of the present invention may be carried out in the presence of an acid, for example an organic acid such as acetic acid.

In a further embodiment, the compound of Formula 1 is isolated as the potassium salt by reaction with a potassium base, such as potassium carbonate or potassium hydroxide. In a further embodiment, the potassium salt is precipitated and collected, for example, by filtration. The compound of formula 1 can then be regenerated from the potassium salt by treatment with acid, for example citric acid.

According to another aspect of the present invention there is provided a process for the preparation of a compound of Formula 1,

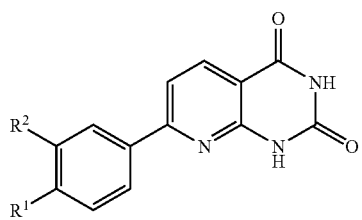

wherein
$R^1$ is hydrogen or $OR^3$;
$R^2$ is $CH_2R^4$, CN, $CO_2R^5$ or $CONR^6R^7$;
$R^3$ is $C_{1-4}$ alkyl group;
$R^4$ is a —$COR^8$ group wherein $R^8$ is a secondary $C_{3-6}$alkyl or tertiary $C_{4-6}$alkyl group;
$R^5$ is $C_{1-4}$ alkyl group;
$R^6$ is hydrogen or $C_{1-4}$ alkyl group; and
$R^7$ is $C_{1-4}$ alkyl group;
comprising reacting a compound of Formula 2a

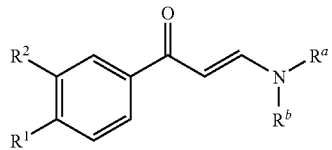

wherein
$R^1$ is hydrogen or $OR^3$;
$R^2$ is $CH_2OR^5$, CN, $CO_2R^5$ or $CONR^6R^7$;
$R^3$ is $C_{1-4}$ alkyl group;
$R^4$ is a —$COR^8$ group wherein $R^8$ is a secondary $C_{3-6}$alkyl or tertiary $C_{4-6}$alkyl group;
$R^5$ is $C_{1-4}$ alkyl group;
$R^6$ is hydrogen or $C_{1-4}$ alkyl group;
$R^7$ is $C_{1-4}$ alkyl group; and
$R^a$, $R^b$ are each independently hydrogen or a group selected from $C_{1-6}$alkyl, a carbocyclyl, a carbocyclyl$C_{1-6}$alkyl, a heterocyclyl and heterocyclyl$C_{1-6}$alkyl group which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl, or $R^a$ and $R^b$ together with the nitrogen atom to which they are attached form a 4- to 10-membered heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl,
with 6-aminouracil.

In one embodiment, the compound of Formula 2 is added to a mixture of 6-aminouracil and an acid, for example an organic such as acetic acid.

In a further embodiment, the compound of Formula 1 is isolated as the potassium salt by reaction with a potassium base, such as potassium carbonate or potassium hydroxide. In a further embodiment, the potassium salt is precipitated and collected, for example, by filtration. The compound of formula 1 can then be regenerated from the potassium salt by treatment with acid, for example citric acid.

A compound of Formula 2 where L is a leaving group selected from $NR^aR^b$ and $OR^c$ may be prepared by reacting a compound of Formula 3

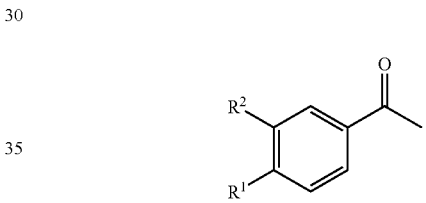

wherein
$R^1$ is hydrogen or $OR^3$;
$R^2$ is $CH_2OR^4$, CN, $CO_2R^5$ or $CONR^6R^7$;
$R^3$ is $C_{1-4}$ alkyl group;
$R^4$ is a —$COR^8$ group wherein $R^8$ is a secondary $C_{3-6}$alkyl or $C_{4-6}$tertiary alkyl group;
$R^5$ is a $C_{1-4}$alkyl, a carbocyclyl, a carbocyclyl$C_{1-4}$alkyl, a heterocyclyl or heterocyclyl$C_{1-4}$alkyl group which is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ is hydrogen or $C_{1-4}$ alkyl group which is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl; and $R^7$ is $C_{1-4}$ alkyl group which is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl, with aminomethylene derivative or an orthoformate derivative.

In one embodiment the aminomethylene derivative is substituted alkoxy bis(amino)methane such as Bredereck's reagent (t-butoxy bis(dimethylamino)methane).

In another embodiment the aminomethylene derivative is a substituted formamide acetal, for example a dimethyl formamide dialkyl acetal such as dimethyl formamide dimethyl acetal.

The reaction of a compound of Formula 3 with an aminomethylene derivative may be carried out in the presence of solvent, for example a polar aprotic solvent such as N-methylpyrrolidone or dimethyl formamide, or in mixtures of a polar aprotic solvent and non-polar solvents such as aromatic solvents such as toluene.

In one embodiment the orthoformate is trimethylorthoformate.

A compound of Formula 2 where L is a leaving group selected from $SR^d$ and halogen may be prepared from the corresponding phenyl acetylenic ketone by for example hydrohalogenation, or by reaction with thiols. (see Yakahiko Nishio et. al., J.C.S Perkin I, 1981, 934-938; Jose Juan Conde et. Al., Tetrahedron Letters 2000 (41) 4709-4711; or Shengming Ma et al., J. Org. Chem. 1992 (57) 709-713).

Compounds of Formula 3 may be prepared by literature methods.

According to a further aspect of the present invention there is provided a process of the preparation of a compound of Formula 1 comprising
i) reacting a compound of Formula 3 with an amino methylene derivative to give a compound of Formula 2 wherein
$R^1$ is hydrogen or $OR^3$;
$R^2$ is $CH_2R^4$, CN, $CO_2R^5$ or $CONR^6R^7$;
$R^3$ is $C_{1-4}$ alkyl group;
$R^4$ is a —$COR^8$ group wherein $R^8$ is a secondary $C_{3-6}$alkyl or $C_{4-6}$tertiary alkyl group;
$R^5$ is a $C_{1-4}$alkyl, a carbocyclyl, a carbocyclyl$C_{1-4}$alkyl, a heterocyclyl or heterocyclyl$C_{1-4}$alkyl group which is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl;

$R^6$ is hydrogen or $C_{1-4}$ alkyl group which is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl; and $R^7$ is $C_{1-4}$ alkyl group which is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl, wherein
$R^1$ is hydrogen or $OR^3$;
$R^2$ is $CH_2OR^4$, CN, $CO_2R^5$ or $CONR^6R^7$;
$R^3$ is $C_{1-4}$ alkyl group;
$R^4$ is a —$COR^8$ group wherein $R^8$ is a secondary $C_{3-6}$alkyl or $C_{4-6}$tertiary alkyl group;
$R^5$ is a $C_{1-4}$alkyl, a carbocyclyl, a carbocyclyl$C_{1-4}$alkyl, a heterocyclyl or heterocyclyl$C_{1-4}$alkyl group which is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl;

R$^6$ is hydrogen or C$_{1-4}$ alkyl group which is optionally substituted by one or more substituent groups selected from halo, cyano, nitro, hydroxy, oxo, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl; and R$^7$ is C$_{1-4}$ alkyl group which is optionally substituted by one or more substituent groups selected from halo, cyano, nitro, hydroxy, oxo, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl; and L is a leaving group,
and
ii) reacting a compound of Formula 2 with a 6-substituted uracil equivalent to give a compound of Formula 1.

According to a further aspect of the present invention there is provided a process of the preparation of a compound of Formula 1

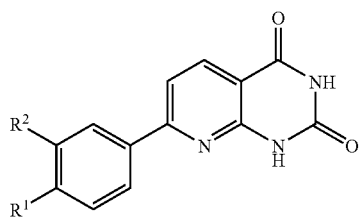

comprising
i) reacting a compound of Formula 3

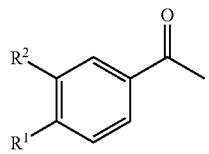

wherein
R$^1$ is hydrogen or OR$^3$;
R$^2$ is CH$_2$OR$^4$, CN, CO$_2$R$^5$ or CONR$^6$R$^7$;
R$^3$ is C$_{1-4}$ alkyl group;
R$^4$ is a —COR$^8$ group wherein R$^8$ is a secondary C$_{3-6}$alkyl or tertiary C$_{4-6}$alkyl group;
R$^5$ is C$_{1-4}$ alkyl group;
R$^6$ is hydrogen or C$_{1-4}$ alkyl group; and
R$^7$ is C$_{1-4}$ alkyl group
with an amino methylene derivative to give a compound of Formula 2a

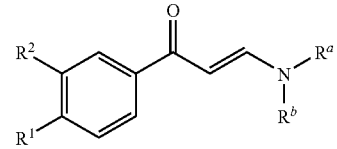

wherein
R$^1$ is hydrogen or OR$^3$;
R$^2$ is CH$_2$OR$^4$, CN, CO$_2$R$^5$ or CONR$^6$R$^7$;
R$^3$ is C$_{1-4}$ alkyl group;
R$^4$ is a —COR$^8$ group wherein R$^8$ is a secondary C$_{3-6}$alkyl or tertiary C$_{4-6}$alkyl group;
R$^5$ is C$_{1-4}$ alkyl group;
R$^6$ is hydrogen or C$_{1-4}$ alkyl group;
R$^7$ is C$_{1-4}$ alkyl group; and
R$^a$, R$^b$ are each independently hydrogen or a group selected from C$_{1-6}$alkyl, a carbocyclyl, a carbocyclylC$_{1-6}$alkyl, a heterocyclyl and heterocyclylC$_{1-6}$alkyl group which group is optionally substituted by one or more substituent groups selected from halo, cyano, nitro, hydroxy, oxo, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl, or R$^a$ and R$^b$ together with the nitrogen atom to which they are attached form a 4- to 10-membered heterocyclic ring wherein 1, 2 or 3 ring carbon atoms is optionally replaced with N, O or S and which ring is optionally substituted by one or more substituent groups selected from halo, cyano, nitro, hydroxy, oxo, C$_{1-6}$alkyl, C$_{1-6}$alkoxy, haloC$_{1-6}$alkyl, haloC$_{1-6}$alkoxy, hydroxyC$_{1-6}$alkyl, hydroxyC$_{1-6}$alkoxy, C$_{1-6}$alkoxyC$_{1-6}$alkyl, C$_{1-6}$alkoxyC$_{1-6}$alkoxy, amino, C$_{1-6}$alkylamino, bis(C$_{1-6}$alkyl)amino, aminoC$_{1-6}$alkyl, (C$_{1-6}$alkyl)aminoC$_{1-6}$alkyl, bis(C$_{1-6}$alkyl)aminoC$_{1-6}$alkyl, cyanoC$_{1-6}$alkyl, C$_{1-6}$alkylsulfonyl, C$_{1-6}$alkylsulfonylamino, C$_{1-6}$alkylsulfonyl(C$_{1-6}$alkyl)amino, sulfamoyl, C$_{1-6}$alkylsulfamoyl, bis(C$_{1-6}$alkyl)sulfamoyl, C$_{1-6}$alkanoylamino, C$_{1-6}$alkanoyl(C$_{1-6}$alkyl)amino, carbamoyl, C$_{1-6}$alkylcarbamoyl and bis(C$_{1-6}$alkyl)carbamoyl, and ii) reacting a compound of Formula 2a with 6-aminouracil to give a compound of Formula 1.

Compounds of Formula 2a may be reacted with certain halogenating agents or enolate trapping reagents to give a compound of Formula 2b

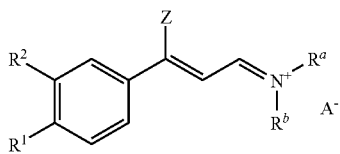

wherein

Z is halogen or $OSO_2R^9$, where $R^9$ is perfluoro$C_{1-4}$alkyl, and $A^-$ is a counterion, such as $PF_6^-$ Examples of halogenating agents include phosphorusoxychloride.

Examples of enolate trapping agents include trifluoromethanesulphonyl chloride.

Thus, according to a further aspect of the present invention there is provided a process of the preparation of a compound of Formula 1

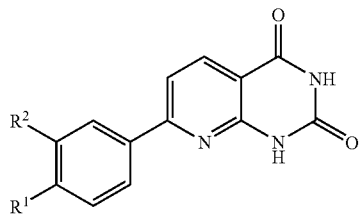

comprising i) reacting a compound of Formula 3

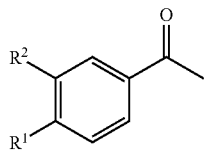

wherein $R^1$ is hydrogen or $OR^3$;

$R^2$ is $CH_2OR^4$, CN, $CO_2R^5$ or $CONR^6R^7$;

$R^3$ is $C_{1-4}$ alkyl group;

$R^4$ is a —$COR^8$ group wherein $R^8$ is a secondary $C_{3-6}$alkyl or tertiary $C_{4-6}$alkyl group;

$R^5$ is $C_{1-4}$ alkyl group;

$R^6$ is hydrogen or $C_{1-4}$ alkyl group; and $R^7$ is $C_{1-4}$ alkyl group with an amino methylene derivative to give a compound of Formula 2a

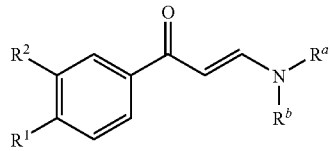

wherein $R^1$ is hydrogen or $OR^3$;

$R^1$ is $CH_2OR^4$, CN, $CO_2R^5$ or $CONR^6R^7$;

$R^3$ is $C_{1-4}$ alkyl group;

$R^4$ is a —$COR^8$ group wherein $R^8$ is a secondary $C_{3-6}$alkyl or tertiary $C_{4-6}$alkyl group;

$R^5$ is $C_{1-4}$ alkyl group;

$R^6$ is hydrogen or $C_{1-4}$ alkyl group;

$R^7$ is $C_{1-4}$ alkyl group; and $R^a$, $R^b$ are each independently hydrogen or a group selected from $C_{1-6}$alkyl, a carbocyclyl, a carbocyclyl$C_{1-6}$alkyl, a heterocyclyl and heterocyclyl$C_{1-6}$alkyl group which group is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl, or $R^a$ and $R^b$ together with the nitrogen atom to which they are attached form a 4- to 10-membered heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$alkyl, hydroxy$C_{1-6}$alkoxy, $C_{1-6}$alkoxy$C_{1-6}$alkyl, $C_{1-6}$alkoxy$C_{1-6}$alkoxy, amino, $C_{1-6}$alkylamino, bis($C_{1-6}$alkyl)amino, amino$C_{1-6}$alkyl, ($C_{1-6}$alkyl)amino$C_{1-6}$alkyl, bis($C_{1-6}$alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$alkyl)carbamoyl, ii) reacting a compound of Formula 2a with a halogenating agent or enolate trapping agent to give a compound of Formula 2b

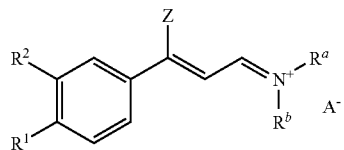

wherein
Z is halogen or $OSO_2R^9$, where $R^9$ is perfluoro$C_{1-4}$alkyl, and
$A^-$ is a counterion, such as $PF_6^-$
and
iii) reacting a compound of Formula 2b with 6-aminouracil to give a compound of Formula 1.

Compounds of Formula 1 may find use in the preparation of mTOR kinase inhibitors, for example the mTOR kinase inhibitors described in WO2007/060404 and WO2008/023161.

Thus, according to a further aspect of the present invention there is provided a process for the preparation of a mTOR kinase inhibitor of Formula 5

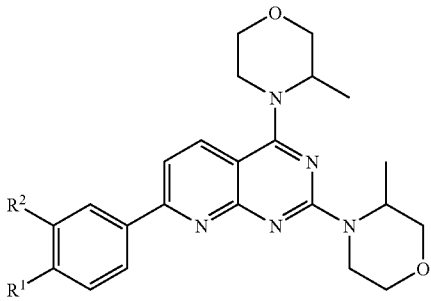

comprising
(i) preparing a compound of Formula 1 by one or more of the processes described hereinbefore,
(ii) reacting the compound of Formula 1 with a halogenating agent to give a compound of Formula 4

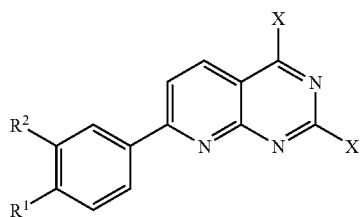

wherein X is a halogen,
(iii) reacting the compound of Formula 4 with methylmorpholine,
(iv) and optionally removing protecting groups to give an mTOR kinase inhibitor of Formula 5.

In a further aspect of the present invention there is provided a process for the preparation of a mTOR kinase inhibitor of Formula 5

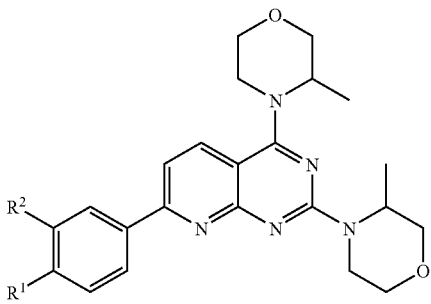

comprising
(i) preparing a compound of Formula 1 by one or more of the processes described hereinbefore,
(ii) reacting the compound of Formula 1 with a halogenating agent to give a compound of Formula 4

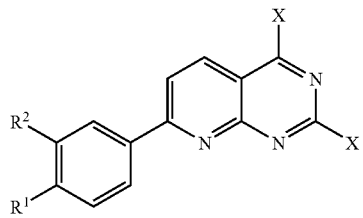

wherein X is a halogen,
(iii) reacting the compound of Formula 4 with methylmorpholine,
(iv) optionally removing protecting groups to give an mTOR kinase inhibitor of Formula 5,
(v) and optionally isolating the compound of formula 5 as a salt.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. For example compounds of Formula 5 may be converted into further compounds of Formula 5 by standard aromatic substitution reactions or by conventional functional group modifications. Such reactions and modifications include, for example, introduction of a substituent by means of an aromatic substitution reaction, reduction of substituents, alkylation of substituents, hydrolysis of esters, esterification, amidation and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulfinyl or alkylsulfonyl; hydrolysis of an ester to give an alcohol or acid; reduction of an ester to give an alcohol by for example using metal hydrides such as lithium borohydride, lithium aluminium hydride or diisobutylaluminum hydride; and reduction of a nitrile to give an alcohol by for example first carrying out reduction of the nitrile to an imine using metal hydrides, such as diisobutylaluminum hydride, followed by hydrolysis of the imine to give an aldehyde and reduction of the aldehyde using metal hydrides, such as sodium borohydride.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as pivaloyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

In a further embodiment, the compound of Formula 5 may be isolated as a salt.

Salts for use in pharmaceutical compositions will be pharmaceutically acceptable salts, but other salts may be useful in the production of the compound of Formula 5 and their pharmaceutically acceptable salts. Pharmaceutically acceptable salts of the invention may, for example, include acid addition salts of compound of Formula 5, as herein defined, wherein the compound of Formula 5 is sufficiently basic to form such salts, and base salts of compound of Formula 5, as herein defined, wherein the compound of Formula 5 is sufficiently acidic to form such salts.

In one embodiment the compound of Formula 5 is isolated as a phosphate, sulphate, hydrogensulphate, malate, citrate, tartrate or fumarate salt.

In one embodiment the compound of Formula 5 is isolated as a di-phosphate, D-tartrate or fumarate salt.

In another embodiment the compound of Formula 5 is isolated as a fumarate salt.

Many of the intermediates defined herein are novel and these are provided as a further feature of the invention.

In this specification the generic term "$C_{p-q}$alkyl" includes both straight-chain and branched-chain alkyl groups. However references to individual alkyl groups such as "propyl" are specific for the straight chain version only (i.e. n-propyl and isopropyl) and references to individual branched-chain alkyl groups such as "tert-butyl" are specific for the branched chain version only.

The term "secondary $C_{p-q}$alkyl" indicates branched-chain alkyl groups, where the branching is at the alpha carbon atom, for example "secondary $C_{3-4}$alkyl".

The prefix $C_{p-q}$ in $C_{p-q}$alkyl and other terms (where p and q are integers) indicates the range of carbon atoms that are present in the group, for example $C_{1-4}$alkyl includes $C_1$alkyl (methyl), $C_2$alkyl(ethyl), $C_3$alkyl(propyl as n-propyl and iso-propyl) and $C_4$alkyl (n-butyl, sec-butyl, isobutyl and tert-butyl).

The term $C_{p-q}$alkoxy comprises —O—$C_{p-q}$alkyl groups.
The term $C_{p-q}$alkanoyl comprises —C(O)alkyl groups.
The term halo includes fluoro, chloro, bromo and iodo.

"Carbocyclyl" is a saturated, unsaturated or partially saturated monocyclic, bicyclic or tricyclic ring system containing from 3 to 14 ring atoms, wherein a ring $CH_2$ group may be replaced with a C=O group. "Carbocyclyl" includes "aryl", "$C_{p-q}$cycloalkyl" and "$C_{p-q}$cycloalkenyl".

"aryl" is an aromatic monocyclic, bicyclic or tricyclic carbcyclyl ring system.

"$C_{p-q}$cycloalkenyl" is an unsaturated or partially saturated monocyclic, bicyclic or tricyclic carbocyclyl ring system containing at least 1 C=C bond and wherein a ring $CH_2$ group may be replaced with a C=O group.

"$C_{p-q}$cycloalkyl" is a saturated monocyclic, bicyclic or tricyclic carbocyclyl ring system and wherein a ring $CH_2$ group may be replaced with a C=O group.

"Heterocyclyl" is a saturated, unsaturated or partially saturated monocyclic, bicyclic or tricyclic ring system containing from 3 to 14 ring atoms of which 1, 2, 3 or 4 ring atoms are chosen from nitrogen, sulfur or oxygen, which ring may be carbon or nitrogen linked and wherein a ring nitrogen or sulfur atom may be oxidised and wherein a ring $CH_2$ group may be replaced with a C=O group. "Heterocyclyl" includes "heteroaryl", "cycloheteroalkyl" and "cycloheteroalkenyl".

"Heteroaryl" is an aromatic monocyclic, bicyclic or tricyclic heterocyclyl, particularly having 5 to 10 ring atoms, of which 1, 2, 3 or 4 ring atoms are chosen from nitrogen, sulfur or oxygen where a ring nitrogen or sulfur may be oxidised.

"Cycloheteroalkenyl" is an unsaturated or partially saturated monocyclic, bicyclic or tricyclic heterocyclyl ring system, particularly having 5 to 10 ring atoms, of which 1, 2, 3 or 4 ring atoms are chosen from nitrogen, sulfur or oxygen, which ring may be carbon or nitrogen linked and wherein a ring nitrogen or sulfur atom may be oxidised and wherein a ring $CH_2$ group may be replaced with a C=O group.

"Cycloheteroalkyl" is a saturated monocyclic, bicyclic or tricyclic heterocyclic ring system, particularly having 5 to 10 ring atoms, of which 1, 2, 3 or 4 ring atoms are chosen from nitrogen, sulfur or oxygen, which ring may be carbon or nitrogen linked and wherein a ring nitrogen or sulfur atom may be oxidised and wherein a ring $CH_2$ group may be replaced with a C=O group.

This specification may make use of composite terms to describe groups comprising more than one functionality.

Unless otherwise described herein, such terms are to be interpreted as is understood in the art. For example carbocyclyl$C_{p-q}$alkyl comprises $C_{p-q}$alkyl substituted by carbocyclyl, heterocyclyl$C_{p-q}$alkyl comprises $C_{p-q}$alkyl substituted by heterocyclyl, and bis($C_{p-q}$alkyl)amino comprises amino substituted by 2 $C_{p-q}$alkyl groups which may be the same or different.

Halo$C_{p-q}$alkyl is a $C_{p-q}$alkyl group that is substituted by 1 or more halo substituents and particularly 1, 2 or 3 halo substituents. Similarly, other generic terms containing halo such as halo$C_{p-q}$alkoxy may contain 1 or more halo substituents and particularly 1, 2 or 3 halo substituents.

Hydroxy$C_{p-q}$alkyl is a $C_{p-q}$alkyl group that is substituted by 1 or more hydroxyl substituents and particularly by 1, 2 or 3 hydroxy substituents. Similarly other generic terms containing hydroxy such as hydroxy$C_{p-q}$alkoxy may contain 1 or more and particularly 1, 2 or 3 hydroxy substituents.

$C_{p-q}$alkoxy$C_{p-q}$alkyl is a $C_{p-q}$alkyl group that is substituted by 1 or more $C_{p-q}$alkoxy substituents and particularly 1, 2 or 3 $C_{p-q}$alkoxy substituents. Similarly other generic terms containing $C_{p-q}$alkoxy such as $C_{p-q}$alkoxy$C_{p-q}$alkoxy may contain 1 or more $C_{p-q}$alkoxy substituents and particularly 1, 2 or 3 $C_{p-q}$alkoxy substituents.

Where optional substituents are chosen from "1 or 2", from "1, 2, or 3" or from "1, 2, 3 or 4" groups or substituents it is to be understood that this definition includes all substituents being chosen from one of the specified groups i.e. all substituents being the same or the substituents being chosen from two or more of the specified groups i.e. the substituents not being the same.

Compounds of the present invention have been named with the aid of computer software (ACD/Name version 9.0).

Suitable values for any R group or any part or substituent for such groups include:

| | |
|---|---|
| for $C_{1-4}$alkyl: | methyl, ethyl, propyl, butyl, 2-methylpropyl and tert-butyl; |
| for $C_{1-6}$alkyl: | $C_{1-4}$alkyl, pentyl, 2,2-dimethylpropyl, 3-methylbutyl and hexyl; |
| for $C_{3-6}$cycloalkyl: | cyclopropyl, cyclobutyl, cyclopentyl and cyclohexyl; |
| for $C_{3-6}$cycloalkyl$C_{1-4}$alkyl: | cyclopropylmethyl, cyclopropylethyl, cyclobutylmethyl, cyclopentylmethyl and cyclohexylmethyl; |
| for aryl: | phenyl and naphthyl; |
| for aryl$C_{1-4}$alkyl: | benzyl, phenethyl, naphthylmethyl and naphthylethyl; |
| for carbocylyl: | aryl, cyclohexenyl and $C_{3-6}$cycloalkyl; |
| for halo: | fluoro, chloro, bromo and iodo; |
| for halogen: | fluorine, chlorine, bromine and iodine; |
| for $C_{1-4}$alkoxy: | methoxy, ethoxy, propoxy and isopropoxy; |
| for $C_{1-6}$alkoxy: | $C_{1-4}$alkoxy, pentyloxy, 1-ethylpropoxy and hexyloxy; |
| for $C_{1-6}$alkanoyl: | acetyl, propanoyl and 2-methylpropanoyl; |
| for heteroaryl: | pyridyl, imidazolyl, quinolinyl, cinnolyl, pyrimidinyl, thienyl, pyrrolyl, pyrazolyl, thiazolyl, thiazolyl, triazolyl, oxazolyl, isoxazolyl, furanyl, pyridazinyl, pyrazinyl, indolyl, benzofuranyl, dibenzofuranyl and benzothienyl; |
| for heteroaryl$C_{1-4}$alkyl: | pyrrolylmethyl, pyrrolylethyl, imidazolylmethyl, imidazolylethyl, pyrazolylmethyl, pyrazolylethyl, furanylmethyl, furanylethyl, thienylmethyl, thienylethyl, pyridylmethyl, pyridylethyl, pyrazinylmethyl, pyrazinylethyl, pyrimidinylmethyl, pyrimidinylethyl, pyrimidinylpropyl, pyrimidinylbutyl, imidazolylpropyl, imidazolylbutyl, quinolinylpropyl, 1,3,4-triazolylpropyl and oxazolylmethyl; |
| for heterocyclyl: | heteroaryl, pyrrolidinyl, isoquinolinyl, quinoxalinyl, benzothiazolyl, benzoxazolyl, piperidinyl, piperazinyl, azetidinyl, morpholinyl, tetrahydroisoquinolinyl, tetrahydroquinolinyl, indolinyl, dihydro-2H-pyranyl and tetrahydrofuranyl. |

It should be noted that examples given for terms used in the description are not limiting.

Particular values of $R^1$, $R^2$, $R^3$, $R^4$, $R^5$, $R^6$, $R^7$, $R^8$, $R^a$, $R^b$, $R^c$, $R^d$, L and X are as follows. Such values may be used where appropriate, in connect with any aspect of the invention, or part thereof, and with any of the definitions, claims or embodiments defined herein.

$R^1$

In one aspect of the invention $R^1$ is hydrogen or methyl.

$R^2$

In one aspect of the invention $R^2$ is —$CH_2OCOC(CH_3)_3$, —CN, —$CO_2CH_3$ or —$CO2NHCH_3$ $R^3$ In one aspect of the invention $R^3$ is methyl $R^4$ In one aspect of the invention $R^4$ is —$COR^8$ wherein $R^8$ is $C_{4-6}$ tertiary alkyl.

In one aspect of the invention $R^4$ is —$COC(CH_3)_3$.

$R^5$

In one aspect of the invention $R^5$ is $C_{1-4}$alkyl, phenyl or benzyl group.

In one aspect of the invention $R^5$ is methyl.

$R^6$

In one aspect of the invention $R^6$ is hydrogen or $C_{1-4}$alkyl.

In one aspect of the invention $R^6$ is hydrogen or methyl.

In one aspect of the invention $R^6$ is hydrogen.

$R^7$

In one aspect of the invention $R^7$ is $C_{1-4}$alkyl.

In one aspect of the invention $R^7$ is methyl.

$R^8$

In one aspect of the invention $R^8$ is $C_{4-6}$ tertiary alkyl.

In one aspect of the invention $R^8$ is —$C(CH_3)_3$ $R^9$

In one aspect of the invention $R^9$ is —$CF_3$ $R^a$

In one aspect of the invention $R^a$ is hydrogen or $C_{1-4}$alkyl.

In another aspect of the invention $R^a$ is hydrogen or methyl.

In another aspect of the invention $R^a$ is methyl.

$R^b$

In one aspect of the invention $R^b$ is hydrogen or $C_{1-4}$alkyl.

In another aspect of the invention $R^b$ is hydrogen or methyl.

In another aspect of the invention $R^b$ is methyl.

$R^c$

In one aspect of the invention $R^c$ is selected from $R^d$

In one aspect of the invention $R^d$ is selected from $R^a$ and $R^b$

In one aspect of the invention only one of $R^a$ and $R^b$ is hydrogen.

In another aspect of the invention $R^a$ is hydrogen and $R^b$ is $C_{1-4}$alkyl.

In another aspect of the invention $R^a$ is hydrogen and $R^b$ is methyl.

In another aspect of the invention $R^a$ and $R^b$ is $C_{1-4}$alkyl.

In another aspect of the invention $R^a$ and $R^b$ is methyl.

In another aspect of the invention $R^a$ and $R^b$ together with the atoms to which they are attached form a ring.

L

In one aspect of the invention L is NR$^a$R$^b$.
In one aspect of the invention L is NMe$_2$.

X

In one aspect of the invention X is chlorine or bromine.
In another aspect of the invention X is chlorine.

Z

In one aspect of the invention Z is chlorine or —OSO$_2$CF$_3$
In another aspect of the invention Z is chlorine.
In another aspect of the invention Z is —OSO$_2$CF$_3$ Thus, according to a further aspect of the present invention there is provided a process for the preparation of a mTOR kinase inhibitor of Formula 5a

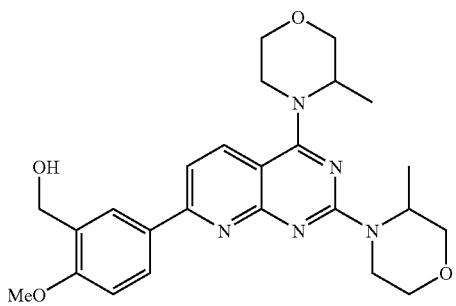

, or salt thereof, comprising
(i) preparing a compound of Formula 1

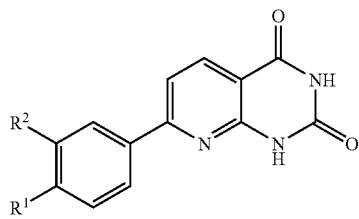

wherein
R$^1$ is OCH$_3$;
R$^2$ is CH$_2$OCOC(CH$_3$)$_3$ or CO$_2$CH$_3$;
by one or more of the processes described hereinbefore,
(ii) reacting the compound of Formula 1 with a halogenating agent to give a compound of Formula 4

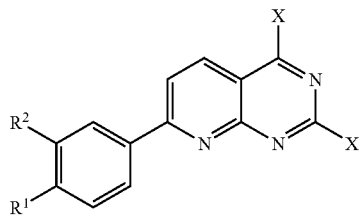

wherein X is a halogen,
(iii) reacting the compound of Formula 4 with methylmorpholine, and
(iv) either
when R$^2$ is CH$_2$OCOC(CH$_3$)$_3$ hydrolysing this ester protecting group to give a mTOR kinase inhibitor of Formula 5a
or
when R$^2$ is CO$_2$CH$_3$ reducing this ester group to give a mTOR kinase inhibitor of Formula 5a, and
(v) optionally converting the compound of Formula 5a to a salt.

In one embodiment the processes described herein may be used to prepare a fumarate salt of (5-{2,4-bis[(3S)-3-methyl-morpholin-4-yl]pyrido[2,3-d]pyrimidin-7-yl}-2-methoxyphenyl)methanol.

A particular compound of formula 5a is (5-{2,4-bis[(3S)-3-methylmorpholin-4-yl]pyrido[2,3-d]pyrimidin-7-yl}-2-methoxyphenyl)methanol.

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

While it is possible for the active compound to be administered alone, it is preferable to present it as a pharmaceutical composition (e.g., formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

In one embodiment the active ingredient may be administered in the form of a tablet. A tablet may be made by conventional means, e.g. compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

We have now discovered a novel formulation comprising a fumarate salt of a compound of Formula 5a.

Therefore in one aspect of the present invention there is provided a pharmaceutical composition which comprises a fumarate salt of a compound of Formula 5a with mannitol.

In another aspect of the invention there is provided a pharmaceutical composition which comprises a fumarate salt of a compound of Formula 5a, mannitol and dicalcium phosphate.

In another aspect of the invention there is provided a pharmaceutical composition which comprises a fumarate salt of a compound of Formula 5a, mannitol and dicalcium phosphate, wherein the weight ratio of mannitol:dicalcium phosphate is from about 10:1 to about 1:1. For example, the weight ratio of mannitol to dicalcium phosphate is from about 7.5:1 to about 3:1. In another embodiment the weight ratio of mannitol to dicalcium phosphate is about 7.5:1 to about 5:1. In a further embodiment the weight ratio of mannitol to dicalcium phosphate is from about 3:1 to about 1:1. For example the weight ratio of mannitol to dicalcium phosphate is about 2.35:1.

Mannitol refers to mannitol as described in the European Pharmacopoeia (PhEur). The composition according to the invention may use any mannitol suitable for use in pharmaceutical compositions such as tablets. In one embodiment the mannitol has average particle size in the range of from about 25 to about 180 µm, for example about 50 to about 170 µm, for tablets containing a fumarate salt of a compound of Formula 5a. In a particular embodiment the mannitol has an average particle size of about 160 µm. Suitably the bulk (poured) density of the mannitol (prior to incorporation into the composition) is about 0.6 to about 0.7 g/cm$^3$ and the tapped density is about 0.8 to about 0.9 g/cm$^3$. For example in one embodiment the bulk (poured) density is about 0.66 g/cm$^3$ and the tapped density is about 0.85 g/cm$^3$. In one embodiment the mannitol is substantially free from moisture prior to incorporation into the composition according to the invention (for example containing less than 5, 2 or 1% by weight water). In another embodiment the mannitol contains about 0.1 to 0.5% by weight of water prior to incorporation into the composition, for example about 0.2%. Mannitol as used herein may also refer to mannitol sold under the trade name Pearlitol® (ex Roquette Freres S.A.). In one embodiment the mannitol is Pearlitol® 160C.

Dicalcium phosphate refers to calcium hydrogen phosphate, anhydrous as described in the European Pharmacopoeia (PhEur). The composition according to the invention may use any dicalcium phosphate suitable for use in pharmaceutical compositions such as tablets. Suitably the bulk (poured) density of the dicalcium phosphate (prior to incorporation into the composition) is about 0.6 g/cm$^3$ to about 1 g/cm$^3$ and the tapped density is about 1.25 g/cm$^3$ to about 1.35 g/cm$^3$. For example in one embodiment the tapped density is about 1.28 g/cm$^3$. In one embodiment the dicalcium phosphate is substantially free from moisture prior to incorporation into the composition according to the invention (for example containing less than 10, 5 or 3% by weight water). In another embodiment the dicalcium phosphate contains about 0.3 to 2% by weight of water prior to incorporation into the composition, for example about 1%. Dicalcium phosphate as used herein may also refer to dicalcium phosphate sold under the trade name Calipharm (ex Innophos, Inc.). In one embodiment the dicalcium phosphate is Calipharm A®.

In one aspect the pharmaceutical composition additionally contains one or more disintegrants. In another aspect, the pharmaceutical composition additionally contains one disintegrant. In another aspect, the pharmaceutical composition additionally contains low-substituted hydroxypropyl cellulose (L-HPC). Any grade of L-HPC suitable for pharmaceutical formulation may be used, for example LH-21 (Shin Etsu Chemical Co.).

In one aspect the pharmaceutical composition additionally contains one or more binders. Suitable binders include, for example, lactose, starches, modified starches, sugars, gum acacia, gum tragacanth, guar gum, pectin, wax binders, methylcellulose, carboxymethylcellulose, hydroxypropyl methylcellulose, hydroxyethyl cellulose, hydroxypropyl cellulose, copolyvidone, gelatine, polyvinylpyrollidone (PVP or Povidone) and sodium alginate. In another aspect, the pharmaceutical composition additionally contains one binder selected from lactose, starches, modified starches, sugars, gum acacia, gum tragacanth, guar gum, pectin, wax binders, methylcellulose, carboxymethylcellulose, hydroxypropyl methylcellulose, hydroxyethyl cellulose, hydroxypropyl cellulose, copolyvidone, gelatine, polyvinylpyrollidone (Povidone) and sodium alginate. In another aspect, the pharmaceutical composition additionally contains hydroxypropyl cellulose.

The skilled reader will understand that a component of the tablet can act in more than one capacity. For example in some embodiments microcrystalline cellulose could act as a binder and/or a disintegrant as well as a filler.

In one aspect the pharmaceutical composition additionally contains one or more lubricants. Suitable lubricants include, for example, magnesium stearate, stearic acid, palmitic acid, calcium stearate, talc, carnuba wax, hydrogenated vegetable oils, mineral oil, polyethylene glycols and sodium stearyl fumarate. In another aspect, the pharmaceutical composition additionally contains one lubricant selected from magnesium stearate, stearic acid, palmitic acid, calcium stearate, talc, carnuba wax, hydrogenated vegetable oils, mineral oil, polyethylene glycols and sodium stearyl fumarate. In another aspect, the pharmaceutical composition additionally contains magnesium stearate.

In one aspect, the pharmaceutical composition contains from 2 to 50% by weight of a fumarate salt of a compound of Formula 5a. For example it contains from 15 to 35% by weight of a fumarate salt of a compound of Formula 5a. In one embodiment the composition contains 20 to 30% by weight of a fumarate salt of a compound of Formula 5a. In particular it contains 23 to 27% by weight of a fumarate salt of a compound of Formula 5a. Suitably the composition according to the invention, such as a capsule or tablet, contains 12.5 mg of a fumarate salt of a compound of Formula 5a. In another aspect the composition, such as a capsule or tablet, contains 25 mg of a fumarate salt of a compound of Formula 5a. In another aspect the composition, such as a capsule or tablet, contains 125 mg of a fumarate salt of a compound of Formula 5a.

In another aspect, the pharmaceutical composition contains from 50 to 95% by weight of filler. In another aspect the composition contains from 60 to 75% by weight of filler. In particular, it contains 65 to 69% by weight of filler.

In one aspect, the filler is mannitol. In another aspect, the filler is mannitol and dicalcium phosphate. In one embodiment the composition contains about 35 to 60% by weight of mannitol, for example about 45 to 49% by weight. In another embodiment the composition contains about 15 to 25% by weight of dicalcium, phosphate, for example about 18 to 22% by weight. In particular, the composition contains 19.0 to 21.0% by weight of dicalcium phosphate. In another embodiment the composition contains from about 45 to 49% by weight of mannitol and about 18 to 22% by weight of dicalcium phosphate.

In another aspect, the pharmaceutical composition contains from 1 to 10% by weight of disintegrant. In particular, it contains 6.5 to 7.5% by weight of disintegrant.

In another aspect, the pharmaceutical composition contains from 0 to 5% by weight of binder. In particular, it contains no binder.

Typically one or more lubricants will be present in an amount from 0.5 to 2.5% by weight, particularly 0.75 to 2% by weight and especially 0.75 to 1.25% by weight.

In one aspect the invention relates to a pharmaceutical composition comprising:
- a fumarate salt of a compound of Formula 5a in an amount of 23.0 to 27.0% by weight;
- mannitol in an amount of 45 to 49% by weight (for example 45.5 to 48.5% by weight); and
- dicalcium phosphate in an amount of 18.0 to 22.0% by weight.

In another aspect the invention relates to a pharmaceutical composition comprising:
- a fumarate salt of a compound of Formula 5a in an amount of 23.0 to 27.0% by weight;
- mannitol in an amount of 45 to 49% by weight (for example 45.5 to 48.5% by weight);
- dicalcium phosphate in an amount of 18.0 to 22.0% by weight;
- L-hydroxypropyl cellulose in an amount of 6.5 to 7.5% by weight; and
- one or more lubricants in an amount of 0.75 to 2.0% by weight (for example 0.75 to 1.25% by weight.

In another aspect the invention relates to a pharmaceutical composition comprising:
- a fumarate salt of a compound of Formula 5a in an amount of 23.0 to 27.0% by weight;
- mannitol in an amount of 45 to 49% by weight (for example 45.5 to 48.5% by weight);
- dicalcium phosphate in an amount of 18.0 to 22.0% by weight;
- L-Hydroxypropyl cellulose in an amount of 6.5 to 7.5% by weight; and
- magnesium stearate in an amount of 0.75 to 2.0% by weight (for example 0.75 to 1.25% by weight).

In another aspect the invention relates to a pharmaceutical composition comprising:
- a fumarate salt of a compound of Formula 5a in an amount of 23.0 to 27.0% by weight;
- mannitol in an amount of 45 to 49% by weight (for example 45.5 to 48.5% by weight);
- dicalcium phosphate in an amount of 18.0 to 22.0% by weight;
- L-Hydroxypropyl cellulose in an amount of 6.5 to 7.5% by weight; and
- one or more lubricants in an amount of 0.75 to 2.0% by weight (for example 0.75 to 1.25% by weight.

In another aspect the invention relates to a pharmaceutical composition comprising:
- a fumarate salt of a compound of Formula 5a in an amount of 23.0 to 27.0% by weight;
- mannitol in an amount of 45 to 49% by weight (for example 45.5 to 48.5% by weight);
- dicalcium phosphate in an amount of 18.0 to 22.0% by weight;
- L-Hydroxypropyl cellulose in an amount of 6.5 to 7.5% by weight; and
- magnesium stearate in an amount of 0.75 to 2.0% by weight (for example 0.75 to 1.25% by weight).

As will be realised, where herein compositions are described in terms of % by weight of components of the composition, the sum of the % by weight of all of the components of the composition is 100%.

In a further aspect the invention relates to a pharmaceutical composition, as described herein, prepared by wet granulation. The tablets described herein may be prepared by granulation, in particular wet granulation.

In direct compression methods, the drug substance, a compressible filler and other ingredients, if required, are mixed to a homogeneous composition then compressed in a tablet press to produce tablets. All materials used in a direct compression process must be carefully selected with regard to particle size distribution, density, physical form in order to avoid segregation during mixing and to ensure suitable flow and compression properties.

Such properties may also be conferred by granulation, which is a process by which primary particles (powders) are made to adhere to form larger, multiparticulate entities called granules. Granulation normally commences after initial dry mixing of the powdered ingredients so that a fairly uniform distribution of ingredients through the mix is achieved. Granulation methods can be divided into two types, wet granulation methods that utilize a liquid to form the granules and dry methods that do not.

Wet granulation involves mixing the components to be granulated as a dry mix (for example a fumarate salt of a compound of Formula 5a, diluent(s), disintegrant(s) and optionally a binder). The dry mix is then massed using a granulating fluid to form granules. Sufficient granulating fluid is added to the dry mix to form granules during the granulation process, for example 10 to 50% by weight, suitably 15 to 25% by weight, of granulating fluid is added to the dry mix during the granulation. The granulating fluid may contain a solvent, which can be removed by drying, and is non-toxic. Suitably however, the granulating fluid is water. The granulating fluid can be used alone or with a binding agent (binder) to ensure particle adhesion in the dry state. Binding agents can be added to the system as a binder solution (as part of the granulating fluid) or as dry material mixed with the primary powder particles (as part of the dry mix). Suitably the granulating liquid is added to the dry powder mix in a manner to provide a substantially uniform liquid content in the mixture, for example by spraying the liquid onto the powder during the granulation. Wet granulators are well known and any suitable granulator may be used to form the wet granules. There are three main types of wet granulator, shear granulators (such as planetary mixers), high shear mixer granulators (such as Vector, Fielder, Collette Gral or Diosna) and fluid bed granulators (such as Aeromatic or Glatt).

Following wet granulation the resulting wet mass may be passed through a coarse mesh (for example a 9 mm mesh) to remove any large lumps that may have formed during the granulation. The granules are dried to a suitable moisture content, typically less that 2% by weight water, using a suitable drying method such as fluid bed drying. The resulting granules are then optionally milled to give a more homogenous particle size distribution.

In dry granulation methods, primary powder particles are aggregated under pressure (or compaction). There are two main processes: a large tablet (also known as a slug) is produced with a heavy duty tablet press or the powder particles are compressed between two rollers to produce a sheet or 'ribbon' of material (process known as roller compaction). In both cases, the compacted material is milled using a suitable milling technique to produce granular material. The granules can then be compressed in a standard tablet press to produce tablets.

Following granulation the granules might be used in a capsule composition or compressed to form a tablet. Suitably to form a tablet, the granules may be blended with a lubricant and then compressed into tablets. A suitable coating may then be applied to the tablets as described herein.

In another aspect there is provided a pharmaceutical composition, as disclosed herein, prepared by a wet granulation process that is suitable for oral administration.

In another aspect the invention relates to a pharmaceutical composition obtainable by a wet granulation process comprising a fumarate salt of a compound of Formula 5a with mannitol and dicalcium phosphate.

In a further feature of the present invention the present inventors have found that they are able to manufacture satisfactory batches of the preferred composition, using either a direct compression grade or a wet granulation grade of mannitol, by a wet granulation process.

"Direct compression grade mannitol", for example Parteck™ M grades of mannitol supplied by Merck Chemicals Ltd., can be produced by a spray drying process causing the mannitol to crystallise in a needle-like microstructure while building up a granular macrostructure. Suitably the average particle size of the direct compression grade mannitol is about 150 to 350 μm, for example 200 to 300 μm. Suitably the direct compression grade mannitol has a bulk (poured) density (prior to incorporation into the composition) of about 0.4 to 0.5 g/cm$^3$l and the tapped density is about 0.55 g/cm$^3$ to about 0.65 g/cm$^3$. Examples of direct compression grade mannitol prepared by spray drying include Parteck™ M200, Parteck™ M300, Pearlitol™ SD200 or Mannogem™ EZ. In one embodiment of the invention the mannitol is Parteck™ M200.

"Wet granulation grade mannitol" generally has a more granular particle shape than direct compression grade mannitol. Suitably the wet granulation grade mannitol has an average particle size in the range of about 100 to 300 μm. For example Pearlitol™ 160 C supplied by Roquette Freres S.A., comprises cubic crystals having a mean diameter of 160 microns.

In another aspect the invention relates to a pharmaceutical composition obtainable by a wet granulation process comprising wet granulation of a fumarate salt of a compound of Formula 5a with mannitol and dicalcium phosphate wherein direct compression grade mannitol is used in the wet granulation process.

In another aspect the invention relates to a pharmaceutical composition obtainable by a wet granulation process comprising wet granulation of a fumarate salt of a compound of Formula 5a with mannitol and dicalcium phosphate wherein wet granulation grade mannitol is used in the wet granulation process.

Where the composition comprising a fumarate salt of a compound of Formula 5a with mannitol and dicalcium phosphate is prepared by wet granulation, particularly wet granulation grade mannitol is used.

In another aspect the invention relates to a pharmaceutical composition obtainable by a wet granulation process comprising wet granulation of a fumarate salt of a compound of Formula 5a, mannitol, dicalcium phosphate, L-Hydroxypropyl cellulose, optionally a binder and a lubricant.

In another aspect the invention relates to a pharmaceutical composition obtainable by a wet granulation process comprising wet granulation of a fumarate salt of a compound of Formula 5a, mannitol, dicalcium phosphate, L-hydroxypropyl cellulose, optionally a binder and magnesium stearate.

In another aspect the invention relates to a pharmaceutical composition obtainable by a wet granulation process comprising wet granulation of a fumarate salt of a compound of Formula 5a, mannitol, dicalcium phosphate, L-hydroxypropyl cellulose, optionally hydroxypropyl cellulose and a lubricant.

In another aspect the invention relates to a pharmaceutical composition obtainable by a wet granulation process comprising wet granulation of a fumarate salt of a compound of Formula 5a, mannitol, dicalcium phosphate, L-hydroxypropyl cellulose, optionally hydroxypropyl cellulose and magnesium stearate.

In another aspect the invention relates to a pharmaceutical composition obtainable by a wet granulation process comprising wet granulation of a fumarate salt of a compound of Formula 5a, mannitol, dicalcium phosphate, L-hydroxypropyl cellulose and magnesium stearate.

In another aspect the invention relates to a pharmaceutical composition obtainable by a wet granulation process comprising wet granulation of a fumarate salt of a compound of Formula 5a, mannitol, dicalcium phosphate, L-hydroxypropyl cellulose and optionally a binder.

In another aspect the invention relates to a pharmaceutical tablet composition obtainable by a wet granulation process comprising:

(i) wet granulation of a fumarate salt of a compound of Formula 5a, mannitol, dicalcium phosphate, L-hydroxypropyl cellulose and optionally a binder;

(ii) blending the resulting granules with a lubricant; and (iii) compressing the mixture from step (iii) into tablets.

In these embodiments any of the mannitol, dicalcium phosphate, L-hydroxypropyl cellulose, binder and lubricants described herein may be used. In a particular embodiment the mannitol is a wet granulation grade mannitol such as Pearlitol™ 160 C.

In one aspect the pharmaceutical composition is in a solid dosage form, such as a tablet or capsule. In another aspect the pharmaceutical composition is in the form of a tablet. In a further feature of the invention the composition is in the form of a tablet designed for immediate release. Suitably the immediate release tablet will disintegrate quickly following administration as hereinbefore described. For example, typically represented by in-vitro dissolution times of about 2 to 20 minutes and typically 10 to 15 minutes.

According to a further aspect of the invention there is provided a process for the preparation of a pharmaceutical composition according to the invention comprising mixing a fumarate salt of a compound of Formula 5a and the mannitol and dicalcium phosphate and forming the mixture into a unit dosage form such as a tablet or capsule.

In one embodiment of the process, following mixing of a fumarate salt of a compound of Formula 5a and the mannitol and dicalcium phosphate (and other optional ingredients as required such as a binder and disintegrant as hereinbefore described) the mixture is granulated and formed into a suitable unit dosage form. Suitable granulation methods are as hereinbefore described. For example the mixture may be wet granulated as described herein. When a binder is used in the composition the binder such as hydroxypropyl cellulose may be incorporated into the mixture prior to granulation as a dry powder. Following granulation the granules may be dried and milled and, for example, compressed into a tablet as described hereinbefore. Suitably the composition is provided with a means for protecting a fumarate salt of a compound of Formula 5a from light degradation as described hereinafter. For example, when the composition is in the form of a tablet, the tablet is provided with a light protective coating as described hereinafter.

Accordingly, a further aspect of the invention there is provides a process for the preparation of a pharmaceutical immediate release tablet composition according to the invention comprising:
(i) mixing a fumarate salt of a compound of Formula 5a and the mannitol and dicalcium phosphate;
(ii) granulating the mixture formed in step (i) to form granules;
(iii) optionally milling the granules;
(iv) mixing the granules with a lubricant; and
(v) compressing the granules into a tablet.

Additional excipients such as a disintegrant and binder may be included in the mixture in step (i) of the process as described hereinbefore and illustrated in the examples.

In a particular embodiment the granulation step (ii) is a wet granulation as described hereinbefore. When the granulation step (ii) is a wet granulation, the granules are suitably dried prior to milling (if carried out) and subsequent compression into tablets.

In a further embodiment of the process for the preparation of the pharmaceutical immediate release tablet composition, the process further comprises coating the tablets from step (v) with a film coating.

The fumarate salt of a compound of Formula 5a exists in certain crystalline forms. In a particular aspect of the invention, a fumarate salt of a compound of Formula 5a is in crystalline Form A.

In another aspect the invention relates to a pharmaceutical composition as hereinabove defined in which a fumarate salt of a compound of Formula 5a is in a crystalline form.

In another aspect the invention relates to a pharmaceutical composition as hereinabove defined comprising a fumarate salt of a compound of Formula 5a wherein the salt is present in one or more crystalline forms.

In another aspect the invention relates to a pharmaceutical composition as hereinabove defined comprising a fumarate salt of a compound of Formula 5a wherein the salt is present in one or more crystalline forms selected from Form A, Form B and Form C.

In yet another aspect the invention relates to a pharmaceutical composition as hereinbefore defined comprising a fumarate salt of a compound of Formula 5a substantially as crystalline Form A.

In another aspect the invention relates to a pharmaceutical composition as hereinabove defined comprising a fumarate salt of (5-{2,4-bis[(3S)-3-methylmorpholin-4-yl]pyrido[2,3-d]pyrimidin-7-yl}-2-methoxyphenyl)methanol wherein the salt is present in one or more crystalline forms selected from Form A, Form B and Form C.

In yet another aspect the invention relates to a pharmaceutical composition as hereinbefore defined comprising a fumarate salt of (5-{2,4-bis[(3S)-3-methylmorpholin-4-yl]pyrido[2,3-d]pyrimidin-7-yl}-2-methoxyphenyl)methanol substantially as crystalline Form A.

Substantially as Form A means that there is greater than 95% of Form A present. In particular there is greater than 96% Form A. Particularly there is greater than 97% Form A. In particular there is greater than 98% Form A. Particularly there is greater than 99% Form A. In particular there is greater than 99.5% Form A. Particularly there is greater than 99.8% Form A.

In a further embodiment, there is provided a crystalline form of a fumarate salt of (5-{2,4-bis[(3S)-3-methylmorpholin-4-yl]pyrido[2,3-d]pyrimidin-7-yl}-2-methoxyphenyl)methanol having an XRD pattern comprising peaks at 2-theta ($\lambda$=1.5418 Å) 6.0, 9.6, 12.2, 13.0 and 17.9.

In a further embodiment, there is provided a crystalline form of a fumarate salt of (5-{2,4-bis[(3S)-3-methylmorpholin-4-yl]pyrido[2,3-d]pyrimidin-7-yl}-2-methoxyphenyl)methanol having an XRD pattern comprising peaks at 2-theta ($\lambda$=1.5418 Å) 6.0, 9.6, 12.2, 13.0, 17.1, 17.6, 17.9, 18.3, 19.2, 19.4 and 21.6.

In a further embodiment, there is provided a crystalline form of a fumarate salt of (5-{2,4-bis[(3S)-3-methylmorpholin-4-yl]pyrido[2,3-d]pyrimidin-7-yl}-2-methoxyphenyl)methanol having an XRD pattern comprising peaks at 2-theta ($\lambda$=1.5418 Å) 6.0, 8.5, 9.6, 12.2, 13.0 and 17.9.

In a further embodiment, there is provided a crystalline form of a fumarate salt of (5-{2,4-bis[(3S)-3-methylmorpholin-4-yl]pyrido[2,3-d]pyrimidin-7-yl}-2-methoxyphenyl)methanol having an XRD pattern comprising peaks at 2-theta ($\lambda$=1.5418 Å) 6.0, 8.5, 9.6, 12.2, 13.0, 17.1, 17.7, 17.9, 18.3 and 19.3.

In a further embodiment, there is provided a crystalline form of a fumarate salt of (5-{2,4-bis[(3S)-3-methylmorpholin-4-yl]pyrido[2,3-d]pyrimidin-7-yl}-2-methoxyphenyl)methanol having an XRD pattern comprising peaks at 2-theta ($\lambda$=1.5418 Å) 6.3, 9.2, 10.1, 14.4 and 18.9.

In a further embodiment, there is provided a crystalline form of a fumarate salt of (5-{2,4-bis[(3S)-3-methylmorpholin-4-yl]pyrido[2,3-d]pyrimidin-7-yl}-2-methoxyphenyl)methanol having an XRD pattern comprising peaks at 2-theta ($\lambda$=1.5418 Å) 6.3, 9.2, 10.1, 13.3, 14.4, 18.9, 20.3 and 22.0.

A person skilled in the art will appreciate that the diffraction pattern data presented herein is not to be construed as absolute (for further information see Jenkins, R & Snyder, R. L. 'Introduction to X-Ray Powder Diffractometry' John Wiley & Sons, 1996). Therefore, it shall be understood that the crystalline form is not intended to be limited to the crystals that provide X-ray powder diffraction patterns identical to the X-ray powder diffraction patterns described herein. The present invention also includes any crystals providing X-ray powder diffraction patterns substantially the same as those described herein. A person skilled in the art of X-ray powder diffraction is able to judge the substantial similarity of X-ray powder diffraction patterns and will understand that differences may be the result of various factors for example measurement errors resulting from measurement conditions (such as equipment, sample preparation or the machine used); intensity variations resulting from measurement conditions and sample preparation; relative intensity variations of peaks resulting from variations in size or non-unitary aspect ratios of crystals; and the position of reflections which can be affected by the precise height at which the sample sits in the diffractometer and the zero calibration of the diffractometer, and surface planarity of the sample.

As mentioned hereinbefore, when the composition is in the form of a tablet, the tablet is suitably coated with a film. In one embodiment of the invention the composition is in the form of a tablet coated with a coating, suitably a film coating, comprising an iron oxide pigment. In this embodiment the iron oxide pigment is suitably present at about 0.025 to 1% by weight of the tablet. In one embodiment of the invention the iron oxide pigment is present at about 0.06% by weight of the tablet. In a further embodiment, the iron oxide pigment is present at about 0.6% by weight of the tablet. The tablet coating may be applied using for example a commercially available coating such as the Opadry™ films supplied by Colorcon Inc.

In one aspect the pharmaceutical composition is a tablet with a coating comprising one or more colouring agents. In another aspect, the pharmaceutical composition is a tablet with a coating comprising one colouring agent. In another aspect, the pharmaceutical composition is a tablet with a coating comprising an iron oxide pigment. In another aspect, the pharmaceutical composition is a tablet with a coating comprising iron oxide yellow. Coatings containing iron oxide pigments are commercially available, for example Opadry II Yellow (Colorcon85F38196 or Colorcon 85F32410), which may be applied to the tablet as an aqueous solution or suspension.

In one aspect the pharmaceutical composition is a tablet with a weight of coating between, for example 1 to 10%, such as 2 and 10% by weight of the tablet core weight, for example 3 to 6% by weight of the tablet core weight. In particular, the weight of coating is 3 to 4% by weight of the tablet core weight. In another embodiment the weight of the coating is from about 1 to about 2% by weight of the tablet core weight.

In one aspect the pharmaceutical composition is a tablet with a coating comprising one or more film formers. In another aspect, the pharmaceutical composition is a tablet with a coating comprising one film former. In another aspect, the pharmaceutical composition is a tablet with a coating comprising a water-soluble film-former such as a polyvinyl alcohol (defined in the PhEur).

In one aspect the pharmaceutical composition is a tablet with a coating comprising one or more opacifiers. In another aspect, the pharmaceutical composition is a tablet with a coating comprising one opacifier. In another aspect, the pharmaceutical composition is a tablet with a coating comprising titanium dioxide.

In one aspect the pharmaceutical composition is a tablet with a coating comprising one or more anti-tack agents. In another aspect, the pharmaceutical composition is a tablet with a coating comprising one anti-tack agent. In another aspect, the pharmaceutical composition is a tablet with a coating comprising talc.

In one aspect the pharmaceutical composition is a tablet with a coating comprising one or more plasticisers. In another aspect, the pharmaceutical composition is a tablet with a coating comprising one plasticiser. In another aspect, the pharmaceutical composition is a tablet with a coating comprising a polyethylene glycol plasticiser, for example Macrogol 3350 (defined in the PhEur).

Tablet coating may be carried out using conventional methods well known in the art, for example coating in a pan coater. The film coat may be applied by spraying an aqueous suspension of the film former, opacifier, plasticiser and colouring agents onto the tablet cores.

In another aspect the invention relates to a pharmaceutical composition comprising a fumarate salt of a compound of Formula 5a which is a tablet with a coating comprising iron oxide yellow.

In another aspect the invention relates to a pharmaceutical composition comprising a fumarate salt of a compound of Formula 5a which is a tablet with a coating comprising polyvinyl alcohol, titanium dioxide, Macrogol 3350, iron oxide yellow and talc.

In another aspect the invention relates to a tablet comprising a core comprising a fumarate salt of a compound of Formula 5a with mannitol and dicalcium phosphate and a coating comprising iron oxide yellow and talc.

In another aspect the invention relates to a tablet comprising a core comprising a fumarate salt of a compound of Formula 5a with mannitol and dicalcium phosphate and a coating comprising polyvinyl alcohol, titanium dioxide, Macrogol 3350, iron oxide yellow and talc.

In another aspect, the coating contains from 30 to 50% by weight of film former. In particular, it contains 38.0 to 42.0% by weight of film formers.

In another aspect, the coating contains from 5 to 25% by weight of opacifier. In one embodiment, it contains 8.0 to 12.0% by weight of opacifier. In a further embodiment, it contains between 21.5 and 25.5% by weight of opacifier.

In another aspect, the coating contains from 10 to 30% by weight of plasticiser. In particular, it contains 18.2 to 22.2% by weight of plasticiser.

In another aspect, the coating contains from 1 to 20% by weight of iron oxide pigments. In one embodiment, it contains 13.0-17.0% by weight of iron oxide pigments. In a further embodiment it contains 1.0-2.0% by weight of iron oxide pigments.

In another aspect, the coating contains from 14.5 to 15.1% by weight of talc.

In another aspect, the coating contains from 0.05 to 1.0% by weight of iron oxide pigment(s) and from 0.25 to 1.5% by weight of titanium dioxide. For example in one embodiment a coating containing about 0.6% by weight of iron oxide and about 0.4% by weight of titanium dioxide, or in a further embodiment a coating containing about 0.06% by weight of iron oxide and about 0.94% by weight of titanium dioxide, wherein the weights are % weight relative to the weight of the tablet core to which the coating is applied.

In one aspect the invention relates to a pharmaceutical composition comprising a tablet core and a coating wherein the tablet core comprises:
  a fumarate salt of a compound of Formula 5a in an amount of 23.0 to 27.0% by weight of the core;
  mannitol in an amount of 45.5 to 48.5% by weight of the core; and
  dicalcium phosphate in an amount of 18.0 to 22.0% by weight of the core;
and wherein, in one embodiment, the coating on the tablet core comprises:
  iron oxide yellow in an amount of 12.5 to 17.5% by weight of the coating; and;
  titanium dioxide in an amount of 8.0 to 12.0% by weight of the coating
and in a further embodiment, the coating on the tablet core comprises:
  iron oxide yellow in an amount of 1.0 to 2.0% by weight of the coating; and;
  titanium dioxide in an amount of 22.0 to 25.0% by weight of the coating.

In another aspect the invention relates to a pharmaceutical composition comprising a core comprising a fumarate salt of a compound of Formula 5a and, in one embodiment, a coating comprising:
  a water-soluble film-former such as polyvinyl alcohol in an amount of 38.0 to 42.0% by weight;
  a polyethylene glycol plasticiser such as Macrogol 3350 in an amount of 18.2 to 22.2% by weight;
  talc in an amount of 14.5 to 15.1% by weight
  iron oxide yellow in an amount of 12.5 to 17.5% by weight of the coating; and;
  titanium dioxide in an amount of 8.0 to 12.0% by weight of the coating;
In a further embodiment, the coating comprises:
  a water-soluble film-former such as polyvinyl alcohol in an amount of 38.0 to 42.0% by weight;
  a polyethylene glycol plasticiser such as Macrogol 3350 in an amount of 18.2 to 22.2% by weight;
  talc in an amount of 14.5 to 15.1% by weight;
  iron oxide yellow in an amount of 1.0 to 2.0% by weight of the coating; and;
  titanium dioxide in an amount of 22.0 to 25.0% by weight of the coating;
wherein the weights are % by weight of the coating.

In another aspect the invention relates to a pharmaceutical composition comprising a core comprising a fumarate salt of a compound of Formula 5a and mannitol with optional dicalcium phosphate and, in one embodiment, a coating comprising:
  a water-soluble film-former such as polyvinyl alcohol in an amount of 38.0 to 42.0% by weight;
  a polyethylene glycol plasticiser such as Macrogol 3350 in an amount of 18.2 to 22.2% by weight;
  talc in an amount of 14.5 to 15.1% by weight
  iron oxide yellow in an amount of 12.5 to 17.5% by weight of the coating; and;
  titanium dioxide in an amount of 8.0 to 12.0% by weight of the coating.
In a further embodiment, the coating comprises:
  a water-soluble film-former such as polyvinyl alcohol in an amount of 38.0 to 42.0% by weight;
  a polyethylene glycol plasticiser such as Macrogol 3350 in an amount of 18.2 to 22.2% by weight;
  talc in an amount of 14.5 to 15.1% by weight;
  iron oxide yellow in an amount of 1.0 to 2.0% by weight of the coating; and;
  titanium dioxide in an amount of 22.0 to 25.0% by weight of the coating;
wherein the weights are % by weight of the coating.

In another aspect the invention relates to a pharmaceutical immediate release tablet composition comprising a tablet core and a coating, wherein the tablet core comprises:
  a fumarate salt of a compound of Formula 5a in an amount of 23.0 to 27.0% by weight of the tablet core;
  mannitol in an amount of 45.5 to 48.5% by weight of the tablet core;
  dicalcium phosphate in an amount of 18.0 to 22.0% by weight of the tablet core;
  L-hydroxypropyl cellulose in an amount of 6.5 to 7.5% by weight of the tablet core; and
  a lubricant (for example magnesium stearate) in an amount of 0.75 to 2.0% by weight (for example 0.8 to 1.75% by weight);
and wherein the coating on the tablet core comprises an iron oxide pigment and wherein the coating is present in an amount of 3 to 6% by weight of the tablet core.

In another aspect the invention relates to a pharmaceutical immediate release tablet composition comprising a tablet core and a coating, wherein the tablet core comprises:
  a fumarate salt of a compound of Formula 5a in an amount of 23.0 to 27.0% by weight of the tablet core;
  mannitol in an amount of 45.5 to 48.5% by weight of the tablet core;
  dicalcium phosphate in an amount of 18.0 to 22.0% by weight of the tablet core;
  L-hydroxypropyl cellulose in an amount of 6.5 to 7.5% by weight of the tablet core; and
  a lubricant (for example magnesium stearate) in an amount of 0.75 to 2.0% by weight (for example 0.8 to 1.75% by weight);
and wherein, in one embodiment, a coating on the tablet core comprising:
  a water-soluble film-former such as polyvinyl alcohol in an amount of 38.0 to 42.0% by weight;
  a polyethylene glycol plasticiser such as Macrogol 3350 in an amount of 18.2 to 22.2% by weight;
  talc in an amount of 14.5 to 15.1% by weight
  iron oxide yellow in an amount of 12.5 to 17.5% by weight of the coating; and;
  titanium dioxide in an amount of 8.0 to 12.0% by weight of the coating;
In a further embodiment, the coating comprises:
  a water-soluble film-former such as polyvinyl alcohol in an amount of 38.0 to 42.0% by weight;
  a polyethylene glycol plasticiser such as Macrogol 3350 in an amount of 18.2 to 22.2% by weight;
  talc in an amount of 14.5 to 15.1% by weight;
  iron oxide yellow in an amount of 1.0 to 2.0% by weight of the coating; and;
  titanium dioxide in an amount of 22.0 to 25.0% by weight of the coating;
wherein the weights are % by weight of the coating.

Suitably in these embodiments the coating is present in an amount of 2.5 to 5% by weight of the tablet core, for example about 4.0% by weight of the tablet core.

It is known that mTOR kinase and the PI3K enzymes have roles in tumourigenesis as well as numerous other diseases. Pharmaceutical composition comprising a fumarate salt of a compound of Formula 5a may possess potent anti-tumour activity by way of inhibition of mTOR kinase.

Accordingly, the compounds of the present invention are of value as anti-tumour agents. Particularly, the compounds of the present invention are of value as anti-proliferative, apoptotic and/or anti-invasive agents in the containment and/or treatment of solid and/or liquid tumour disease. Particularly, the compounds of the present invention are expected to be useful in the prevention or treatment of those tumours which are sensitive to inhibition of mTOR. Further, the compounds of the present invention are expected to be useful in the prevention or treatment of those tumours which are mediated alone or in part by mTOR. The compounds may thus be used to produce an mTOR enzyme inhibitory effect in a warm-blooded animal in need of such treatment.

Inhibitors of mTOR kinase should be of therapeutic value for the treatment of proliferative disease such as cancer and in particular solid tumours such as carcinoma and sarcomas and the leukaemias and lymphoid malignancies and in particular for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias [including acute lymphoctic leukaemia (ALL) and chronic myelogenous leukaemia (CML)], multiple myeloma and lymphomas.

Anti-cancer effects which are accordingly useful in the treatment of cancer in a patient include, but are not limited to, anti-tumour effects, the response rate, the time to disease progression and the survival rate. Anti-tumour effects of a method of treatment of the present invention include but are not limited to, inhibition of tumour growth, tumour growth delay, regression of tumour, shrinkage of tumour, increased time to regrowth of tumour on cessation of treatment, slowing of disease progression. Anti-cancer effects include prophylactic treatment as well as treatment of existing disease.

A mTOR kinase inhibitor, or a pharmaceutically acceptable salt thereof, may also be useful for the treatment patients with cancers, including, but not limited to, haematologic malignancies such as leukaemia, multiple myeloma, lymphomas such as Hodgkin's disease, non-Hodgkin's lymphomas (including mantle cell lymphoma), and myelodysplastic syndromes, and also solid tumours and their metastases such as breast cancer, lung cancer (non-small cell lung cancer (NSCL), small cell lung cancer (SCLC), squamous cell carcinoma), endometrial cancer, tumours of the central nervous system such as gliomas, dysembryoplastic neuroepithelial tumour, glioblastoma multiforme, mixed gliomas, medulloblastoma, retinoblastoma, neuroblastoma, germinoma and teratoma, cancers of the gastrointestinal tract such as gastric cancer, oesophagal cancer, hepatocellular (liver) carcinoma, cholangiocarcinomas, colon and rectal carcinomas, cancers of the small intestine, pancreatic cancers, cancers of the skin such as melanomas (in particular metastatic melanoma), thyroid cancers, cancers of the head and neck and cancers of the salivary glands, prostate, testis, ovary, cervix, uterus, vulva, bladder, kidney (including renal cell carcinoma, clear cell and renal oncocytoma), squamous cell carcinomas, sarcomas such as osteosarcoma, chondrosarcoma, leiomyosarcoma, soft tissue sarcoma, Ewing's sarcoma, gastrointestinal stromal tumour (GIST), Kaposi's sarcoma, and paediatric cancers such as rhabdomyosarcomas and neuroblastomas.

The compounds of the present invention and the methods of treatment comprising the administering or use of a mTOR kinase inhibitor, or a pharmaceutically acceptable salt thereof, are expected to be particularly useful for the treatment of patients with lung cancer, prostate cancer, melanoma, ovarian cancer, breast cancer, endometrial cancer, kidney cancer, gastric cancer, sarcomas, head and neck cancers, tumours of the central nervous system and their metastases, and also for the treatment of patients with acute myeloid leukaemia.

According to a further aspect of the invention there is provided a pharmaceutical composition which comprises a fumarate salt of a compound of formula (5a) for use as a medicament in a warm-blooded animal such as man.

According to a further aspect of the invention there is provided a pharmaceutical composition which comprises a fumarate salt of a compound of formula (5a) with mannitol for use as a medicament in a warm-blooded animal such as man.

According to a further aspect of the invention there is provided a pharmaceutical composition which comprises a fumarate salt of a compound of formula (5a) with mannitol and dicalcium phosphate for use as a medicament in a warm-blooded animal such as man.

According to a further aspect of the invention, there is provided a pharmaceutical composition which comprises a fumarate salt of a compound of formula (5a) for use in the production of an anti-proliferative effect in a warm-blooded animal such as man.

According to a further aspect of the invention, there is provided a pharmaceutical composition which comprises a fumarate salt of a compound of formula (5a) with mannitol for use in the production of an anti-proliferative effect in a warm-blooded animal such as man.

According to a further aspect of the invention, there is provided a pharmaceutical composition which comprises a fumarate salt of a compound of formula (5a) with mannitol and dicalcium phosphate for use in the production of an anti-proliferative effect in a warm-blooded animal such as man.

According to a further aspect of the invention, there is provided a pharmaceutical composition which comprises a fumarate salt of a compound of formula (5a) for use in the production of an apoptotic effect in a warm-blooded animal such as man.

According to a further aspect of the invention, there is provided a pharmaceutical composition which comprises a fumarate salt of a compound of formula (5a) with mannitol for use in the production of an apoptotic effect in a warm-blooded animal such as man.

According to a further aspect of the invention, there is provided a pharmaceutical composition which comprises a fumarate salt of a compound of formula (5a) with mannitol and dicalcium phosphate for use in the production of an apoptotic effect in a warm-blooded animal such as man.

According to a further feature of the invention there is provided a pharmaceutical composition which comprises a fumarate salt of a compound of formula (5a) for use in a warm-blooded animal such as man as an anti-invasive agent in the containment and/or treatment of proliferative disease such as cancer.

According to a further feature of the invention there is provided a pharmaceutical composition which comprises a fumarate salt of a compound of formula (5a) with mannitol for use in a warm-blooded animal such as man as an anti-invasive agent in the containment and/or treatment of proliferative disease such as cancer.

According to a further feature of the invention there is provided a pharmaceutical composition which comprises a fumarate salt of a compound of formula (5a) with mannitol and dicalcium phosphate for use in a warm-blooded animal such as man as an anti-invasive agent in the containment and/or treatment of proliferative disease such as cancer.

According to a further aspect of the invention, there is provided the use of a pharmaceutical composition which comprises a fumarate salt of a compound of formula (5a) for the production of an anti-proliferative effect in a warm-blooded animal such as man.

According to a further aspect of the invention, there is provided the use of a pharmaceutical composition which comprises a fumarate salt of a compound of formula (5a) with mannitol for the production of an anti-proliferative effect in a warm-blooded animal such as man.

According to a further aspect of the invention, there is provided the use of a pharmaceutical composition which comprises a fumarate salt of a compound of formula (5a) with mannitol and dicalcium phosphate for the production of an anti-proliferative effect in a warm-blooded animal such as man.

According to a further feature of this aspect of the invention there is provided the use of a pharmaceutical composition which comprises a fumarate salt of a compound of formula (5a) in the manufacture of a medicament for use in the production of an anti-proliferative effect in a warm-blooded animal such as man.

According to a further feature of this aspect of the invention there is provided the use of a pharmaceutical composition which comprises a fumarate salt of a compound of formula (5a) with mannitol in the manufacture of a medicament for use in the production of an anti-proliferative effect in a warm-blooded animal such as man.

According to a further feature of this aspect of the invention there is provided the use of a pharmaceutical composition which comprises a fumarate salt of a compound of formula (5a) with mannitol and dicalcium phosphate in the manufacture of a medicament for use in the production of an anti-proliferative effect in a warm-blooded animal such as man.

According to a further aspect of the invention, there is provided the use of a pharmaceutical composition which comprises a fumarate salt of a compound of formula (5a) for the production of an apoptotic effect in a warm-blooded animal such as man.

According to a further aspect of the invention, there is provided the use of a pharmaceutical composition which comprises a fumarate salt of a compound of formula (5a) with mannitol for the production of an apoptotic effect in a warm-blooded animal such as man.

According to a further aspect of the invention, there is provided the use of a pharmaceutical composition which comprises a fumarate salt of a compound of formula (5a) with mannitol and dicalcium phosphate for the production of an apoptotic effect in a warm-blooded animal such as man.

According to a further feature of this aspect of the invention there is provided the use of a pharmaceutical composition which comprises a fumarate salt of a compound of formula (5a) in the manufacture of a medicament for use in the production of an apoptotic effect in a warm-blooded animal such as man.

According to a further feature of this aspect of the invention there is provided the use of a pharmaceutical composition which comprises a fumarate salt of a compound of formula (5a) with mannitol in the manufacture of a medicament for use in the production of an apoptotic effect in a warm-blooded animal such as man.

According to a further feature of this aspect of the invention there is provided the use of a pharmaceutical composition which comprises a fumarate salt of a compound of formula (5a) with mannitol and dicalcium phosphate in the manufacture of a medicament for use in the production of an apoptotic effect in a warm-blooded animal such as man.

According to a further feature of the invention there is provided the use of a pharmaceutical composition which comprises a fumarate salt of a compound of formula (5a) with in the manufacture of a medicament for use in a warm-blooded animal such as man as an anti-invasive agent in the containment and/or treatment of proliferative disease such as cancer.

According to a further feature of the invention there is provided the use of a pharmaceutical composition which comprises a fumarate salt of a compound of formula (5a) with mannitol in the manufacture of a medicament for use in a warm-blooded animal such as man as an anti-invasive agent in the containment and/or treatment of proliferative disease such as cancer.

According to a further feature of the invention there is provided the use of a pharmaceutical composition which comprises a fumarate salt of a compound of formula (5a) with mannitol and dicalcium phosphate in the manufacture of a medicament for use in a warm-blooded animal such as man as an anti-invasive agent in the containment and/or treatment of proliferative disease such as cancer.

According to a further feature of this aspect of the invention there is provided a method for producing an anti-proliferative effect in a warm-blooded animal, such as man, in need of such treatment which comprises administering to said animal an effective amount of a pharmaceutical composition which comprises a fumarate salt of a compound of formula (5a).

According to a further feature of this aspect of the invention there is provided a method for producing an anti-proliferative effect in a warm-blooded animal, such as man, in need of such treatment which comprises administering to said animal an effective amount of a pharmaceutical composition which comprises a fumarate salt of a compound of formula (5a) with mannitol.

According to a further feature of this aspect of the invention there is provided a method for producing an anti-proliferative effect in a warm-blooded animal, such as man, in need of such treatment which comprises administering to said animal an effective amount of a pharmaceutical composition which comprises a fumarate salt of a compound of formula (5a) with mannitol and dicalcium phosphate.

According to a further feature of this aspect of the invention there is provided a method for producing an anti-invasive effect by the containment and/or treatment of solid tumour disease in a warm-blooded animal, such as man, in need of such treatment which comprises administering to said animal an effective amount of a pharmaceutical composition which comprises a fumarate salt of a compound of formula (5a).

According to a further feature of this aspect of the invention there is provided a method for producing an anti-invasive effect by the containment and/or treatment of solid tumour disease in a warm-blooded animal, such as man, in need of such treatment which comprises administering to said animal an effective amount of a pharmaceutical composition which comprises a fumarate salt of a compound of formula (5a) with mannitol.

According to a further feature of this aspect of the invention there is provided a method for producing an anti-invasive effect by the containment and/or treatment of solid tumour disease in a warm-blooded animal, such as man, in need of such treatment which comprises administering to said animal an effective amount of a pharmaceutical composition which comprises a fumarate salt of a compound of formula (5a) with mannitol and dicalcium phosphate.

According to a further aspect of the invention there is provided the use of a pharmaceutical composition which comprises a fumarate salt of a compound of formula (5a) in the manufacture of a medicament for use in the prevention or treatment of proliferative disease such as cancer in a warm-blooded animal such as man.

According to a further aspect of the invention there is provided the use of a pharmaceutical composition which comprises a fumarate salt of a compound of formula (5a) with mannitol in the manufacture of a medicament for use in the prevention or treatment of proliferative disease such as cancer in a warm-blooded animal such as man.

According to a further aspect of the invention there is provided the use of a pharmaceutical composition which comprises a fumarate salt of a compound of formula (5a) with mannitol and dicalcium phosphate in the manufacture of a medicament for use in the prevention or treatment of proliferative disease such as cancer in a warm-blooded animal such as man.

According to a further feature of this aspect of the invention there is provided a method for the prevention or treatment of proliferative disease such as cancer in a warm-blooded animal, such as man, in need of such treatment which comprises administering to said animal an effective amount of a pharmaceutical composition which comprises a fumarate salt of a compound of formula (5a).

According to a further feature of this aspect of the invention there is provided a method for the prevention or treatment of proliferative disease such as cancer in a warm-blooded animal, such as man, in need of such treatment which comprises administering to said animal an effective amount of a pharmaceutical composition which comprises a fumarate salt of a compound of formula (5a) with mannitol.

According to a further feature of this aspect of the invention there is provided a method for the prevention or treatment of proliferative disease such as cancer in a warm-blooded animal, such as man, in need of such treatment which comprises administering to said animal an effective amount of a pharmaceutical composition which comprises a fumarate salt of a compound of formula (5a) with mannitol and dicalcium phosphate.

According to a further aspect of the invention there is provided a pharmaceutical composition which comprises a fumarate salt of a compound of formula (5a) for use in the prevention or treatment of those tumours which are sensitive to inhibition of mTOR kinase that are involved in the signal transduction steps which lead to the proliferation, survival, invasiveness and migratory ability of tumour cells.

According to a further aspect of the invention there is provided a pharmaceutical composition which comprises a fumarate salt of a compound of formula (5a) with mannitol for use in the prevention or treatment of those tumours which are sensitive to inhibition of mTOR kinase that are involved in the signal transduction steps which lead to the proliferation, survival, invasiveness and migratory ability of tumour cells.

According to a further aspect of the invention there is provided a pharmaceutical composition which comprises a fumarate salt of a compound of formula (5a) with mannitol and dicalcium phosphate for use in the prevention or treatment of those tumours which are sensitive to inhibition of mTOR kinase that are involved in the signal transduction steps which lead to the proliferation, survival, invasiveness and migratory ability of tumour cells.

According to a further feature of this aspect of the invention there is provided the use of a pharmaceutical composition which comprises a fumarate salt of a compound of formula (5a) in the manufacture of a medicament for use in the prevention or treatment of those tumours which are sensitive to inhibition of mTOR kinase that are involved in the signal transduction steps which lead to the proliferation, survival, invasiveness and migratory ability of tumour cells.

According to a further feature of this aspect of the invention there is provided the use of a pharmaceutical composition which comprises a fumarate salt of a compound of formula (5a) with mannitol in the manufacture of a medicament for use in the prevention or treatment of those tumours which are sensitive to inhibition of mTOR kinase that are involved in the signal transduction steps which lead to the proliferation, survival, invasiveness and migratory ability of tumour cells.

According to a further feature of this aspect of the invention there is provided the use of a pharmaceutical composition which comprises a fumarate salt of a compound of formula (5a) with mannitol and dicalcium phosphate in the manufacture of a medicament for use in the prevention or treatment of those tumours which are sensitive to inhibition of mTOR kinase that are involved in the signal transduction steps which lead to the proliferation, survival, invasiveness and migratory ability of tumour cells.

According to a further feature of this aspect of the invention there is provided a method for the prevention or treatment of those tumours which are sensitive to inhibition of mTOR kinase that are involved in the signal transduction steps which lead to the proliferation, survival, invasiveness and migratory ability of tumour cells which comprises administering to said animal an effective amount of a pharmaceutical composition which comprises a fumarate salt of a compound of formula (5a).

According to a further feature of this aspect of the invention there is provided a method for the prevention or treatment of those tumours which are sensitive to inhibition of mTOR kinase that are involved in the signal transduction steps which lead to the proliferation, survival, invasiveness and migratory ability of tumour cells which comprises administering to said animal an effective amount of a pharmaceutical composition which comprises a fumarate salt of a compound of formula (5a) with mannitol.

According to a further feature of this aspect of the invention there is provided a method for the prevention or treatment of those tumours which are sensitive to inhibition of mTOR kinase that are involved in the signal transduction steps which lead to the proliferation, survival, invasiveness and migratory ability of tumour cells which comprises administering to said animal an effective amount of a pharmaceutical composition which comprises a fumarate salt of a compound of formula (5a) with mannitol and dicalcium phosphate.

According to a further aspect of the invention there is provided a pharmaceutical composition which comprises a fumarate salt of a compound of formula (5a) for use in providing a mTOR kinase inhibitory effect.

According to a further aspect of the invention there is provided a pharmaceutical composition which comprises a fumarate salt of a compound of formula (5a) with mannitol for use in providing a mTOR kinase inhibitory effect.

According to a further aspect of the invention there is provided a pharmaceutical composition which comprises a fumarate salt of a compound of formula (5a) with mannitol and dicalcium phosphate for use in providing a mTOR kinase inhibitory effect.

According to a further feature of this aspect of the invention there is provided the use of a pharmaceutical composition which comprises a fumarate salt of a compound of formula (5a) in the manufacture of a medicament for use in providing a mTOR kinase inhibitory effect.

According to a further feature of this aspect of the invention there is provided the use of a pharmaceutical composition which comprises a fumarate salt of a compound of formula (5a) with mannitol in the manufacture of a medicament for use in providing a mTOR kinase inhibitory effect.

According to a further feature of this aspect of the invention there is provided the use of a pharmaceutical composition which comprises a fumarate salt of a compound of formula (5a) with mannitol and dicalcium phosphate in the manufacture of a medicament for use in providing a mTOR kinase inhibitory effect.

According to a further aspect of the invention there is also provided a method for providing a mTOR kinase inhibitory effect which comprises administering an effective amount of a pharmaceutical composition which comprises a fumarate salt of a compound of formula (5a).

According to a further aspect of the invention there is also provided a method for providing a mTOR kinase inhibitory effect which comprises administering an effective amount of a pharmaceutical composition which comprises a fumarate salt of a compound of formula (5a) with mannitol.

According to a further aspect of the invention there is also provided a method for providing a mTOR kinase inhibitory effect which comprises administering an effective amount of a pharmaceutical composition which comprises a fumarate salt of a compound of formula (5a) with mannitol and dicalcium phosphate.

According to a further feature of the invention there is provided a pharmaceutical composition which comprises a fumarate salt of a compound of formula (5a) for use in the treatment of cancer, inflammatory diseases, obstructive airways diseases, immune diseases or cardiovascular diseases.

According to a further feature of the invention there is provided a pharmaceutical composition which comprises a fumarate salt of a compound of formula (5a) with mannitol for use in the treatment of cancer, inflammatory diseases, obstructive airways diseases, immune diseases or cardiovascular diseases.

According to a further feature of the invention there is provided a pharmaceutical composition which comprises a fumarate salt of a compound of formula (5a) with mannitol and dicalcium phosphate for use in the treatment of cancer, inflammatory diseases, obstructive airways diseases, immune diseases or cardiovascular diseases.

According to a further feature of the invention there is provided a pharmaceutical composition which comprises a fumarate salt of a compound of formula (5a) for use in the treatment of solid tumours such as carcinoma and sarcomas and the leukaemias and lymphoid malignancies.

According to a further feature of the invention there is provided a pharmaceutical composition which comprises a fumarate salt of a compound of formula (5a) with mannitol for use in the treatment of solid tumours such as carcinoma and sarcomas and the leukaemias and lymphoid malignancies.

According to a further feature of the invention there is provided a pharmaceutical composition which comprises a fumarate salt of a compound of formula (5a) with mannitol and dicalcium phosphate for use in the treatment of solid tumours such as carcinoma and sarcomas and the leukaemias and lymphoid malignancies.

According to a further feature of the invention there is provided a pharmaceutical composition which comprises a fumarate salt of a compound of formula (5a) for use in the treatment of cancer of the breast, colorectum, lung (including small cell lung cancer, non-small cell lung cancer and bronchioalveolar cancer) and prostate.

According to a further feature of the invention there is provided a pharmaceutical composition which comprises a fumarate salt of a compound of formula (5a) with mannitol for use in the treatment of cancer of the breast, colorectum, lung (including small cell lung cancer, non-small cell lung cancer and bronchioalveolar cancer) and prostate.

According to a further feature of the invention there is provided a pharmaceutical composition which comprises a fumarate salt of a compound of formula (5a) with mannitol and dicalcium phosphate for use in the treatment of cancer of the breast, colorectum, lung (including small cell lung cancer, non-small cell lung cancer and bronchioalveolar cancer) and prostate.

According to a further feature of the invention there is provided a pharmaceutical composition which comprises a fumarate salt of a compound of formula (5a) for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of the invention there is provided a pharmaceutical composition which comprises a fumarate salt of a compound of formula (5a) with mannitol for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of the invention there is provided a pharmaceutical composition which comprises a fumarate salt of a compound of formula (5a) with mannitol and dicalcium phosphate for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of the invention there is provided a pharmaceutical composition which comprises a fumarate salt of a compound of formula (5a) for use in the treatment of cancer of the bile duct, bone, bladder, head and neck, kidney, liver, gastrointestinal tissue, oesophagus, ovary, endometrium, pancreas, skin, testes, thyroid, uterus, cervix and vulva, and of leukaemias (including ALL and CML), multiple myeloma and lymphomas.

According to a further feature of the invention there is provided a pharmaceutical composition which comprises a fumarate salt of a compound of formula (5a) with mannitol for use in the treatment of cancer of the bile duct, bone, bladder, head and neck, kidney, liver, gastrointestinal tissue, oesophagus, ovary, endometrium, pancreas, skin, testes, thyroid, uterus, cervix and vulva, and of leukaemias (including ALL and CML), multiple myeloma and lymphomas.

According to a further feature of the invention there is provided a pharmaceutical composition which comprises a fumarate salt of a compound of formula (5a) with mannitol and dicalcium phosphate for use in the treatment of cancer of the bile duct, bone, bladder, head and neck, kidney, liver, gastrointestinal tissue, oesophagus, ovary, endometrium, pancreas, skin, testes, thyroid, uterus, cervix and vulva, and of leukaemias (including ALL and CML), multiple myeloma and lymphomas.

According to a further feature of the invention there is provided a pharmaceutical composition which comprises a fumarate salt of a compound of formula (5a) for use in the treatment of lung cancer, prostate cancer, melanoma, ovarian cancer, breast cancer, endometrial cancer, kidney cancer, gastric cancer, sarcomas, head and neck cancers, tumours of the central nervous system and their metastases, and also for the treatment acute myeloid leukaemia.

According to a further feature of the invention there is provided a pharmaceutical composition which comprises a fumarate salt of a compound of formula (5a) with mannitol for use in the treatment of lung cancer, prostate cancer, melanoma, ovarian cancer, breast cancer, endometrial cancer, kidney cancer, gastric cancer, sarcomas, head and neck cancers, tumours of the central nervous system and their metastases, and also for the treatment acute myeloid leukaemia.

According to a further feature of the invention there is provided a pharmaceutical composition which comprises a fumarate salt of a compound of formula (5a) with mannitol and dicalcium phosphate for use in the treatment of lung cancer, prostate cancer, melanoma, ovarian cancer, breast cancer, endometrial cancer, kidney cancer, gastric cancer, sarcomas, head and neck cancers, tumours of the central nervous system and their metastases, and also for the treatment acute myeloid leukaemia.

According to a further feature of the invention there is provided the use of a pharmaceutical composition which comprises a fumarate salt of a compound of formula (5a) in the manufacture of a medicament for use in the treatment of cancer, inflammatory diseases, obstructive airways diseases, immune diseases or cardiovascular diseases.

According to a further feature of the invention there is provided the use of a pharmaceutical composition which comprises a fumarate salt of a compound of formula (5a) with mannitol in the manufacture of a medicament for use in the treatment of cancer, inflammatory diseases, obstructive airways diseases, immune diseases or cardiovascular diseases.

According to a further feature of the invention there is provided the use of a pharmaceutical composition which comprises a fumarate salt of a compound of formula (5a) with mannitol and dicalcium phosphate in the manufacture of a medicament for use in the treatment of cancer, inflammatory diseases, obstructive airways diseases, immune diseases or cardiovascular diseases.

According to a further feature of the invention there is provided the use of a pharmaceutical composition which comprises a fumarate salt of a compound of formula (5a) in the manufacture of a medicament for use in the treatment of solid tumours such as carcinoma and sarcomas and the leukaemias and lymphoid malignancies.

According to a further feature of the invention there is provided the use of a pharmaceutical composition which comprises a fumarate salt of a compound of formula (5a) with mannitol in the manufacture of a medicament for use in the treatment of solid tumours such as carcinoma and sarcomas and the leukaemias and lymphoid malignancies.

According to a further feature of the invention there is provided the use of a pharmaceutical composition which comprises a fumarate salt of a compound of formula (5a) with mannitol and dicalcium phosphate in the manufacture of a medicament for use in the treatment of solid tumours such as carcinoma and sarcomas and the leukaemias and lymphoid malignancies.

According to a further feature of the invention there is provided the use of a pharmaceutical composition which comprises a fumarate salt of a compound of formula (5a) in the manufacture of a medicament for use in the treatment of cancer of the breast, colorectum, lung (including small cell lung cancer, non-small cell lung cancer and bronchioalveolar cancer) and prostate.

According to a further feature of the invention there is provided the use of a pharmaceutical composition which comprises a fumarate salt of a compound of formula (5a) with mannitol in the manufacture of a medicament for use in the treatment of cancer of the breast, colorectum, lung (including small cell lung cancer, non-small cell lung cancer and bronchioalveolar cancer) and prostate.

According to a further feature of the invention there is provided the use of a pharmaceutical composition which comprises a fumarate salt of a compound of formula (5a) with mannitol and dicalcium phosphate in the manufacture of a medicament for use in the treatment of cancer of the breast, colorectum, lung (including small cell lung cancer, non-small cell lung cancer and bronchioalveolar cancer) and prostate.

According to a further feature of the invention there is provided the use of a pharmaceutical composition which comprises a fumarate salt of a compound of formula (5a) in the manufacture of a medicament for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of the invention there is provided the use of a pharmaceutical composition which comprises a fumarate salt of a compound of formula (5a) with mannitol in the manufacture of a medicament for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of the invention there is provided the use of a pharmaceutical composition which comprises a fumarate salt of a compound of formula (5a) with mannitol and dicalcium phosphate in the manufacture of a medicament for use in the treatment of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

According to a further feature of the invention there is provided the use of a pharmaceutical composition which comprises a fumarate salt of a compound of formula (5a) in the manufacture of a medicament for use in the treatment of lung cancer, prostate cancer, melanoma, ovarian cancer, breast cancer, endometrial cancer, kidney cancer, gastric cancer, sarcomas, head and neck cancers, tumours of the central nervous system and their metastases, and also for the treatment acute myeloid leukaemia.

According to a further feature of the invention there is provided the use of a pharmaceutical composition which comprises a fumarate salt of a compound of formula (5a) with mannitol in the manufacture of a medicament for use in the treatment of lung cancer, prostate cancer, melanoma, ovarian cancer, breast cancer, endometrial cancer, kidney cancer, gastric cancer, sarcomas, head and neck cancers, tumours of the central nervous system and their metastases, and also for the treatment acute myeloid leukaemia.

According to a further feature of the invention there is provided the use of a pharmaceutical composition which comprises a fumarate salt of a compound of formula (5a) with mannitol and dicalcium phosphate in the manufacture of a medicament for use in the treatment of lung cancer, prostate cancer, melanoma, ovarian cancer, breast cancer, endometrial cancer, kidney cancer, gastric cancer, sarcomas, head and neck cancers, tumours of the central nervous system and their metastases, and also for the treatment acute myeloid leukaemia.

According to a further feature of the invention there is provided a method for treating cancer, inflammatory diseases, obstructive airways diseases, immune diseases or cardiovascular diseases in a warm blooded animal such as man that is in need of such treatment which comprises administering an effective amount of a pharmaceutical composition which comprises a fumarate salt of a compound of formula (5a).

According to a further feature of the invention there is provided a method for treating cancer, inflammatory diseases, obstructive airways diseases, immune diseases or cardiovascular diseases in a warm blooded animal such as man that is in need of such treatment which comprises administering an effective amount of a pharmaceutical composition which comprises a fumarate salt of a compound of formula (5a) with mannitol.

According to a further feature of the invention there is provided a method for treating cancer, inflammatory diseases, obstructive airways diseases, immune diseases or cardiovascular diseases in a warm blooded animal such as man that is in need of such treatment which comprises administering an effective amount of a pharmaceutical composition which comprises a fumarate salt of a compound of formula (5a) with mannitol and dicalcium phosphate.

According to a further feature of the invention there is provided a method for treating solid tumours such as carcinoma and sarcomas and the leukaemias and lymphoid malignancies in a warm blooded animal such as man that is in need of such treatment which comprises administering an effective amount of a pharmaceutical composition which comprises a fumarate salt of a compound of formula (5a).

According to a further feature of the invention there is provided a method for treating solid tumours such as carcinoma and sarcomas and the leukaemias and lymphoid malignancies in a warm blooded animal such as man that is in need of such treatment which comprises administering an effective amount of a pharmaceutical composition which comprises a fumarate salt of a compound of formula (5a) with mannitol.

According to a further feature of the invention there is provided a method for treating solid tumours such as carcinoma and sarcomas and the leukaemias and lymphoid malignancies in a warm blooded animal such as man that is in need of such treatment which comprises administering an effective amount of a pharmaceutical composition which comprises a fumarate salt of a compound of formula (5a) with mannitol and dicalcium phosphate.

According to a further feature of the invention there is provided a method for treating cancer of the breast, colorectum, lung (including small cell lung cancer, non-small cell lung cancer and bronchioalveolar cancer) and prostate in a warm blooded animal such as man that is in need of such treatment which comprises administering an effective amount of a pharmaceutical composition which comprises a fumarate salt of a compound of formula (5a).

According to a further feature of the invention there is provided a method for treating cancer of the breast, colorectum, lung (including small cell lung cancer, non-small cell lung cancer and bronchioalveolar cancer) and prostate in a warm blooded animal such as man that is in need of such treatment which comprises administering an effective amount of a pharmaceutical composition which comprises a fumarate salt of a compound of formula (5a) with mannitol.

According to a further feature of the invention there is provided a method for treating cancer of the breast, colorectum, lung (including small cell lung cancer, non-small cell lung cancer and bronchioalveolar cancer) and prostate in a warm blooded animal such as man that is in need of such treatment which comprises administering an effective amount of a pharmaceutical composition which comprises a fumarate salt of a compound of formula (5a) with mannitol and dicalcium phosphate.

According to a further feature of the invention there is provided a method for treating cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas in a warm blooded animal such as man that is in need of such treatment which comprises administering an effective amount of a pharmaceutical composition which comprises a fumarate salt of a compound of formula (5a).

According to a further feature of the invention there is provided a method for treating cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas in a warm blooded animal such as man that is in need of such treatment which comprises administering an effective amount of a pharmaceutical composition which comprises a fumarate salt of a compound of formula (5a) with mannitol.

According to a further feature of the invention there is provided a method for treating cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas in a warm blooded animal such as man that is in need of such treatment which comprises administering an effective amount of a pharmaceutical composition which comprises a fumarate salt of a compound of formula (5a) with mannitol and dicalcium phosphate.

According to a further feature of the invention there is provided a method for treating lung cancer, prostate cancer, melanoma, ovarian cancer, breast cancer, endometrial cancer, kidney cancer, gastric cancer, sarcomas, head and neck cancers, tumours of the central nervous system and their metastases, and acute myeloid leukaemia in a warm blooded animal such as man that is in need of such treatment which comprises administering an effective amount of a pharmaceutical composition which comprises a fumarate salt of a compound of formula (5a).

According to a further feature of the invention there is provided a method for treating lung cancer, prostate cancer, melanoma, ovarian cancer, breast cancer, endometrial cancer, kidney cancer, gastric cancer, sarcomas, head and neck cancers, tumours of the central nervous system and their metastases, and acute myeloid leukaemia in a warm blooded animal such as man that is in need of such treatment which comprises administering an effective amount of a pharmaceutical composition which comprises a fumarate salt of a compound of formula (5a) with mannitol.

According to a further feature of the invention there is provided a method for treating lung cancer, prostate cancer, melanoma, ovarian cancer, breast cancer, endometrial cancer, kidney cancer, gastric cancer, sarcomas, head and neck cancers, tumours of the central nervous system and their metastases, and acute myeloid leukaemia in a warm blooded animal such as man that is in need of such treatment which comprises administering an effective amount of a pharmaceutical composition which comprises a fumarate salt of a compound of formula (5a) with mannitol and dicalcium phosphate.

As stated herein, the in vivo effects of a compound of formula (I) may be exerted in part by one or more metabolites that are formed within the human or animal body after administration of a pharmaceutical composition which comprises a fumarate salt of a compound of formula (5a).

As stated herein, the in vivo effects of a compound of formula (I) may be exerted in part by one or more metabolites that are formed within the human or animal body after administration of a pharmaceutical composition which comprises a fumarate salt of a compound of formula (5a) with mannitol.

As stated herein, the in vivo effects of a compound of formula (J) may be exerted in part by one or more metabolites that are formed within the human or animal body after administration of a pharmaceutical composition which comprises a fumarate salt of a compound of formula (5a) with mannitol and dicalcium phosphate.

The invention further relates to combination therapies wherein a pharmaceutical composition which comprises a fumarate salt of a compound of formula (5a) is administered concurrently or sequentially or as a combined preparation with another treatment of use in the control of oncology disease.

The invention further relates to combination therapies wherein a pharmaceutical composition which comprises a fumarate salt of a compound of formula (5a) with mannitol is administered concurrently or sequentially or as a combined preparation with another treatment of use in the control of oncology disease.

The invention further relates to combination therapies wherein a pharmaceutical composition which comprises a fumarate salt of a compound of formula (5a) with mannitol and dicalcium phosphate is administered concurrently or sequentially or as a combined preparation with another treatment of use in the control of oncology disease.

In particular, the treatment defined herein may be applied as a sole therapy or may involve, in addition to the compounds of the invention, conventional surgery or radiotherapy or chemotherapy. Accordingly, the compounds of the invention can also be used in combination with existing therapeutic agents for the treatment of cancer. Such therapeutic agents may include one or more of the following categories of anti-tumour agents:—

(i) other antiproliferative/antineoplastic drugs and combinations thereof, as used in medical oncology, such as alkylating agents (for example cis platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [Herceptin™], the anti-EGFR antibody panitumumab, the anti erbB 1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, ab1 kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies.

It is to be understood that the uses and methods of treatment described herein may use any of the compositions comprising a fumarate salt of a compound of formula (5a) described herein.

GENERAL EXPERIMENTAL

Figure 1:
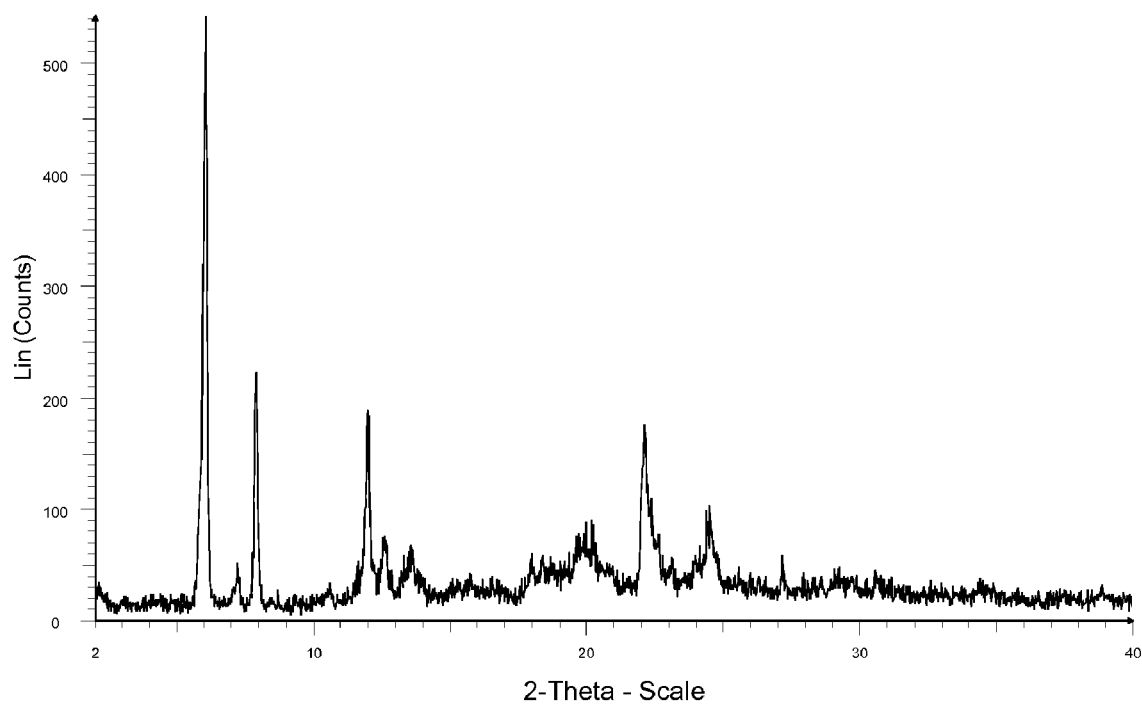
FIG. 1 demonstrates a powder X-ray diffraction pattern of (5-{2,4-bis[(3S)-3-methylmorpholin-4-yl]pyrido[2,3-d]pyrimidin-7-yl}-2-methoxyphenyl)methanol phosphate recorded by a Bruker D5000 diffractometer (wavelength of X-rays 1.5418 Å Cu source, Voltage 40 kV, filament emission 40 mA). Samples were scanned from 2-40° 2θ using a 0.02° step and a 1 second per step time count.

The invention will now be further explained by reference to the following illustrative examples.

The following abbreviations are used herein or within the following illustrative examples:—
HPLC High Performance Liquid Chromatography
GC Gas Chromatography
NMP N-methylpyrrolidin-2-one;
DMSO dimethylsulfoxide;
DMF N,N-dimethylformamide;
THF tetrahydrofuran;
MeOH methanol;
Bredereck's reagent; 1-tert-butoxy-N,N,N',N'-tetramethylmethanediamine
MeCN acetonitrile;
DCM dichloromethane;
DIPEA N,N-diisopropylethylamine;
MCC microcrystalline cellulose
DCPD dibasic calcium phosphate dihydrate
DCPA dibasic calcium phosphate anhydrous
SSG sodium starch glycolate
L-HPC low substitution hydroxypropylcellulose
SSF sodium stearyl fumarate
MgSt magnesium stearate
PVP polyvinylpyrrolidone (povidone)
HPC hydroxypropyl cellulose
RT room temperature (approximately 17 to 25° C.);
tR retention time;
m/z mass/charge ratio.
The chemical names were generated by software from ACD labs Version 9.0

Unless stated otherwise, starting materials were commercially available. All solvents and commercial reagents were of laboratory grade and were used as received.

Materials

TABLE 1

Materials: pharmacopeial status, function, grade and supplier

| Material | Pharmacopeia | Function | Example | Supplier |
|---|---|---|---|---|
| Mannitol | PhEur USP-NF JP | Filler (direct compression) Filler (wet granulation) | Parteck ™ M200 EMPROVE ® Pearlitol ™ 160C | Merck Chemicals Ltd. (UK) Roquette Freres S.A. (France) |
| Cellulose, microcrystalline | PhEur USP-NF JP | Filler (direct compression) Filler (wet granulation) | Avicel ® PH-102 Avicel ® PH-101 | FMC Biopolymer (Ireland) |
| Dibasic calcium phosphate dihydrate | PhEur USP-NF JP | Filler (direct compression) | Encompress ® | JRS Pharma Inc. (USA) |
| Dibasic calcium phosphate dihydrate | PhEur USP-NF JP | Filler (wet granulation) | Calipharm D ® | Innophos (USA) |
| Dibasic calcium phosphate anhydrous | PhEur USP-NF JP | Filler (direct compression) | Anhydrous Encompress ® | JRS Pharma Inc. (USA) |
| Dibasic calcium phosphate anhydrous | PhEur USP-NF JP | Filler (wet granulation) | Calipharm A ® | Innophos (USA) |
| Povidone | PhEur USP-NF JP | Binder | Plasdone ™ K29/32 | ISP Technologies, Inc. (USA) |
| Hydroxypropyl cellulose | PhEur USP-NF JP | Binder | Klucel ® EXF | Ashland, Inc. (USA) |
| Sodium starch glycolate | PhEur USP-NF | Disintegrant | Glycolys ® LV | Roquette Freres S.A. (France) |
| Low-substitution hydroxypropyl cellulose | USP-NF JP | Disintegrant | L-HPC LH-21 | Shin Etsu Chemical Co. Ltd. (Japan |
| Crospovidone | PhEur USP-NF | Disintegrant | Polyplasdone ® | International Specialty Products (USA) |
| Magnesium stearate | PhEur USP-NF JP | Lubricant | HyQual ® | Mallinckrodt Inc. (USA) |

TABLE 1-continued

Materials: pharmacopeial status, function, grade and supplier

| Material | Pharmacopeia | Function | Example | Supplier |
|---|---|---|---|---|
| Sodium stearyl fumarate | PhEur USP-NF | Lubricant | Pruv ™ | JRS Pharma Inc. (USA) |
| Polyvinyl alcohol | PhEur USP-NF, | Film former | Opadry ™ II Yellow[4] | Colorcon Limited (UK) |
| Titanium dioxide | PhEur USP-NF JP | Opacifier | | |
| Talc | PhEur USP-NF JP | Anti-tack agent | | |
| Iron oxide, yellow (Fe(OH)$_3$, goethite, CAS#20344-49-4) | | Pigment | | |
| Polyethylene glycol (Macrogol) | PhEur USP-NF JP | Plasticiser | | |

[1]PhEur: European Pharmacopoeia 6$^{th}$ Edition (Directorate for the Quality of Medicines of the Council of Europe) 2009.
[2]USP-NF: United States Pharmacopeia 31/National Formulary 26 (The United States Pharmacopeia Convention) 2008.
[3]JP: Japanese Pharmacopeia 15$^{th}$ Edition, English Version (Society of Japanese Pharmacopoeia) 2006.
[4]The film-coat may be supplied as a proprietary concentrate (eg, Opadry, product identifier 85F38196) or powder mixture that requires reconstitution in purified water, prior to application as an aqueous suspension to the tablet cores.

Hardness

Hardness testing was carried out using a Schleuniger Hardness Tester Model 6D or equivalent, in accordance with the procedure specified in the European Pharmacopoeia (Resistance to crushing of tablets), except that the number of tablets tested was as specified in the table. The hardness of each tablet was measured along its diameter. The average 'hardness' is reported in kiloponds (kp).

Disintegration Time

Disintegration time was measured out in accordance with the procedure specified in the European Pharmacopoeia, without a disc and using water as the medium. Disintegration time is reported in minutes (min.).

Compound Assay Test.

The Compound of Formula 5a, Aldehyde, and total impurities contents were determined using High Performance Liquid Chromatography HPLC. 5 µL sample was injected into a mobile phase comprising 0.1% trifluoroacetic acid in water (Eluent A)/0.1% trifluoroacetic acid in acetonitrile (Eluent B), as defined by the gradient program in Table 2 below.

The solution for the impurities determination is prepared by extraction from a known weight of 5 whole tablets using 1:1 acetonitrile:water as extraction solvent, followed by filtration through a 0.45 micron PVDF filter, such that the target concentration of Formula 5a fumarate in the test solution is 0.6 mg/mL.

TABLE 2

Gradient program - Compound Assay Test

| | Time (mins) | % A | % B |
|---|---|---|---|
| Gradient programme | 0 | 80 | 20 |
| | 16 | 70 | 30 |
| | 25 | 10 | 90 |
| | 26 | 80 | 20 |
| | 30 | 80 | 20 |

The mobile phase starts as 80% eluent A/20% eluent B at time zero, then the composition is modified gradually and linearly such that after 16 minutes the mobile phase comprises 70% eluent A and 30% eluent B. A steeper linear gradient is then applied such that after 26 minutes the mobile phase comprises 10% eluent A and 90% eluent B. Upon completion of data collection at 25 minutes, the eluent composition is adjusted to 80% eluent A/20% eluent B and held from 26 minutes to 30 minutes in order to re-equilibrate the column.

Separation of impurities was performed using a column 10 cm long×4.6 mm internal diameter packed with Thermo Scientific BetaBasic® C18 stationary phase having 3 µm particle size. The mobile phase flow rate was 0.75 mL/minute, temperature was controlled at 30° C., and impurity concentration was determined by comparison of absorbance at 245 nm, measured using a variable wavelength uv detector, with that of an external reference standard solution comprising Formula 5a free base.

Dissolution

Dissolution was determined according to the general procedure of the United States Pharmacopoeia (USP) using Apparatus 2 with 900 mL of 0.02 M sodium acetate buffer at pH 4.5 as dissolution medium and a stirrer speed of 75 rpm. At 15, 30 and 45 minutes, 10 ml of dissolution media was withdrawn and filtered through an unused 0.45 µm polypropylene filter. The amount of Formula 5a in solution was determined by uv spectroscopy at a wavelength of 365 nm against an external standard solution comprising Formula 5a free base.

Friability

Twenty tablets were accurately weighed and placed in a rotating drum (Copley TA-10 or equivalent). The drum was rotated 100 times and the tablets removed. Loose dust was removed from the tablets and the tablets re-weighed. The friability is expressed as the loss of mass and it is calculated as a percentage of the initial mass.

EXAMPLE 1

Pivalate Ester Route 5-acetyl-2-methoxybenzyl pivalate (1)

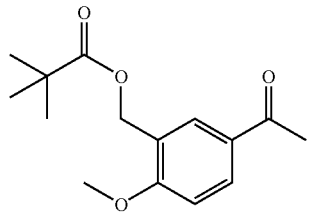

(1)

Pivalic acid (33.42 g, 327.2 mmol) was added to NMP (200 mL) and potassium carbonate (45.2 g, 327.2 mmol) at RT under an atmosphere of nitrogen. To the resulting suspension was added 1-[3-(chloromethyl)-4-methoxyphenyl]ethanone (50 g, 251.7 mmol) suspended in NMP (100 mL). Further NMP (50 mL) was added to the reaction vessel. The mixture was heated to 65° C. and held there for 120 minutes. Water (600 mL) was then added followed by toluene (400 mL). The resulting solution was allowed to settle and the upper organic layer retained. The lower aqueous layer was extracted with further toluene (200 mL) and the organic layers combined. The resulting organic layer was washed with water (250 mL) and concentrated in vacuo to afford a colourless oil (125 mL) containing the desired product (1) and toluene.

NMR Spectrum: $^1$H NMR (400.132 MHz, DMSO-d$_6$) δ 1.19 (9H, s), 2.52 (3H, s), 3.92 (3H, s) 5.12 (2H, s), 7.12-7.17 (1H, d), 7.88 (1H, d), 7.98 (1H, dd).

5-[(2E)-3-(dimethylamino)prop-2-enoyl]-2-methoxybenzyl pivalate (2)

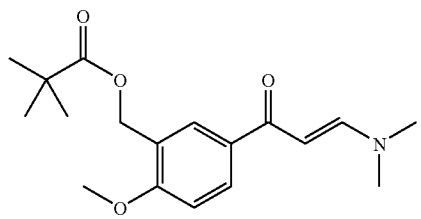

(2)

5-acetyl-2-methoxybenzyl pivalate (66.24 g, 251.7 mmol) was added to Bredereck's reagent (175.5 g, 1000.7 mmol) held under a nitrogen atmosphere. The resulting solution was heated at 54° C. for 240 minutes. Water (600 mL) was then added and the mixture allowed to stir for an hour. Methyl tert-butyl ether was then added (500 ml) and the mixture stirred and allowed to settle. The upper organic layer was separated off and retained. Further methyl-tert-butyl ether was then added (500 ml) and the mixture stirred and allowed to settle. The upper organic layer was separated off and combined with the original upper organic layer. The combined organic layers were washed twice with water (2×300 mL), discarding the two lower aqueous washes. Solvent (850 mL) is removed from the reaction by atmospheric distillation and iso-hexane (100 mL) added. The clear solution was allowed to cool to 20° C. whereby a white, crystalline solid was obtained. Further iso-hexane (50 mL) was added and the solid filtered off at around 20° C. The solid was washed twice with fresh iso-hexane (2×100 mL) and dried to constant weight to afford 64 g of the desired 5-[(2E)-3-(dimethylamino)prop-2-enoyl]-2-methoxybenzyl pivalate (2).

NMR Spectrum: $^1$H NMR (400.132 MHz, DMSO-d$_6$) δ 1.19 (9H, s), 2.8-3.0 (3H, broad s), 3.0-3.2 (3H, broad s), 3.88 (3H, s), 5.11 (2H, s), 5.74-5.83 (1H, d), 7.05-7.09 (1H, d), 7.6-7.7 (1H, d), 7.84 (1H, d), 7.90 (1H, dd)

M.pt. 82-84° C.

5-(2,4-dioxo-1,2,3,4-tetrahydropyrido[2,3-d]pyrimidin-7-yl)-2-methoxybenzyl pivalate (3)

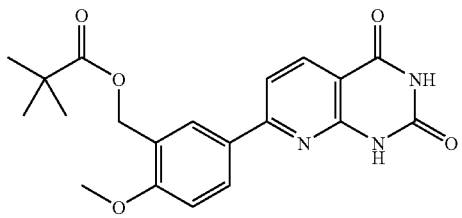

(3)

6-Aminouracil (2.50 g, 19.1 mmol) was added to glacial acetic acid (24.6 mL) and water (6.1 mL) and the mixture heated to 99° C. A solution of 5-[(2E)-3-(dimethylamino)prop-2-enoyl]-2-methoxybenzyl pivalate (3.1 g, 9.5 mmol) in DMSO (9.2 mL) was then added over 280 minutes. The reaction was stirred at 99° C. for a further 50 minutes and cooled to 0° C. A solution of potassium hydroxide (24 g, 363.6 mmol) in water (48 mL) was then added to achieve a pH of around 7.0. Aqueous potassium carbonate was then added to afford a pH of around 10. After an hour at RT, a beige solid was filtered off, washed three times with aqueous potassium carbonate and pulled visibly dry on the filter. The beige solid was then added to a solution of citric acid (7.1 g) in water (44 ml) and the mixture maintained at 20° C. for 60 minutes. The resulting creamy white solid was isolated by filtration and washed with water until neutral pH of the wash liquors was obtained. The solid was dried to constant weight in vacuo thus affording 3.34 g of desired product (3).

NMR Spectrum: $^1$H NMR (500.132 MHz, DMSO-d$_6$) δ 1.19 (9H, s), 3.92 (3H, s), 5.14 (2H, s), 7.31-7.34 (1H, d), 7.79-7.82 (1H, d), 8.26-8.29 (1H, d), 8.31-8.35 (1H, dd), 8.48 (1H, d), 11.41 (1H, broad s), 11.67 (1H, broad s).

M.pt. 260-266° C.

5-(2,4-dioxo-1,2,3,4-tetrahydropyrido[2,3-d]pyrimidin-7-yl)-2-methoxybenzyl pivalate (3) (Alternate method)

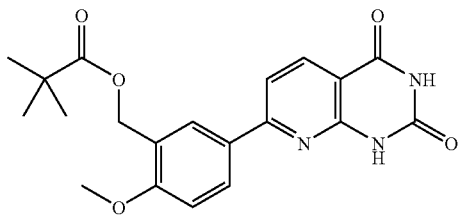

(3)

6-Aminouracil (2.69 g, 22.5 mmol) was added to glacial acetic acid (55.2 mL) and water (13.8 mL) and the mixture heated to 95° C. A solution of 5-[(2E)-3-(dimethylamino)prop-2-enoyl]-2-methoxybenzyl pivalate (6.25 g, 18.79 mmol) in DMSO (18 mL) was then added over 240 minutes. After 25% of the solution was added (approximately 60 minutes) seed crystals of 5-(2,4-dioxo-1,2,3,4-tetrahydropyrido [2,3-d]pyrimidin-7-yl)-2-methoxybenzyl pivalate were added to initiate crystallisation. After complete addition of the DMSO solution, the reaction mixture was maintained at 95° C. for a further hour then cooled gradually to 60° C. After 60 minutes at 60° C., the desired product was obtained by filtration and washed with water followed by acetonitrile. The solid was dried to constant weight in vacuo thus affording 6.82 g of desired product (3).

NMR Spectrum: ¹H NMR (500.132 MHz, DMSO-$d_6$) δ 1.19 (9H, s), 3.92 (3H, s), 5.14 (2H, s), 7.31-7.34 (1H, d), 7.79-7.82 (1H, d), 8.26-8.29 (1H, d), 8.31-8.35 (1H, dd), 8.48 (1H, d), 11.41 (1H, broad s), 11.67 (1H, broad s).

M.pt. 260-266° C.

5-(2,4-dichloropyrido[2,3-d]pyrimidin-7-yl)-2-methoxybenzyl pivalate (4)

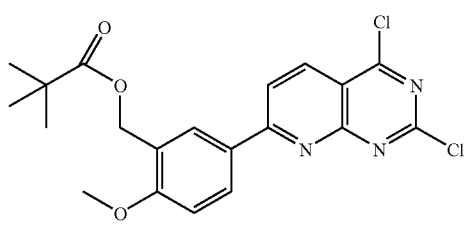

(4)

5-(2,4-dioxo-1,2,3,4-tetrahydropyrido[2,3-d]pyrimidin-7-yl)-2-methoxybenzyl pivalate (5.20 g, 13.29 mmol) was stirred with DIPEA (4.29 g, 33.23 mmol) and methoxybenzene (52 mL). Phosphorus oxychloride (6.11 g, 39.87 mmol) was then added and the mixture stirred at RT for 60 minutes. The mixture was then heated to 80° C. After 180 minutes, water (24 mg, 1.33 mmol) was added and the solution cooled to 5° C. HPLC analysis showed the desired reaction to be complete. Ethyl acetate (26 ml) was then added followed by aqueous dipotassium hydrogen phosphate solution (26 ml, 2.0 mol $L^{-1}$). The resulting yellow solid was isolated by filtration and dried visibly dry on the filter. The yellow solid was then added to a fresh reaction vessel and aqueous dipotassium hydrogen phosphate solution (26 ml, 2.0 mol $L^{-1}$) added followed by ethyl acetate (10.4 ml). The resulting yellow solid was isolated by filtration and washed with fresh ethyl acetate (10 ml). The resulting solid was isolated by filtration and dried to constant weight in vacuo at 70° C. affording 6.7 g of 5-(2,4-dichloropyrido[2,3-d]pyrimidin-7-yl)-2-methoxybenzyl pivalate (4). The structure of the desired compound was confirmed by ¹H NMR analysis.

NMR Spectrum: ¹H NMR (400.132 MHz, DMSO-$d_6$) δ 1.20 (9H, s), 3.95 (3H, s), 5.20 (2H, s) 7.27-7.32 (1H, d), 8.36-8.44 (2H, m), 8.44-8.49 (1H, d), 8.69-8.74 (1H, d).

M.pt. 202-207° C.

5-(2,4-dichloropyrido[2,3-d]pyrimidin-7-yl)-2-methoxybenzyl pivalate (4). (Alternate Method)

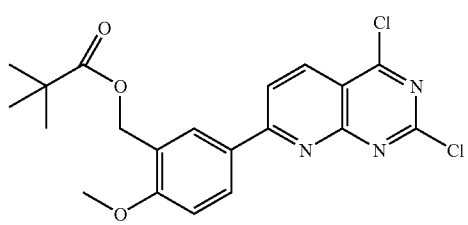

(4)

5-(2,4-dioxo-1,2,3,4-tetrahydropyrido[2,3-d]pyrimidin-7-yl)-2-methoxybenzyl pivalate prepared by the alternate method (6.95 g, 18.1 mmol) was stirred with DIPEA (6.8 g, 52.7 mmol) and toluene (55.6 mL). Phosphorus oxychloride (8.1 g, 52.7 mmol) was then added and the mixture stirred at RT for 60 minutes. The mixture was then heated to 80° C. over 120 minutes. After 140 minutes at 80° C., water (0.16 g, 9.0 mmol) was added and the reaction mixture monitored by HPLC. HPLC analysis showed the desired reaction to be complete. Tetrahydrofuran (13.9 mL) was then added and the solution cooled to 5° C. The resulting yellow solid was isolated by filtration, washed with fresh tetrahydrofuran (13.9 mL) and dried visibly dry on the filter. The resulting solid was further dried to constant weight in vacuo at 70° C. affording 6.55 g of 5-(2,4-dichloropyrido[2,3-d]pyrimidin-7-yl)-2-methoxybenzyl pivalate (4). The structure of the desired compound was confirmed by ¹H NMR analysis.

NMR Spectrum: ¹H NMR (400.132 MHz, DMSO-$d_6$) δ 1.20 (9H, s), 3.95 (3H, s), 5.20 (2H, s) 7.27-7.32 (1H, d), 8.36-8.44 (2H, m), 8.44-8.49 (1H, d), 8.69-8.74 (1H, d).

M.pt. 202-207° C.

5-{2,4-bis[(3S)-3-methylmorpholin-4-yl]pyrido[2,3-d]pyrimidin-7-yl}-2-methoxybenzyl pivalate (5)

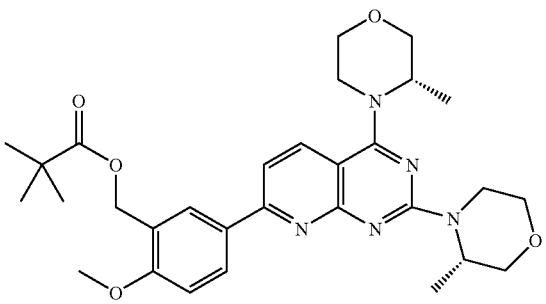

(5)

5-(2,4-dichloropyrido[2,3-d]pyrimidin-7-yl)-2-methoxybenzyl pivalate (1.1 g, 2.49 mmol) was added to toluene (5.50 mL) and DIPEA (0.321 g, 2.49 mmol). (3S)-3-methylmorpholine (0.755 g, 7.46 mmol) was then added and the mixture heated to 50° C. After heating at 50° C. for 10 minutes, the reaction was then further heated to 110° C. After 480 minutes, HPLC analysis showed the desired reaction to be complete. The reaction was cooled to RT and water (5.5 mL) added followed by ethyl acetate (3.3 ml). Upon separation of the lower aqueous layer, 2-methylpentane (7.7 mL) was added dropwise at 60° C. to the ethyl acetate extract. On addition of further 2-methylpentate (3.3 mL) a bright yellow solid was given. The resulting solid was filtered off at RT and washed with fresh 2-methylpentane (3.3 mL) to afford 1.08 g of a yellow solid that upon NMR analysis was consistent with the desired compound (5).

NMR Spectrum: ¹H NMR (500.132 MHz, CDCl₃) δ 1.24 (9H, s), 1.35 (3H, d), 1.46 (3H, d), 3.37 (1H, m), 3.56 (1H, m), 3.64-4.02 (9H, m), 3.90 (3H, s), 4.30-4.40 (1H, m), 4.57-4.69 (1H, m), 4.93 (1H, broad s), 5.22 (2H, s), 7.00 (1H, d), 7.42 (1H, d), 7.98 (1H, d), 8.12 (1H, d), 8.22 (1H, dd).

M.pt. 107-110° C.

5-{2,4-bis[(3S)-3-methylmorpholin-4-yl]pyrido[2,3-d]pyrimidin-7-yl}-2-methoxybenzyl pivalate (5) (Alternate Method)

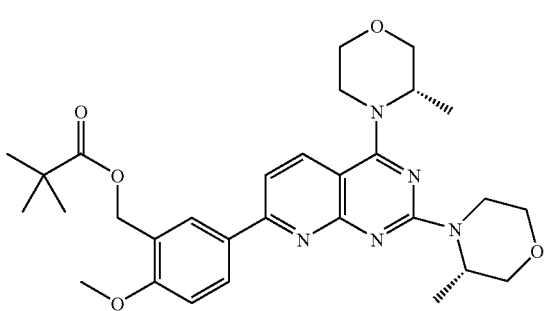

(5)

5-(2,4-dichloropyrido[2,3-d]pyrimidin-7-yl)-2-methoxybenzyl pivalate (15.1 g, 35.6 mmol) prepared by the alternate method was added to toluene (60.0 mL) and potassium carbonate (10.0 g, 71.2 mmol). (3S)-3-methylmorpholine (8.4 g, 81.8 mmol) was then added and the mixture heated to 110° C. After heating at 110° C. for 16 hours, HPLC analysis showed the desired reaction to be complete. The reaction mixture was cooled to 60° C. and fresh toluene (30 mL) added. Water (45 mL) was added and the mixture allowed to stir and subsequently settle. Upon separation of the lower aqueous layer, 2-methylpentane (150 mL) was added dropwise at 60° C. to the upper toluene extract. Seed crystals of the desired compound were then added (40 mg, 71 μmol) and the reaction mixture cooled steadily to 20° C. The resulting solid was filtered off at 20° C. and washed with fresh 2-methylpentane (2×45 mL) to afford 17.2 g of a yellow solid that upon NMR analysis was consistent with the desired compound (5).

NMR Spectrum: $^1$H NMR (500.132 MHz, CDCl$_3$) δ 1.24 (9H, s), 1.35 (3H, d), 1.46 (3H, d), 3.37 (1H, m), 3.56 (1H, m), 3.64-4.02 (9H, m), 3.90 (3H, s), 4.30-4.40 (1H, m), 4.57-4.69 (1H, m), 4.93 (1H, broad s), 5.22 (2H, s), 7.00 (1H, d), 7.42 (1H, d), 7.98 (1H, d), 8.12 (1H, d), 8.22 (1H, dd).

M.pt. 107-110° C.

(5-{2,4-bis[(3S)-3-methylmorpholin-4-yl]pyrido[2,3-d]pyrimidin-7-yl}-2-methoxyphenyl)methanol (6)

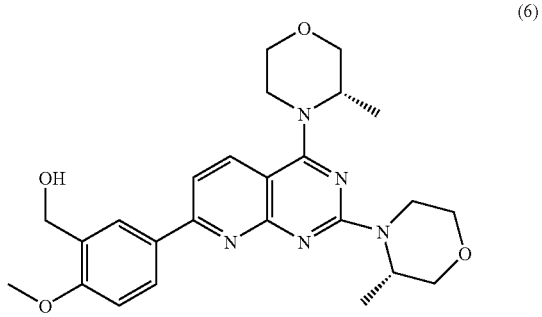

(6)

Potassium hydroxide solution (1.7 mL, 3.10 mmol) was added to a solution of 5-{2,4-bis[(3S)-3-methylmorpholin-4-yl]pyrido[2,3-d]pyrimidin-7-yl}-2-methoxybenzyl pivalate (172 mg, 0.30 mmol) in THF (6.9 mL) and methanol (1.7 mL) at RT under an atmosphere of nitrogen. After 240 minutes, HPLC analysis showed complete disappearance of the starting material. The reaction was maintained at RT overnight (for convenience) and aqueous citric acid (20% w/v, 2 mL) was added followed by methylene chloride (15 mL). The upper aqueous layer was extracted with two further extractions of methylene chloride (2×15 mL) and the organic layers combined. Evaporation of the methylene chloride afforded (5-{2,4-bis[(3S)-3-methylmorpholin-4-yl]pyrido[2,3-d]pyrimidin-7-yl}-2-methoxyphenyl)methanol (6) as a yellow solid (133 mg).

NMR Spectrum: $^1$H NMR (400.132 MHz, DMSO-d$_6$) δ 1.23-1.28 (3H, d), 1.35-1.40 (3H, d), 3.14-3.27 (1H, m), 3.40-3.50 (1H, m), 3.55-3.79 (6H, m), 3.87 (3H, s) 3.84-3.97 (3H, m), 4.38-4.47 (2H, m), 4.58 (2H, s), 4.74-4.81 (1H, m), 5.19 (1H, broad s), 7.08-7.13 (1H, d), 7.56-7.63 (1H, d), 8.05-8.09 (1H, dd), 8.12-8.16 (1H, d), 8.32 (1H, d).

M.pt. 202-205° C.

(5-{2,4-bis[(3S)-3-methylmorpholin-4-yl]pyrido[2,3-d]pyrimidin-7-yl}-2-methoxyphenyl)methanol (6) (Alternate Method)

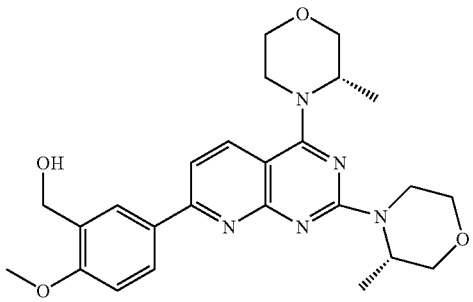

(6)

Potassium hydroxide solution (9.96 mL, 133.20 mmol) was added over 30 minutes to a solution of 5-{2,4-bis[(3S)-3-methylmorpholin-4-yl]pyrido[2,3-d]pyrimidin-7-yl}-2-methoxybenzyl pivalate prepared by the alternate method (25.16 g, 0.30 mmol) in methanol (244 mL) at 50° C. under an atmosphere of nitrogen. After 120 minutes at 50° C., HPLC analysis showed complete disappearance of the starting material. Seed crystals of the desired compound were then added (122 mg, 257 μmol) and the reaction was maintained at 50° C. for 2 hours to establish crystallisation of the desired product. Water, (244 mL) is then added over 15 minutes maintaining a reaction temperature of 50° C. The reaction mixture is then cooled to 20° C. and the resulting yellow solid isolated by filtration. The yellow solid was washed with water (3×97 mL) and dried initially in air and then in vacuo at 45° C. to give (5-{2,4-bis[(3S)-3-methylmorpholin-4-yl]pyrido[2,3-d]pyrimidin-7-yl}-2-methoxyphenyl)methanol (6) as a yellow solid (19.33 g).

NMR Spectrum: $^1$H NMR (400.132 MHz, DMSO-d$_6$) δ 1.23-1.28 (3H, d), 1.35-1.40 (3H, d), 3.14-3.27 (1H, m), 3.40-3.50 (1H, m), 3.55-3.79 (6H, m), 3.87 (3H, s) 3.84-3.97 (3H, m), 4.38-4.47 (2H, m), 4.58 (2H, s), 4.74-4.81 (1H, m), 5.19 (1H, broad s), 7.08-7.13 (1H, d), 7.56-7.63 (1H, d), 8.05-8.09 (1H, dd), 8.12-8.16 (1H, d), 8.32 (1H, d).

M.pt. 202-205° C.

EXAMPLE 2

Methyl Ester Route

Methyl 5-acetyl-2-methoxybenzoate (7)

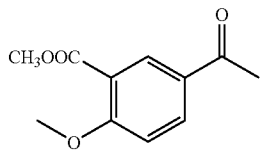

(7)

Methyl 5-acetyl-2-hydroxybenzoate (95.3 g, 490.6 mmol) was added to DMF (381 mL) and potassium carbonate (82.2 g, 588.8 mmol) at RT under an atmosphere of nitrogen. To the resulting suspension was added methyl iodide (90.5 g, 637.8 mmol) whilst maintaining good agitation. After stirring at RT for 30 minutes, the crude reaction mixture was analysed by GC demonstrating complete reaction. Water (380 mL) was added followed by further water (380 mL) and the resulting white solid filtered off to afford 82.5 g of the desired, water wet product (7).

NMR Spectrum: $^1$H NMR (400.132 MHz, CDCl$_3$) δ 2.60 (3H, s), 3.92 (3H, s), 3.98 (3H, s), 7.03-7.05 (1H, d), 8.10-8.13 (1H, dd), 8.40 (1H, d).

M.pt. 93-94° C.

Methyl 5-[(2E)-3-(dimethylamino)prop-2-enoyl]-2-methoxybenzoate (8)

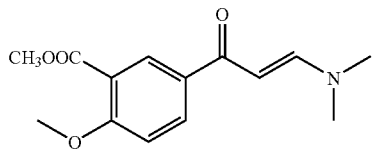

(8)

Methyl 5-acetyl-2-methoxybenzoate (11.98 g, 48.0 mmol) was added to N,N-dimethylformamide dimethyl acetal (44.6 g, 374.5 mmol) held under a nitrogen atmosphere. The resulting solution was heated at 95° C. for 60 minutes. Methanol (10 ml) was then removed by atmospheric distillation and further N,N-dimethylformamide dimethyl acetal (8.90 g, 74.9 mmol) added. The resulting solution was heated at 95° C. for a further 270 minutes. The reaction was then cooled to 50° C. and ethyl acetate (35 mL) added. Solvent (35 mL) is removed from the reaction by atmospheric distillation and fresh ethyl acetate (35 mL) added. Further solvent (35 mL) is removed from the reaction by atmospheric distillation and fresh ethyl acetate (50 mL) added. The reaction mixture is cooled to RT whereby the desired product crystallises out as a granular, free flowing solid. The solid was isolated by filtration, washed twice with fresh ethyl acetate (2×30 mL) and dried to constant weight to afford 11.39 g of the desired methyl 5-[(2E)-3-(dimethylamino)prop-2-enoyl]-2-methoxybenzoate (8).

NMR Spectrum: $^1$H NMR (400.132 MHz, DMSO-d$_6$) δ 2.93 (3H, broad s), 3.15 (3H, broad s), 3.81 (3H, s), 3.89 (3H, s), 5.79-5.84 (1H, d), 7.15-7.22 (1H, d), 7.67-7.75 (1H, d), 8.07-8.12 (1H, dd), 8.17 (1H, d).

M.pt. 112-114° C.

Methyl 5-(2,4-dioxo-1,2,3,4-tetrahydropyrido[2,3-d]pyrimidin-7-yl)-2-methoxybenzoate (9)

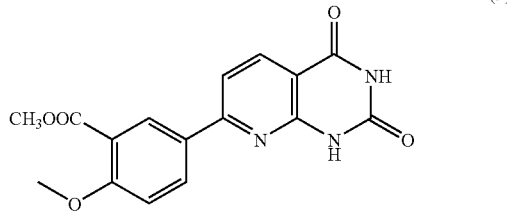

(9)

6-Aminouracil (14.32 g, 112.7 mmol) was added to glacial acetic acid (112.5 mL) and water (75 mL) and the mixture heated to 99° C. A solution of methyl 5-[(2E)-3-(dimethylamino)prop-2-enoyl]-2-methoxybenzoate (15 g, 56.3 mmol) in DMSO (75 mL) was then added over 180 minutes. The reaction was stirred at 99° C. for a further 90 minutes and cooled to 60° C. Water (75 mL) was then added and the reaction maintained at 60° C. for a further 60 minutes and then filtered off to afford a beige solid. The solid was washed with fresh water (75 mL) and dried visibly dry thus affording 19.6 g of water wet solid (9).

NMR Spectrum: $^1$H NMR (400.132 MHz, DMSO-d$_6$) δ 3.84 (3H, s), 3.92 (3H, s), 7.31-7.34 (1H, d), 7.79-7.82 (1H, d), 8.26-8.29 (1H, d), 8.31-8.35 (1H, dd), 8.48 (1H, d), 11.41 (1H, broad s), 11.67 (1H, broad s).

M.pt. 301-303° C.

Methyl 5-(2,4-dichloropyrido[2,3-d]pyrimidin-7-yl)-2-methoxybenzoate (10)

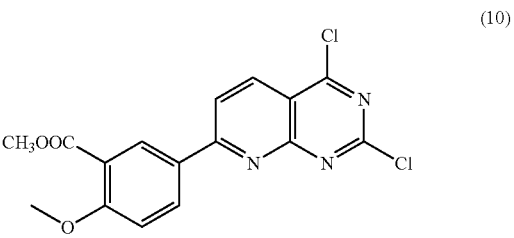

(10)

Methyl 5-(2,4-dioxo-1,2,3,4-tetrahydropyrido[2,3-d]pyrimidin-7-yl)-2-methoxybenzoate (0.5 g, 1.5 mmol) was stirred with DIPEA (0.426 g, 3.29 mmol) and toluene (2.5 mL). Phosphorus oxychloride (1.15 g, 7.5 mmol) was then added and the mixture heated to 80° C. After 180 minutes, HPLC analysis showed the reaction to be complete. The reaction was cooled to RT and all volatile components removed by distillation in vacuo to afford 1.43 g of an oil that upon NMR analysis contained 31% by weight of the desired compound (10).

NMR Spectrum: ¹H NMR (400.132 MHz, CDCl₃) δ 3.95 (3H, s), 4.03 (3H, s), 7.15-7.19 (1H, d), 8.14-8.18 (1H, d), 8.55-8.59 (1H, dd), 8.58-8.61 (1H, d), 8.75 (1H, d).

Methyl 5-{2,4-bis[(3S)-3-methylmorpholin-4-yl]pyrido[2,3-d]pyrimidin-7-yl}-2-methoxybenzoate (11)

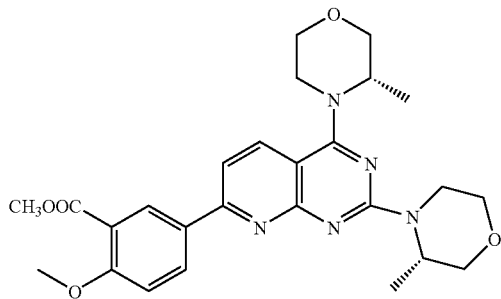

(11)

Methyl 5-(2,4-dichloropyrido[2,3-d]pyrimidin-7-yl)-2-methoxybenzoate (0.37 g, 0.315 mmol) was added to anisole (1.85 mL), (3S)-3-methylmorpholine (0.095 g, 0.945 mmol) and catalytic quantities of glacial acetic acid at RT. The reaction was then heated to 130° C. After 270 minutes, HPLC analysis showed the desired reaction to be complete. The reaction was cooled to RT and saturated aqueous citric acid solution (3 mL) added followed by ethyl acetate (7.5 ml). Upon separation of the two layers, further saturated aqueous citric acid solution (4 mL) was added to the upper ethyl acetate layer. The combined aqueous citric acid solutions were then washed with fresh ethyl acetate (7.4 mL). Upon separation of the unwanted upper (ethyl acetate) phase, the lower aqueous phase was treated with aqueous sodium hydroxide (0.25 mL, 3.15 mmol). The resulting solution was extracted twice with fresh ethyl acetate (2×7.5 mL) and the organic layers combined and dried over anhydrous magnesium sulphate (3 g). Ethyl acetate was then removed by distillation in vacuo to afford 0.19 g of a yellow oil that upon NMR analysis contained 71% by weight of the desired compound (11).

NMR Spectrum: ¹H NMR (400.132 MHz, DMSO-d₆) δ 1.23-1.28 (3H, d), 1.35-1.40 (3H, d), 3.17-3.27 (1H, m), 3.40-3.50 (1H, m), 3.55-3.99 (9H, m), 3.87 (3H, s), 3.93 (3H, s), 4.38-4.47 (2H, m), 4.74-4.81 (1H, m), 7.28-7.35 (1H, d), 7.61-7.66 (1H, d), 8.15-8.19 (1H, d), 8.32-8.36 (1H, dd), 8.56 (1H, d).

M.pt. 97-101° C.

(5-{2,4-bis[(3S)-3-methylmorpholin-4-yl]pyrido[2,3-d]pyrimidin-7-yl}-2-methoxyphenyl)methanol (6)

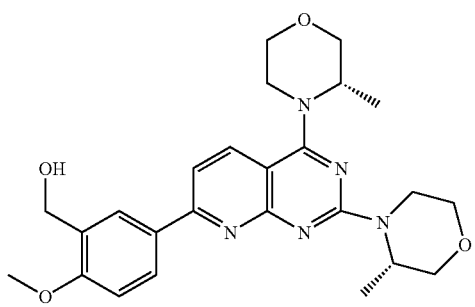

(6)

A solution of lithium aluminium hydride (2M solution in THF, 1.01 mL, 2.01 mmol) was added to a solution of methyl 5-{2,4-bis[(3S)-3-methylmorpholin-4-yl]pyrido[2,3-d]pyrimidin-7-yl}-2-methoxybenzoate (1.47 g, 2.68 mmol) in THF (19.8 mL) at 0° C. under an atmosphere of nitrogen. After 60 minutes, further lithium aluminium hydride (2M solution in THF, 0.67 mL, 1.34 mmol) was added and the solution allowed to stir at RT for 900 minutes. The resulting solution was quenched by the addition of water (11.76 mL) and extracted with ethyl acetate (22 mL). On evaporation of the ethyl acetate, 1.2 g of (5-{2,4-bis[(3S)-3-methylmorpholin-4-yl]pyrido[2,3-d]pyrimidin-7-yl}-2-methoxyphenyl)methanol (6) is obtained as a yellow solid.

NMR Spectrum: ¹H NMR (400.132 MHz, DMSO-d₆) δ 1.23-1.28 (3H, d), 1.35-1.40 (3H, d), 3.14-3.27 (1H, m), 3.40-3.50 (1H, m), 3.55-3.79 (6H, m), 3.87 (3H, s) 3.84-3.97 (3H, m), 4.38-4.47 (2H, m), 4.58 (2H, s), 4.74-4.81 (1H, m), 5.19 (1H, broad s), 7.08-7.13 (1H, d), 7.56-7.63 (1H, d), 8.05-8.09 (1H, dd), 8.12-8.16 (1H, d), 8.32 (1H, d).

EXAMPLE 3

Preparation of Salts

EXAMPLE 3

(5-{2,4-Bis[(3S)-3-methylmorpholin-4-yl]pyrido[2,3-d]pyrimidin-7-yl}-2-methoxyphenyl)methanol Diphosphate

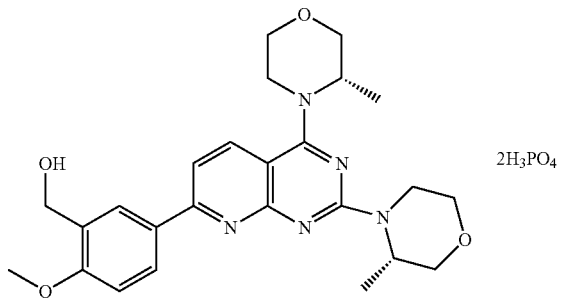

(5-{2,4-Bis[(3S)-3-methylmorpholin-4-yl]pyrido[2,3-d]pyrimidin-7-yl}-2-methoxyphenyl)methanol (1.50 g, 3.2 mmoles), phosphoric acid (0.78 g, 6.8 mmoles) and methylated spirit industrial 74 O.P. (15.0 ml) were charged to a 100 ml reactor and heated to reflux. On cooling in stages product solidified. Product was isolated, washed with methylated spirit industrial 74 O.P. and dried in vacuum oven at 50 C to yield 1.81 g of (5-{2,4-Bis[(3S)-3-methylmorpholin-4-yl]pyrido[2,3-d-]pyrimidin-7-yl}-2-methoxyphenyl)methanol Diphosphate as a yellow solid.

NMR Spectrum: ¹H NMR (400.132 MHz, DMSO-d₆): δ 1.28-1.36 (3H, d), 1.45-1.55 (3H, d), 3.33-4.01 (13H, m), 4.23 (1H, d), 4.30 (1H, d), 4.59 (2H, s), 4.72-4.80 (2H, broad m), 7.15 (1H, d), 7.84 (1H, d), 8.12 (1H, dd), 8.33 (1H, s), 8.35 (1H, d).

EXAMPLE 3a(i)

(5-{2,4-Bis[(3S)-3-methylmorpholin-4-yl]pyrido[2,3-d]pyrimidin-7-yl}-2-methoxyphenyl)methanol phosphate On a 50 mg scale using a 1:1.1 molar ratio of (5-{2,4-Bis[(3S)-3-methylmorpholin-4-yl]pyrido[2,3-d]pyrimidin-7-yl}-2-methoxyphenyl)methanol:Phosphoric acid. 50 mg of (5-{2,4-Bis[(3S)-3-methylmorpholin-4-yl]pyrido[2,3-d]pyrimidin-7-yl}-2-methoxyphenyl)methanol was dissolved in the minimal amount of MeCN, this solution was then added drop-wise to a vial containing the phosphoric acid which caused a yellow solid to immediately precipitate. The experiment was then left to stir over night at room temperature before filtering and isolating the precipitate.

A powder X-ray diffraction pattern was recorded using a Bruker D5000 diffractometer (wavelength of X-rays 1.5418 Å Cu source, Voltage 40 kV, filament emission 40 mA). Samples were scanned from 2-40° 2θ using a 0.02° step and a 1 second per step time count. (see FIG. 1)

Peaks were observed at:

| Angle/ °2θ (λ = 1.5418 Å) | d-spacing/Å | Relative Intensity/% |
|---|---|---|
| 5.99 | 14.74 | 100 |
| 7.87 | 11.23 | 40.9 |
| 7.18 | 12.31 | 9.4 |
| 11.97 | 7.39 | 34.4 |
| 12.60 | 7.02 | 13.6 |
| 13.55 | 6.53 | 12.3 |
| 22.11 | 4.02 | 32.2 |
| 24.49 | 3.63 | 18.8 |

EXAMPLE 3a(ii)

(5-{2,4-Bis[(3S)-3-methylmorpholin-4-yl]pyrido[2,3-d]pyrimidin-7-yl}-2-methoxyphenyl)methanol phosphate On a 50 mg scale using a 1:1.1 molar ratio of (5-{2,4-Bis[(3S)-3-methylmorpholin-4-yl]pyrido[2,3-d]pyrimidin-7-yl}-2-methoxyphenyl)methanol:Phosphoric acid. 50 mg of (5-{2,4-Bis[(3S)-3-methylmorpholin-4-yl]pyrido[2,3-d]pyrimidin-7-yl}-2-methoxyphenyl)methanol was dissolved in the minimal amount of Ethyl Acetate, this solution was then added drop-wise to a vial containing the phosphoric acid which caused a yellow solid to immediately precipitate. The experiment was then left to stir over night at room temperature before filtering and isolating the precipitate.

Powder X-ray diffraction indicated that the material was amorphous.

EXAMPLE 3b (5-{2,4-Bis[(3S)-3-methylmorpholin-4-yl]pyrido[2,3-d]pyrimidin-7-yl}-2-methoxyphenyl)methanol D-Tartrate

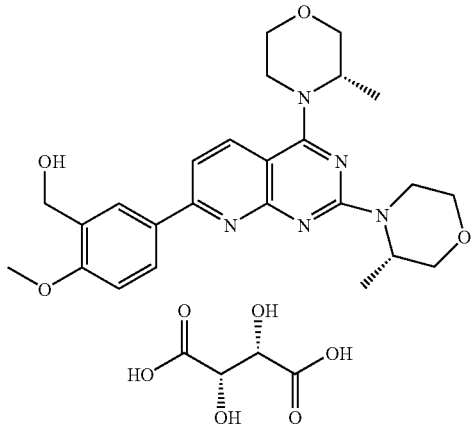

(5-{2,4-Bis[(3S)-3-methylmorpholin-4-yl]pyrido[2,3-d]pyrimidin-7-yl}-2-methoxyphenyl)methanol (1.50 g (96% w/w, 3.1 mmoles), D-tartaric Acid (0.51 g, 3.4 mmoles) and methylated spirit industrial 74 O.P. (15.0 ml) were charged to a 100 ml reactor and heated to reflux. Product began to precipitate. On cooling more product precipitated. Product was isolated, washed with methylated spirit industrial 74 O.P. and dried in vacuum oven at 50 C for 4 h to yield 1.98 g of (5-{2,4-Bis[(3S)-3-methylmorpholin-4-yl]pyrido[2,3-d]pyrimidin-7-yl}-2-methoxyphenyl)methanol D-Tartrate as a yellow solid.

NMR Spectrum: $^1$H NMR (400.132 MHz, DMSO-$d_6$) δ 1.22-1.26 (3H, d), 1.34-1.39 (3H, d), 3.14-4.00 (19H, overlapping m), 4.30 (2H, s), 4.40 (1H, d), 4.57 (2H, s), 4.72-4.80 (1H, broad), 5.11-5.23 (1H, broad), 7.09 (1H, d), 7.60 (1H, d), 8.05 (1H, dd), 8.16 (1H, d), 8.31 (1H, s).

M.pt: Begins to decompose from about 128° C. onwards forming a resin.

Figure 2:
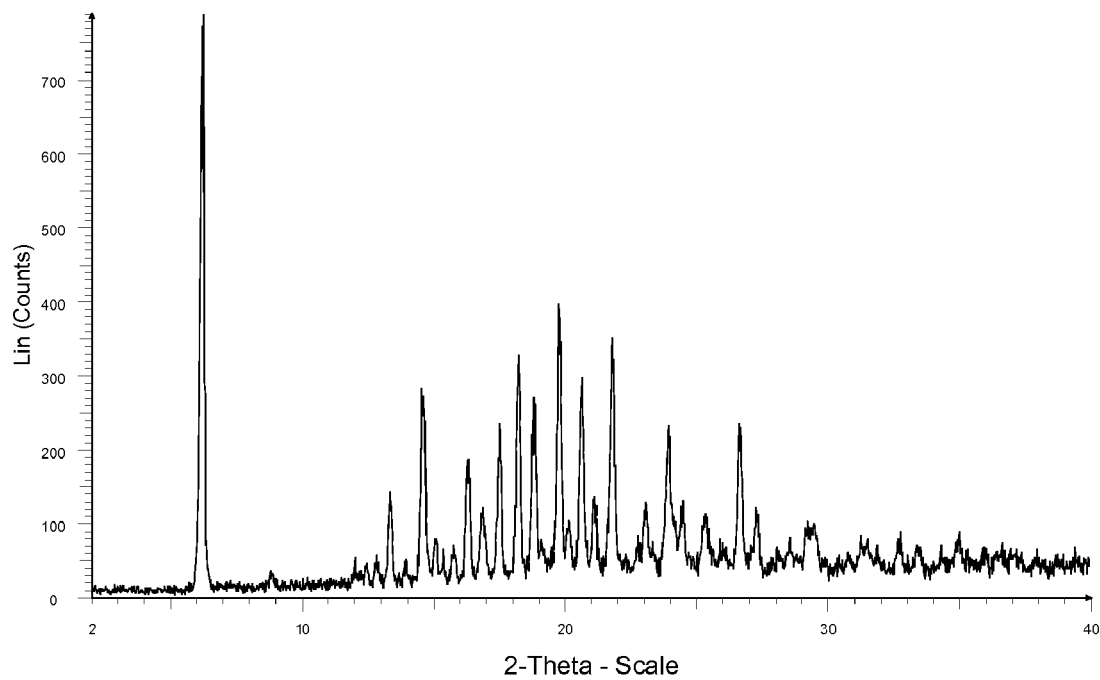
FIG. 2 demonstrates a powder X-ray diffraction pattern of (5-{2,4-bis[(3S)-3-methylmorpholin-4-yl]pyrido[2,3-d]pyrimidin-7-yl}-2-methoxyphenyl)methanol D-tartrate recorded by a Bruker D5000 diffractometer (wavelength of X-rays 1.5418 Å Cu source, Voltage 40 kV, filament emission 40 mA). Samples were scanned from 2-40° 2θ using a 0.02° step and a 1 second per step time count.

A powder X-ray diffraction patterns was recorded using a Bruker D5000 diffractometer (wavelength of X-rays 1.5418 Å Cu source, Voltage 40 kV, filament emission 40 mA). Samples were scanned from 2-40° 2θ using a 0.02° step and a 1 second per step time count. (see FIG. 2)

Peaks were observed at:

| Angle/ °2θ (λ = 1.5418 Å) | d-spacing/Å | Relative Intensity/% |
|---|---|---|
| 6.17 | 14.31 | 100.0 |
| 13.33 | 6.63 | 17.8 |
| 14.58 | 6.07 | 34.4 |
| 16.29 | 5.43 | 23.5 |
| 17.50 | 5.06 | 29.6 |
| 18.20 | 4.87 | 39.7 |
| 18.80 | 4.71 | 34.1 |
| 19.76 | 4.49 | 50.2 |
| 20.63 | 4.30 | 37.5 |

TGA was recorded using a TA Instrument TGA, Q5000 series. Typically less than 5 mg of material, contained in a 100 μl platinum pan, was heated over the temperature range 25° C. to 325° C. at a constant heating rate of 10° C. per minute. A nitrogen purge gas was used with flow rate 100 ml per minute. The material exhibited a loss of 4.4% up to 50° C. followed by an additional loss of 1.7% between 70 and 140° C. suggesting that the material is solvated.

Figure 3:
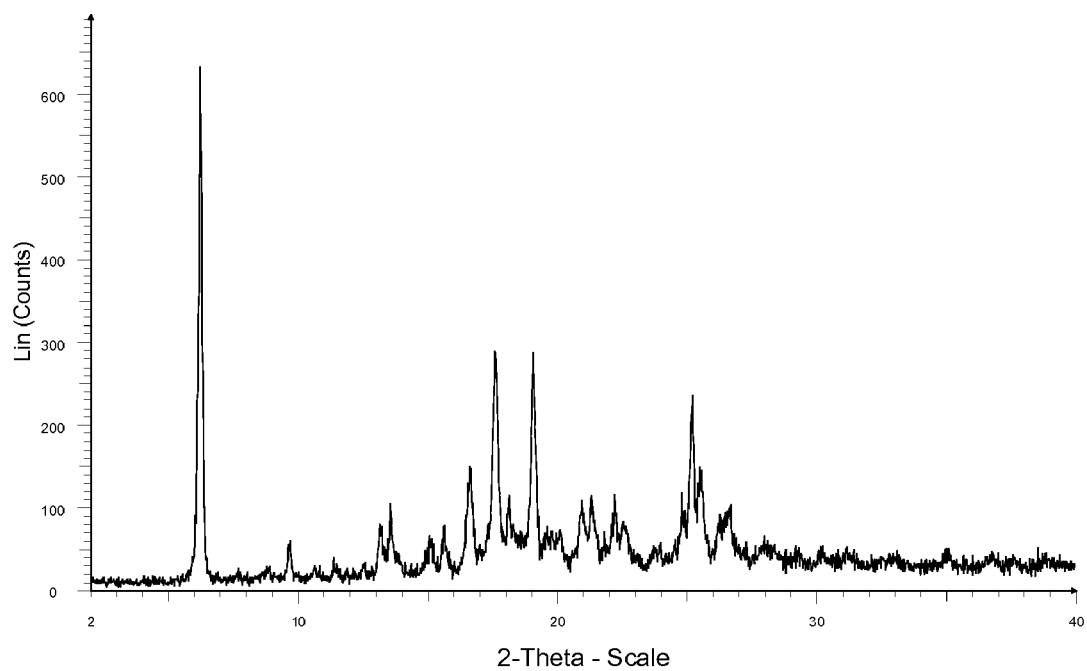
FIG. 3 demonstrates a powder X-ray diffraction pattern of (5-{2,4-bis[(3S)-3-methylmorpholin-4-yl]pyrido[2,3-d]pyrimidin-7-yl}-2-methoxyphenyl)methanol D-tartrate after being dried in a vacuum oven at 50° C. overnight. Some loss of crystallinity is indicated.

The product was further dried in a vacuum oven at 50° C. overnight. Powder X-ray diffraction indicated some loss of crystallinity. (see FIG. 3)

EXAMPLE 3b(i)

(5-{2,4-Bis[(3S)-3-methylmorpholin-4-yl]pyrido[2,3-d]pyrimidin-7-yl}-2-methoxyphenyl)methanol D-Tartrate 50 mg samples of the (5-{2,4-Bis[(3S)-3-methylmorpholin-4-yl]pyrido[2,3-d]pyrimidin-7-yl}-2-methoxyphenyl)methanol D-Tartrate were slurried for five days in (i) EtOAc at room temperature, (ii) MeCN at room temperature, and (iii) MeCN at 60° C. in MeCN. Powder X-ray diffraction patterns were recorded using a Bruker D5000 diffractometer (wavelength of X-rays 1.5418 Å Cu source, Voltage 40 kV, filament emission 40 mA). Samples were scanned from 2-40° 2θ using a 0.02° step and a 1 second per step time count.

The powder X-ray diffraction patterns indicated that for each of the slurry conditions above, the isolated materials had substantially similar crystal forms. The material isolated from the slurry in ethyl acetate was appeared to be the most crystalline.

Peaks were observed at:

| Angle/ °2θ (λ = 1.5418 Å) | d-spacing/Å | Relative Intensity/% |
|---|---|---|
| 6.18 | 14.28 | 100.0 |
| 9.62 | 9.18 | 8.5 |
| 13.16 | 6.72 | 12.0 |
| 13.55 | 6.53 | 16.3 |
| 16.60 | 5.33 | 23.5 |
| 17.60 | 5.03 | 45.5 |
| 19.07 | 4.65 | 45.2 |
| 25.20 | 3.53 | 37.0 |

EXAMPLE 3c (5-{2,4-Bis[(3S)-3-methylmorpholin-4-yl]pyrido[2,3-d]pyrimidin-7-yl}-2-methoxyphenyl)methanol Fumarate salt

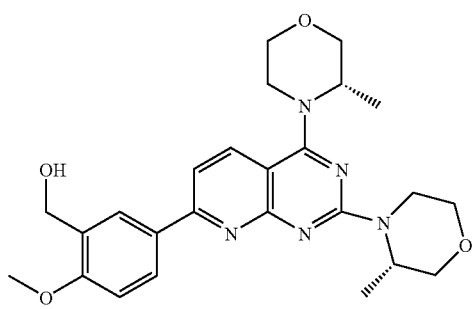

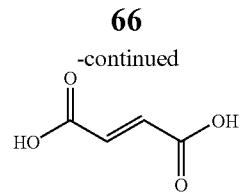

(5-{2,4-Bis[(3S)-3-methylmorpholin-4-yl]pyrido[2,3-d]pyrimidin-7-yl}-2-methoxyphenyl)methanol (10.00 g (96% w/w, 20.6 moles), fumaric Acid (2.63 g, 22.7 mmoles), water (84 ml) and methylated spirit industrial 74 O.P. (16.0 ml) were charged to a 250 ml reactor and heated to reflux (92° C.). The hot solution was filtered to remove extraneous matter. The filter was washed with a mixture of water (17 ml and methylated spirit industrial 74 O.P. (3 ml). On cooling the combined filtrates product precipitated. Product was isolated, washed with methylated spirit industrial 74 O.P. and dried to yield 10.12 g of (5-{2,4-Bis[(3S)-3-methylmorpholin-4-yl]pyrido[2,3-d]pyrimidin-7-yl}-2-methoxyphenyl)methanol Fumarate as a yellow solid.

NMR Spectrum: $^1$H NMR (400.132 MHz, DMSO-$d_6$) δ 1.28-1.36 (3H, d), 1.44-1.52 (3H, d), 3.31-4.00 (14H, m), 4.19 (1H, d), 4.38 (1H, d), 4.59 (2H, s) 4.72-4.80 (2H, broad m), 6.63 (2H, s) 7.15 (1H, d), 7.82 (1H, d), 8.12 (1H, dd), 8.35 (2H, s and d overlapped).

M.pt 175-178° C.

Figure 4:
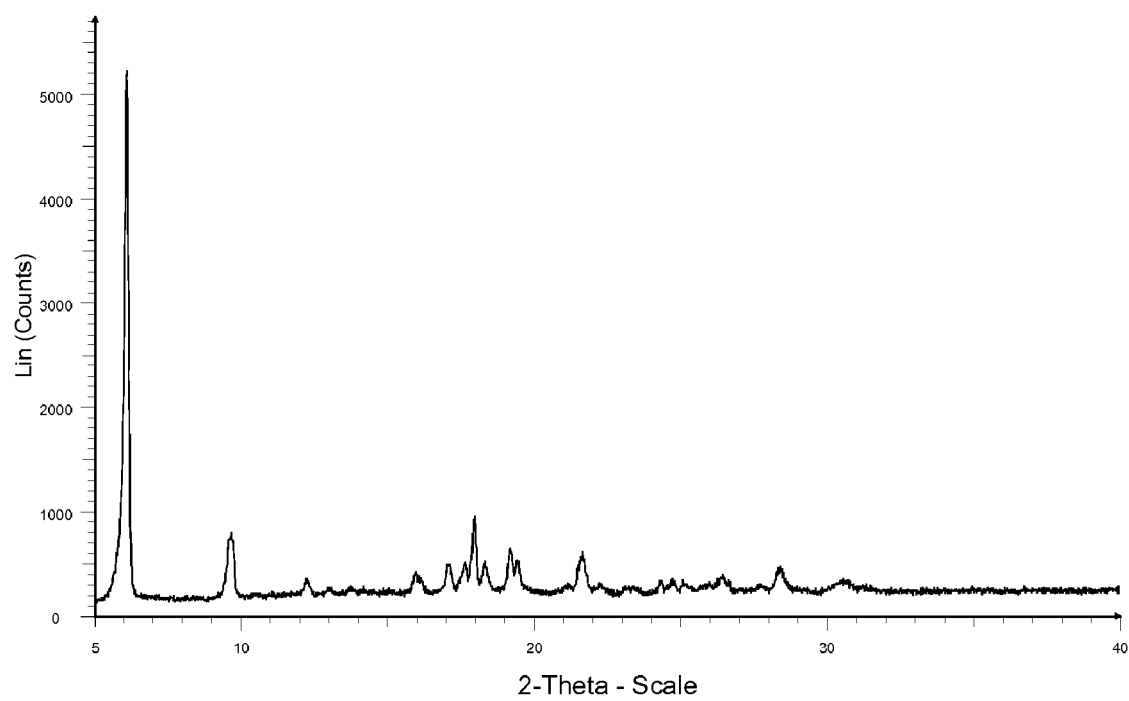
FIG. 4 demonstrates a powder X-ray diffraction pattern of (5-{2,4-bis[(3S)-3-methylmorpholin-4-yl]pyrido[2,3-d]pyrimidin-7-yl}-2-methoxyphenyl)methanol fumarate salt, Form A, recorded by a Bruker D8 diffractometer (wavelength of X-rays 1.5418 Å Cu source, Voltage 40 kV, filament emission 40 mA). The material was scanned from 5-40° 2θ using a step size of 0.014° and a 0.2 seconds per step time count.

Powder X-ray diffraction pattern was recorded on a Bruker D8 diffractometer (wavelength of X-rays 1.5418 Å Cu source, Voltage 40 kV, filament emission 40 mA) with the humidity stage attached. XRD patterns were recorded under varying humidity conditions; the material was scanned from 5-40° 2θ using a step size of 0.014° and a 0.2 seconds per step time count. (see FIG. 4—Form A)

Peaks were observed at:

| Angle/ °2θ (λ = 1.5418 Å) | d-spacing/Å | Relative Intensity/% |
|---|---|---|
| 6.03 (6.0) | 14.64 (14.6) | 100.0 (100) |
| 9.602 (9.6) | 9.20 (9.2) | 14.4 (14) |
| 12.20 (12.2) | 7.25 (7.2) | 6.5 (6) |
| 12.98 (13.0) | 6.81 (6.8) | 5.0 (5) |
| 17.06 (17.1) | 5.19 (5.2) | 9.2 (9) |
| 17.60 (17.6) | 5.03 (5.0) | 9.6 (10) |
| 17.93 (17.9) | 4.94 | 18.2 (18) |
| 18.30 (18.3) | 4.84 | 9.9 (10) |
| 19.16 (19.2) | 4.63 | 12.1 (12) |
| 19.41 (19.4) | 4.57 | 10.0 (10) |
| 21.63 (21.6) | 4.10 | 11.5 (11) |

In situ in the X-Ray Diffractometer, when the humidity levels were reduced to 20% humidity or less, the powder X-ray diffraction pattern obtained indicated a change in crystal form. This change was reversible, as the sample returned to the original form as the humidity was raised again. This was confirmed by the powder X-ray diffraction.

Under low humidity (5%), peaks were observed at:

| Angle/ °2θ (λ = 1.5418 Å) | d-spacing/Å | Relative Intensity/% |
|---|---|---|
| 6.04 (6.0) | 14.62 (14.6) | 100.0 (100) |
| 8.55 (8.5) | 10.34 (10.3) | 5.0 (5) |
| 9.60 (9.6) | 9.20 (9.2) | 9.3 (9) |
| 12.20 (12.2) | 7.25 (7.2) | 5.3 (5) |
| 13.00 (13.0) | 6.80 (6.8) | 3.1 (3) |

| Angle/ °2θ (λ = 1.5418 Å) | d-spacing/Å | Relative Intensity/% |
|---|---|---|
| 17.13 (17.1) | 5.17 (5.2) | 7.2 (7) |
| 17.72 (17.7) | 5.00 | 5.8 (6) |
| 17.91 (17.9) | 4.95 | 9.7 (10) |
| 18.33 (18.3) | 4.83 | 5.6 (6) |
| 19.28 (19.3) | 4.60 | 6.0 (6) |

Figure 5:
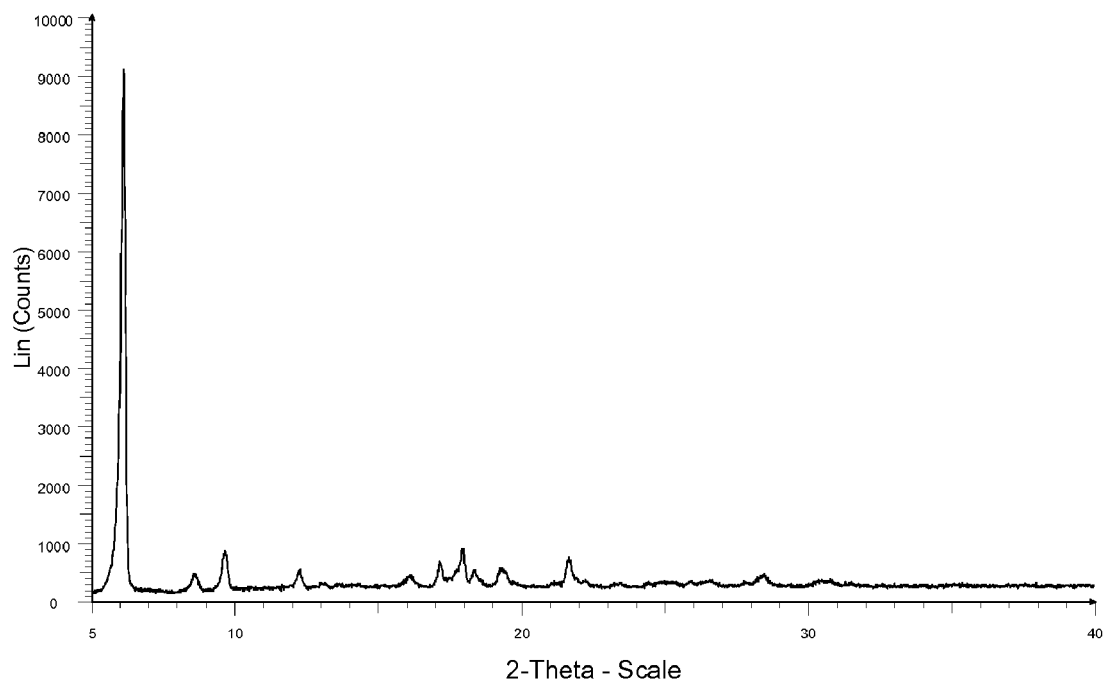
FIG. 5 demonstrates a powder X-ray diffraction pattern of (5-{2,4-bis[(3S)-3-methylmorpholin-4-yl]pyrido[2,3-d]pyrimidin-7-yl}-2-methoxyphenyl)methanol fumarate salt, Form B, obtained from the Form A of the fumarate salt when the humidity levels were reduced to 5% humidity.

(See FIG. 5 - Form B)

A variable temperature XRPD experiment was performed on Form A, which showed that on heating Form A converts to Form B. In light of this observation, melting points for Form A may reflect the melting point of Form B. Melting point: 180° C. (onset 174° C.)

A 10-30 mg of Form A material was added to a sample vial, along with a sufficient volume of water to achieve mobility without completely dissolving the sample. A magnetic flea was then added and the vial was placed on a stirrer plate at room temperature to stir at approximately 200-300 rpm for 5 weeks. The slurry was then isolated and analysed by XRPD. Measurements were made using a Bruker D4 diffractometer (wavelength of X-rays 1.5418 Å Cu source, Voltage 40 kV, filament emission 40 mA), samples are spun at 30 rpm to improve counting statistics. XRPD patterns were collected over the range 2° to 40°θ using a step size of 0.00570° and a 0.03 second per step count time.

| Angle/ °2θ (λ = 1.5418 Å) | d-spacing/Å | Relative Intensity/% |
|---|---|---|
| 6.29 (6.3) | 14.03 (14.0) | 100.0 (100) |
| 9.19 (9.2) | 9.61 (9.6) | 4.2 (4) |
| 10.14 (10.1) | 8.72 (8.7) | 6.2 (6) |
| 13.26 (13.3) | 6.67 (6.7) | 4.2 (4) |
| 14.42 (14.4) | 6.14 (6.1) | 4.8 (5) |
| 18.86 (18.9) | 4.70 (4.7) | 17.8 (18) |
| 20.30 (20.3) | 4.37 (4.4) | 5.6 (6) |
| 21.99 (22.0) | 4.04 (4.0) | 10.1 (10) |

Figure 6:
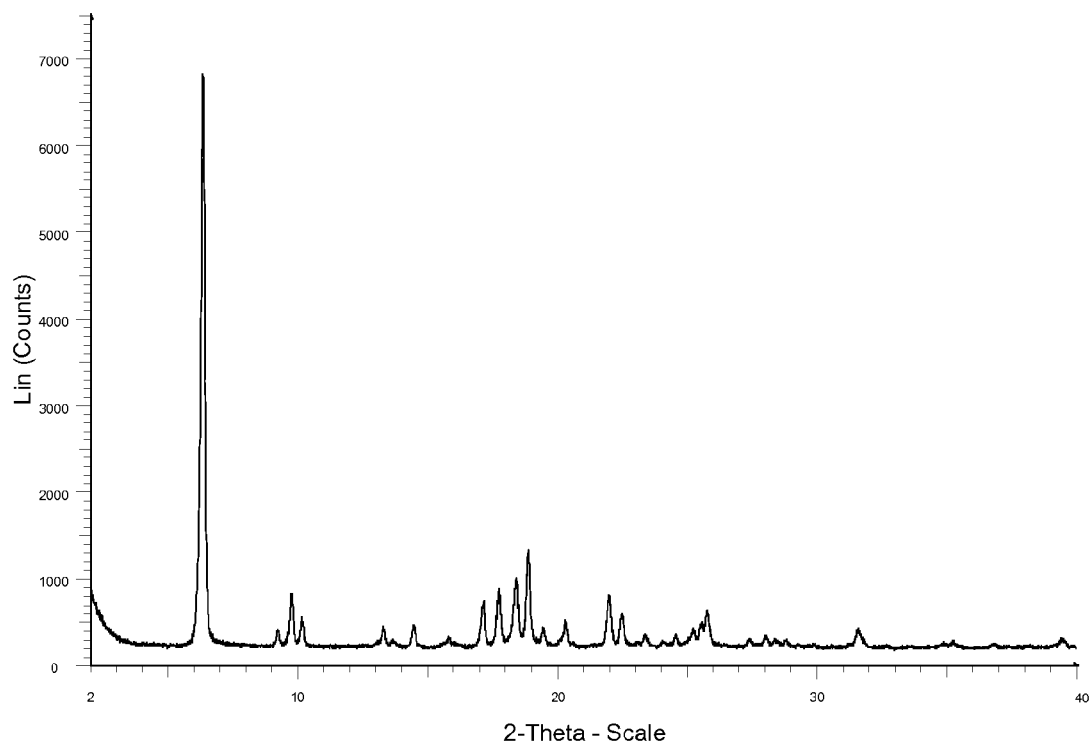
FIG. 6 demonstrates a powder X-ray diffraction pattern of (5-{2,4-bis[(3S)-3-methylmorpholin-4-yl]pyrido[2,3-d]pyrimidin-7-yl}-2-methoxyphenyl)methanol fumarate salt, Form C, obtained by stirring the Form A of the fumarate salt in water for five weeks. XRPD patterns were collected over the range of 2° to 40° 2θ using a step size of 0.00570° and a 0.03 second per step time count.

(See FIG. 6 - Form C)

Melting point of Form C measured by DSC 159° C. (onset 148° C.).

DSC: Typically less than 5 mg of material contained in a sample pan was heated over the temperature range 25° C. to 300° C. at a constant heating rate of 10° C. per minute. A purge gas using nitrogen was used—flow rate 100 ml per minute.

EXAMPLE 3c (5-{2,4-Bis[(3S)-3-methylmorpholin-4-yl]pyrido[2,3-d]pyrimidin-7-yl}-2-methoxyphenyl)methanol Fumarate salt. (Alternate Method)

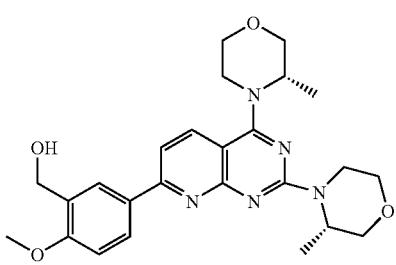

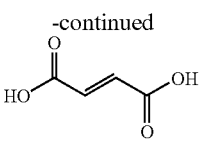

(5-{2,4-Bis[(3S)-3-methylmorpholin-4-yl]pyrido[2,3-d]pyrimidin-7-yl}-2-methoxyphenyl)methanol prepared by the alternate method (10.00 g, 20.6 mmoles), fumaric Acid (2.63 g, 22.7 mmoles), water (84 ml) and methylated spirit industrial 74 O.P. (16.0 ml) were charged to a 250 ml reactor and heated to reflux (92° C.). The hot solution was filtered to remove extraneous matter. The filter was washed with a mixture of water (17 ml) and methylated spirit industrial 74 O.P. (3 ml) and heated to 60° C. Seed crystals of Formula 5a Fumarate are added to the filtrates to initiate crystallisation. The resulting suspension is held at 60° C. for 2 hours to establish crystallisation and the growth of suitably sized crystals. The desired product precipitated out on further cooling of the suspension. The product was isolated, washed with methylated spirit industrial 74 O.P. and dried to yield 10.12 g of (5-{2,4-Bis[(3S)-3-methylmorpholin-4-yl]pyrido[2,3-d]pyrimidin-7-yl}-2-methoxyphenyl)methanol Fumarate as a yellow solid.

NMR Spectrum: $^1$H NMR (400.132 MHz, DMSO-$d_6$) δ 1.28-1.36 (3H, d), 1.44-1.52 (3H, d), 3.31-4.00 (14H, m), 4.19 (1H, d), 4.38 (1H, d), 4.59 (2H, s) 4.72-4.80 (2H, broad m), 6.63 (2H, s) 7.15 (1H, d), 7.82 (1H, d), 8.12 (1H, dd), 8.35 (2H, s and d overlapped).

M.pt 175-178° C.

EXAMPLE 4

Comparison of Bioaccessibility of a Compound of Formula 5a Free Base and Fumarate Salt Bioaccessibility of a compound of Formula 5a in the form of a free base and a fumarate salt was assessed using a TIM-1 multi-compartmental in vitro model (TNO Quality of Life, The Netherlands).

Initial assessment of solutions and suspensions of the free base form at concentrations of 10 mg/mL and doses of 200 mg and 500 mg were performed using a standard protocol (lipid-fasted with starting gastric pH of 2 and a gastric half-time of 30 minutes). The results showed little or no difference in the amount of drug available for absorption. (see Table 3).

TABLE 3

Bioaccessibility of the free base of the compound of Formula 5a using TIM-1 in vitro model

| | % of dose | |
|---|---|---|
| | 200 mg solution | 200 mg suspension |
| Total jejunum Absorption | 57.90 | 54.90 |
| Total ileum Absorption | 22.10 | 23.50 |
| Total jej + il Absorption | 80.00 | 78.40 |
| Total ileum effluent | 10.50 | 13.50 |
| Total residues and rinses | 6.30 | 5.80 |
| Total recovery | 96.80 | 97.60 |
| | 500 mg solution | 500 mg suspension |
| Total jejunum Absorption | 52.10 | 51.90 |
| Total ileum Absorption | 23.80 | 23.40 |
| Total jej + il Absorption | 75.90 | 75.40 |
| Total ileum effluent | 12.60 | 11.20 |

TABLE 3-continued

Bioaccessibility of the free base of the compound of Formula 5a using TIM-1 in vitro model

| | % of dose | |
| --- | --- | --- |
| Total residues and rinses | 5.00 | 5.20 |
| Total recovery | 93.60 | 91.70 |

Figure 7:
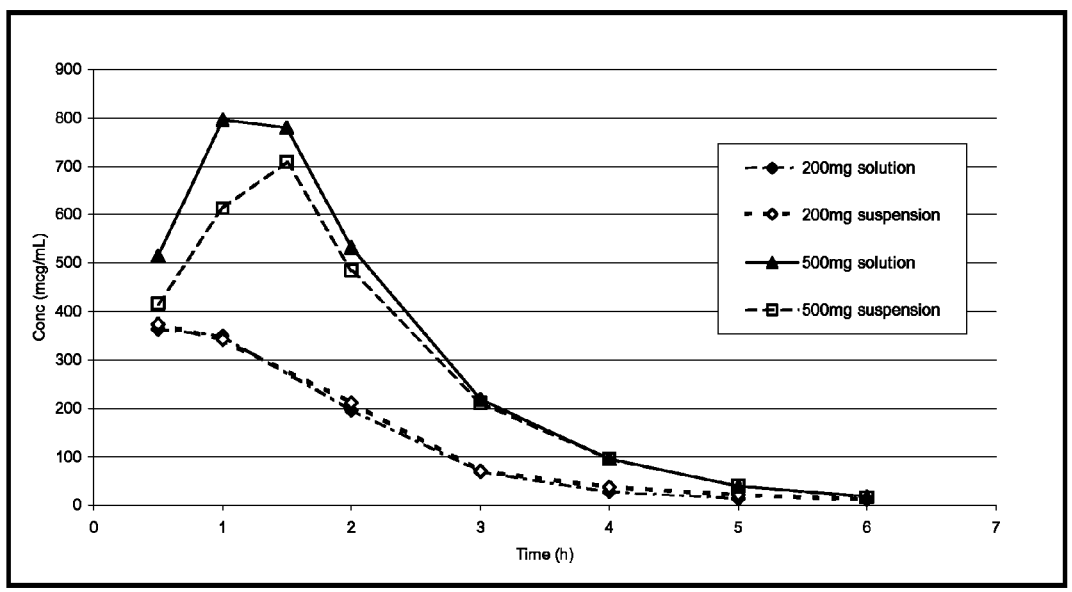
FIG. 7 demonstrates the comparison of bioaccessibility of a compound of Formula 5a in the form of a free base and a fumarate salt under a TIM-1 multi-compartmental in vitro model where the starting gastric pH is 2 with a gastric half-time of 30 minutes.

However, at the 500 mg dose, in situ samples from the duodenum compartment showed higher concentrations at early time-points for the solution in comparison to the suspension presentation (See FIG. 7).

Figure 8:
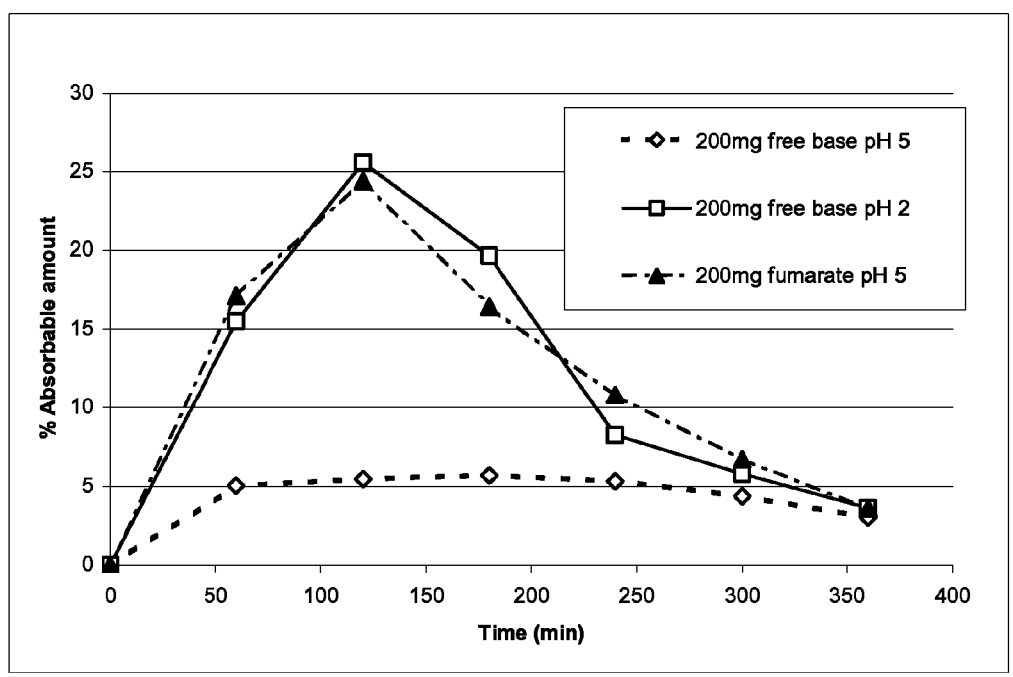
FIG. 8 demonstrates the comparison of bioaccessibility of a compound of Formula 5a in the form of a free base and a fumarate salt under a TIM-1 multi-compartmental in vitro model where the initial gastric pH is 5 with a gastric half-time of 20 minutes.

This led to a concern that a higher gastric pH and/or reduced gastric emptying time could lead to reduced bioavailability. A further study was performed with an increased initial gastric pH of 5 and a reduced gastric half-time of 20 min. In this study, 200 mg (free base equivalent) doses of 10 mg/mL suspensions of the free base and fumarate salt of the compound of Formula 5a were compared (see Table 4, FIG. 8).

TABLE 4

Bioaccessibility of a compound of Formula 5a (free base and fumarate salt) using TIM-1 in vitro model

| Dosage Form | 200 mg free base suspension gastric pH 2 | 200 mg free base suspension gastric pH 5 | 200 mg fumarate salt suspension gastric pH 5 |
| --- | --- | --- | --- |
| Total jejunum Absorption | 54.90 | 17.91 | 58.57 |
| Total ileum Absorption | 23.50 | 10.83 | 20.47 |

TABLE 4-continued

Bioaccessibility of a compound of Formula 5a (free base and fumarate salt) using TIM-1 in vitro model

| Dosage Form | 200 mg free base suspension gastric pH 2 | 200 mg free base suspension gastric pH 5 | 200 mg fumarate salt suspension gastric pH 5 |
| --- | --- | --- | --- |
| Total jej + il Absorption | 78.40 | 28.74 | 79.04 |
| Total ileum effluent | 13.50 | 47.46 | 9.16 |
| Total residues and rinses | 5.80 | 16.77 | 6.91 |
| Total recovery | 97.60 | 92.96 | 95.12 |

It was concluded that the fumarate salt of the compound of Formula 5a dosed as 200 mg (free base equivalent) of a 10 mg/mL suspension at high gastric pH gave the same bioaccessible fraction as the free base dosed under standard conditions, thus reducing the risk of in vivo variability. Thus, the fumarate salt was selected for further work.

Example 5

Stability Study

The stability of the fumarate salt of the compound of Formula 5a in the solid state was investigated for samples stored at 25° C./60% relative humidity (RH) in double lined polyethylene bags inside a fibreboard outer for long term stability testing. In addition, accelerated and stressed stability testing was performed at 40° C./75% RH and 50° C. AH (ambient humidity) in double lined polyethylene bags inside fibreboard outers. Further stress testing was performed on exposed samples at 40° C./75% RH and at ambient temperature in a light chamber (exposed to a minimum of 1.2 million lux hours visible light and 200 watt-hours/m² UV light), as shown in Table 5.

TABLE 5

| | Stability study | | | | | |
| --- | --- | --- | --- | --- | --- | --- |
| Test | Initial | 1 month, 40° C./ 75% RH exposed | 3 months, 25° C./ 60% RH | 3 months, 40° C./ 75% RH | 3 months, 50° C. | 10 days, light-exposed |
| Assay (water and solvent-free, % w/w) | 99.4 | 100.3 | 99.7 | 99.3 | 96.8 | 95.5 |
| Organic impurities | | | | | | |
| Largest single impurity (% w/w) | 0.16 | 0.16 | 0.16 | 0.16 | 0.16 | 0.97 |
| Total organic impurities$^a$ (% w/w) | 0.31 | 0.36 | 0.31 | 0.26 | 0.44 | 2.28 |
| Water content (% w/w) | 3.4 | 5.0 | 4.5 | 5.6 | 0.6 | 5.0 |

The results show that samples stored at 25° C./60% RH, 40° C./75% RH and 50° C. AH exhibit no significant degradation over a period of 3 months. There is some evidence of thermal degradation for the sample stored at 50° C. Following exposure to light under stress conditions, the sample had darkened on exposed surfaces and a loss of assay and corresponding increase in organic impurities was seen. An aldehyde was the largest observed impurity in this sample. These data indicate that that fumarate salt of the compound of Formula 5a may be stored at room temperature, however protection against exposure to light may ameliorate degradation effects.

Aldehyde Impurity (Relative Molecular Mass 463.52)

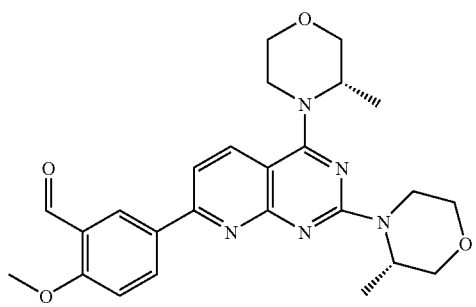

Example 6

Composition and Process Selection Study

Tablets were manufactured using wet granulation and direct compression processes, using the fumarate salt of a compound of Formula 5a and the compositions shown in Table 6.

TABLE 6

Conditions for composition and process selection study

| Run | Process | Drug Level | Primary Filler | Secondary Filler | Disintegrant | Lubricant | Binder |
|---|---|---|---|---|---|---|---|
| 1 | Dry | 10 | Mannitol | DCPA | L-HPC | SSF | PVP |
| 2 | Wet | 10 | MCC | DCPD | L-HPC | SSF | HPC |
| 3 | Dry | 10 | Mannitol | DCPD | L-HPC | MgSt | HPC |
| 4 | Dry | 40 | MCC | DCPA | L-HPC | SSF | HPC |
| 5 | Wet | 40 | Mannitol | DCPD | L-HPC | SSF | PVP |
| 6 | Wet | 40 | MCC | DCPD | SSG | MgSt | HPC |
| 7 | Wet | 10 | MCC | DCPA | L-HPC | MgSt | PVP |
| 8 | Wet | 10 | Mannitol | DCPD | SSG | MgSt | PVP |
| 9 | Wet | 40 | Mannitol | DCPA | L-HPC | MgSt | HPC |
| 10 | Wet | 10 | Mannitol | DCPA | SSG | SSF | HPC |
| 11 | Dry | 40 | Mannitol | DCPD | SSG | SSF | HPC |
| 12 | Dry | 40 | MCC | DCPD | L-HPC | MgSt | PVP |
| 13 | Wet | 40 | MCC | DCPA | SSG | SSF | PVP |
| 14 | Dry | 10 | MCC | DCPA | SSG | MgSt | HPC |
| 15 | Dry | 40 | Mannitol | DCPA | SSG | MgSt | PVP |
| 16 | Dry | 10 | MCC | DCPD | SSG | SSF | PVP |

In the dry process, the powdered ingredients (other than the lubricant) were charged to a suitable blender and mixed to produce a uniform distribution of drug substance (the fumarate salt of the compound of Formula 5a). The lubricant was added to the mixture prior to additional blending. The blend was compressed into tablet cores using a single station press to give tablets of the required hardness, disintegration and appearance.

In the wet process, the powdered ingredients (other than the lubricant) were charged to a suitable mixer and mixed to produce a uniform distribution of drug substance (Formula 5a fumarate salt). Water was added gradually to the powders with further mixing until a suitable wet mass was formed. The resultant granules were dried to an appropriate moisture content (less than 2% by weight). The dry granules were then passed through a suitable screen (mesh size 1.0 mm), before the lubricant was then added prior to blending. The blended granules were compressed into tablet cores using a single station press to give tablets of the required hardness, disintegration and appearance.

TABLE 7

Compositions for composition and process selection study

| | 10% free base (25 mg/tablet) | | 40% free base (100 mg/tablet) | |
|---|---|---|---|---|
| | mg/tab | % | mg/tab | % |
| Formula 5a fumarate | 31.25 | 12.5 | 125 | 500 |
| Mannitol or MCC[1] | 156.25 | 62.5 | 62.5 | 25 |
| DCPD or DCPA[1] | 37.5 | 15 | 37.5 | 15 |
| Disintegrant | 12.5 | 5 | 12.5 | 5 |
| Binder | 10 | 4 | 10 | 4 |
| Lubricant | 2.5 | 1 | 2.5 | 1 |

[1]Direct Compression grades were used in the dry process, and wet granulation grades were used in the wet process - see Table 1

These tablets were tested using the Compound Assay Test described above, and water content immediately after preparation and after periods of storage under various conditions of temperature and relative humidity (RH), as shown in Table 8.

TABLE 8

Stability data summary - composition and process selection tablets

| | | | 4 weeks storage | | | |
|---|---|---|---|---|---|---|
| | | Initial | 25° C./ 60% RH | 40° C. | 70° C. | 70° C./ 80% RH |
| Run 1 (25 mg, dry) | Formula 5a (mg/tablet) | 23.80 | 23.97 | 23.82 | 22.24 | 21.41 |
| | Aldehyde (%) | 0.34 | 0.38 | 0.42 | 2.10 | 2.81 |
| | Total impurities (%) | 1.25 | 1.30 | 1.34 | 4.36 | 6.13 |
| | Water content (% w/w) | 1.73 | | Not determined | | |
| Run 2 (25 mg, wet) | Formula 5a (mg/tablet) | 25.89 | 24.88 | 25.85 | 25.50 | 23.52 |
| | Aldehyde (%) | 0.46 | 0.41 | 0.52 | 2.03 | 0.86 |
| | Total impurities (%) | 1.53 | 1.38 | 1.53 | 3.93 | 3.00 |

TABLE 8-continued

Stability data summary - composition and process selection tablets

|  |  |  | \multicolumn{4}{c}{4 weeks storage} |  |
|---|---|---|---|---|---|---|
|  |  | Initial | 25° C./ 60% RH | 40° C. | 70° C. | 70° C./ 80% RH |
|  | Water content (% w/w) | 3.91 | \multicolumn{4}{c}{Not determined} | | | |
| Run 3 (25 mg, dry) | Formula 5a (mg/tablet) | 22.97 | 22.72 | 23.05 | 23.23 | 22.70 |
|  | Aldehyde (%) | 0.32 | 0.30 | 0.44 | 1.07 | 0.45 |
|  | Total impurities (%) | 1.21 | 1.18 | 1.33 | 2.46 | 1.56 |
|  | Water content (% w/w) | 2.74 | \multicolumn{4}{c}{Not determined} | | | |
| Run 4 (100 mg, dry) | Formula 5a (mg/tablet) | 90.61 | 91.76 | 95.15 | 96.47 | 91.37 |
|  | Aldehyde (%) | 0.29 | 0.27 | 0.29 | 0.59 | 0.37 |
|  | Total impurities (%) | 1.16 | 1.15 | 1.22 | 1.63 | 1.41 |
|  | Water content (% w/w) | 4.36 | \multicolumn{4}{c}{Not determined} | | | |
| Run 5 (100 mg, wet) | Formula 5a (mg/tablet) | 101.27 | 94.57 | 98.29 | 97.06 | 94.83 |
|  | Aldehyde (%) | 0.29 | 0.25 | 0.28 | 0.89 | 0.39 |
|  | Total impurities (%) | 1.33 | 1.17 | 1.23 | 2.05 | 1.54 |
|  | Water content (% w/w) | 4.35 | \multicolumn{4}{c}{Not determined} | | | |
| Run 6 (100 mg, wet) | Formula 5a (mg/tablet) | 96.74 | 96.11 | 97.81 | 99.51 | 95.14 |
|  | Aldehyde (%) | 0.26 | 0.27 | 0.29 | 0.89 | 0.33 |
|  | Total impurities (%) | 1.20 | 1.21 | 1.24 | 2.10 | 1.35 |
|  | Water content (% w/w) | 4.47 | \multicolumn{4}{c}{Not determined} | | | |
| Run 7 (25 mg, wet) | Formula 5a (mg/tablet) | 24.48 | 23.78 | 24.29 | 23.68 | 22.20 |
|  | Aldehyde (%) | 0.38 | 0.36 | 0.44 | 1.78 | 1.80 |
|  | Total impurities (%) | 1.32 | 1.31 | 1.38 | 3.50 | 3.78 |
|  | Water content (% w/w) | 3.55 | \multicolumn{4}{c}{Not determined} | | | |
| Run 8 (25 mg, wet) | Formula 5a (mg/tablet) | 23.96 | 24.19 | 24.86 | 22.82 | 22.87 |
|  | Aldehyde (%) | 0.50 | 0.41 | 0.45 | 2.76 | 0.80 |
|  | Total impurities (%) | 1.43 | 1.35 | 1.44 | 5.13 | 1.92 |
|  | Water content (% w/w) | 4.10 | \multicolumn{4}{c}{Not determined} | | | |
| Run 9 (100 mg, wet) | Formula 5a (mg/tablet) | 93.96 | 92.65 | 94.21 | 93.31 | 91.41 |
|  | Aldehyde (%) | 0.24 | 0.23 | 0.28 | 0.56 | 0.39 |
|  | Total impurities (%) | 1.15 | 1.14 | 1.19 | 1.58 | 1.27 |
|  | Water content (% w/w) | 2.35 | \multicolumn{4}{c}{Not determined} | | | |
| Run 10 (25 mg, wet) | Formula 5a (mg/tablet) | 23.89 | 24.26 | 24.17 | 22.72 | 23.27 |
|  | Aldehyde (%) | 0.45 | 0.39 | 0.50 | 3.35 | 0.67 |
|  | Total impurities (%) | 1.39 | 1.32 | 1.44 | 6.30 | 1.78 |
|  | Water content (% w/w) | 1.45 | \multicolumn{4}{c}{Not determined} | | | |
| Run 11 (100 mg, dry) | Formula 5a (mg/tablet) | 95.26 | 92.43 | 92.34 | 98.03 | 94.92 |
|  | Aldehyde (%) | 0.26 | 0.26 | 0.29 | 0.67 | 0.29 |
|  | Total impurities (%) | 1.17 | 1.17 | 1.19 | 1.74 | 1.32 |
|  | Water content (% w/w) | 5.27 | \multicolumn{4}{c}{Not determined} | | | |
| Run 12 (100 mg, dry) | Formula 5a (mg/tablet) | 95.10 | 93.58 | 94.41 | 101.82 | 95.54 |
|  | Aldehyde (%) | 0.29 | 0.26 | 0.28 | 0.77 | 1.02 |
|  | Total impurities (%) | 1.21 | 1.16 | 1.19 | 1.95 | 2.29 |
|  | Water content (% w/w) | 7.17 | \multicolumn{4}{c}{Not determined} | | | |
| Run 13 (100 mg, wet) | Formula 5a (mg/tablet) | 96.98 | 92.54 | 94.81 | 94.56 | 91.97 |
|  | Aldehyde (%) | 0.27 | 0.26 | 0.31 | 0.97 | 0.76 |
|  | Total impurities (%) | 1.20 | 1.19 | 1.28 | 2.24 | 1.73 |
|  | Water content (% w/w) | 2.87 | \multicolumn{4}{c}{Not determined} | | | |

TABLE 8-continued

Stability data summary - composition and process selection tablets

|  |  |  | 25° C./ |  |  | 70° C./ |
|---|---|---|---|---|---|---|
|  |  | Initial | 60% RH | 40° C. | 70° C. | 80% RH |
|  |  |  | 4 weeks storage | | | |

| | | Initial | 25° C./ 60% RH | 40° C. | 70° C. | 70° C./ 80% RH |
|---|---|---|---|---|---|---|
| Run 14 (25 mg, dry) | Formula 5a (mg/tablet) | 23.48 | 23.24 | 25.17 | 23.10 | 22.70 |
| | Aldehyde(%) | 0.33 | 0.30 | 0.38 | 1.40 | 0.85 |
| | Total impurities (%) | 1.24 | 1.20 | 1.40 | 2.84 | 2.42 |
| | Water content (% w/w) | 4.69 | | Not determined | | |
| Run 15 (100 mg, dry) | Formula 5a (mg/tablet) | 93.48 | 95.40 | 95.79 | 92.37 | 92.65 |
| | Aldehyde (%) | 0.28 | 0.26 | 0.30 | 1.35 | 0.42 |
| | Total impurities (%) | 1.19 | 1.19 | 1.22 | 2.78 | 1.43 |
| | Water content (% w/w) | 3.98 | | Not determined | | |
| Run 16 (25 mg, dry) | Formula 5a (mg/tablet) | 24.21 | 21.84 | 24.69 | 27.10 | 23.79 |
| | Aldehyde (%) | 0.39 | 0.33 | 0.39 | 1.95 | 1.34 |
| | Total impurities (%) | 1.32 | 1.17 | 1.35 | 3.99 | 3.49 |
| | Water content (% w/w) | 6.57 | | Not determined | | |

Example 7

Stability Study (10 and 100 mg Tablets with Coating A)

A composition comprising 25% Formula 5a fumarate salt, without a binder, was selected for further study. Tablet cores of 10 and 100 mg strength active agent were prepared and coated with a yellow film coating having a high content of iron oxide pigment and were investigated in a stability study varying temperature and humidity.

A 10 mg tablet composition is shown in Table 9.

TABLE 9

10 mg tablet (10 mg Formula 5a, mannitol/dibasic calcium phosphate anhydrous filler)

| Ingredient Tablet core | mg/ tablet | % of core weight | Function |
|---|---|---|---|
| Formula 5a fumarate salt | 12.5 | 25.0 | Drug substance |
| Mannitol | 23.5 | 47.0 | Filler |
| Dibasic calcium phosphate anhydrous | 10.0 | 20.0 | Filler |
| Low-substitution hydroxypropyl cellulose | 3.5 | 7.0 | Disintegrant |
| Magnesium stearate | 0.5 | 1.00 | Lubricant |
| Core tablet weight | 50.0 | | |

| Tablet coating (A) | mg/ tablet | % of coating weight | Function |
|---|---|---|---|
| Polyvinyl alcohol | 0.800 | 40.00 | Film former |
| Titanium dioxide | 0.200 | 10.00 | Opacifier |
| Polyethylene glycol 3350 | 0.404 | 20.20 | Plasticiser |
| Iron oxide yellow | 0.300 | 15.00 | Colouring agent |
| Talc | 0.296 | 14.80 | Anti-tack agent |

| | | % of core weight | |
|---|---|---|---|
| Nominal coating weight | 2.000 | 4.00 | |

The tablets may be prepared using the following wet granulation process:

Formula 5a fumarate salt (0.250 kg), mannitol (Pearlitol™ 160 C, Roquette Freres S.A., 0.470 kg); Dibasic calcium phosphate anhydrous (Calipharm A, Innophos, 0.200 kg); and Low-substitution hydroxypropyl cellulose (L-HPC LH-21, Shin Etsu Chemical Co., 0.070 kg) were mixed together in a Collette Gral 10 high shear mixer. Water (0.150 kg, addition rate of 0.100 kg/minute) was sprayed into the mixture and the mixture granulated for about 6.5 minutes. The wet mass was passed through a screen (mesh size 9.5 mm). The granules were dried in a Vector FLM-3 fluid bed dryer (inlet air temperature 60° C., air flow rate sufficient to fluidise the granule bed) to a moisture content of <2% w/w and the dried granules milled using a Quadro Comil 194 (screen mesh 0.062 inches (1.6 mm), 400 rpm).

Two of the above portions are combined and 0.020 g magnesium stearate added. The 2 kg batch is transferred to a Pharmatech MB 100 blender (10 liter drum) and the mixture blended. The mixture is then compressed into tablets (50 mg compression weight, plain, round, bi-convex 4.5 mm diameter) using a Riva Piccola tablet press (30,000 tablets per hour, 3 kN compression force). The tablets are then coated using an O'Hara Labcoat II-X coater (15 inch drum) with Opadry™ II Yellow (Colorcon 85F38196, 200 g/kg aqueous solution). The total coating solution applied is equivalent to 40 g/kg of Opadry per mass of tablet cores.

A 100 mg tablet composition is shown in Table 10.

TABLE 10

100 mg tablet (100 mg Formula 5a, mannitol/dibasic calcium phosphate anhydrous filler)

| Ingredient Tablet core | mg/ tablet | % of core weight | Function |
|---|---|---|---|
| Formula 5a fumarate salt | 125.0 | 25.0 | Drug substance |
| Mannitol | 235.0 | 47.0 | Filler |
| Dibasic calcium phosphate anhydrous | 100.0 | 20.0 | Filler |

TABLE 10-continued 100 mg tablet (100 mg Formula 5a, mannitol/dibasic calcium phosphate anhydrous filler)

| | | | |
|---|---|---|---|
| Low-substitution hydroxypropyl cellulose | 35.0 | 7.0 | Disintegrant |
| Magnesium stearate | 5.0 | 1.00 | Lubricant |
| Core tablet weight | 500.0 | | |

| Tablet coating (A) | mg/tablet | % of coating weight | Function |
|---|---|---|---|
| Polyvinyl alcohol | 8.00 | 40.00 | Film former |
| Titanium dioxide | 2.00 | 10.00 | Opacifier |
| Polyethylene glycol 3350 | 4.04 | 20.20 | Plasticiser |
| Iron oxide yellow | 3.00 | 15.00 | Colouring agent |
| Talc | 2.96 | 14.80 | Anti-tack agent |

| | | % of core weight |
|---|---|---|
| Nominal coating weight | 20.0 | 4.0 |

The 100 mg tablets may be prepared using an analogous method to that described for the preparation of the 10 mg tablets shown in Table 9.

A stability study covering long-term (25° C./60% RH), accelerated (40° C./75% RH) and stressed (50° C. ambient RH) conditions was performed on batches of yellow film-coated 10 and 100 mg tablets prepared as described in Tables 9 and 10 which were stored in US high-density polyethylene (HDPE) bottles with standard, lined, screw-neck closures; and the results are summarised in Table 11.

TABLE 11

Stability data summary for tablet compositions of formula 5a fumarate salt with coating A

| | | | 4 weeks storage | | | |
|---|---|---|---|---|---|---|
| | | Initial | 25° C./60% RH | 40° C./75% RH (closed) | 40° C./75% RH (open) | 50° C. |
| 10 mg tablets | Formula 5a (mg/tablet) | 9.6 | 9.5 | 9.5 | 9.5 | 9.7 |
| | Largest single impurity (%) | 0.16 | 0.16 | 0.16 | 0.16 | 0.16 |
| | Total impurities (%) | 0.36 | 0.38 | 0.41 | 0.37 | 0.46 |
| | Dissolution (% release after 45 minutes) | 98 | 98 | 99 | 97 | 99 |
| 100 mg tablets | Formula 5a (mg/tablet) | 98 | 99 | 99 | 98 | 99 |
| | Largest single impurity (%) | 0.16 | 0.17 | 0.17 | 0.16 | 0.17 |
| | Total impurities (%) | 0.31 | 0.32 | 0.39 | 0.36 | 0.47 |
| | Dissolution (% release after 45 minutes) | 99 | 100 | 99 | 99 | 100 |

No significant change in description, assay, degradation products or dissolution has been observed for tablet compositions of formula 5a fumarate salt with coating A after storage for up to 4 weeks under the conditions studied. The extent of the observed degradation at the 50° C. condition is considered acceptable for all tested strengths.

Example 8

Photostability Study (10 and 20 mg Tablets with Coating B)

The tablet core composition from Example 7 was selected for further study. Tablet cores of 10 and 20 mg strength active agent were prepared and coated with a yellow film coating having a low content of iron oxide pigment were investigated in a photostability study.

A 10 mg tablet composition is shown in Table 12.

TABLE 12

10 mg tablet (10 mg Formula 5a, mannitol/dibasic calcium phosphate anhydrous filler)

| Ingredient Tablet core | mg/tablet | % of core weight | Function |
|---|---|---|---|
| Formula 5a fumarate salt | 12.5 | 25.0 | Drug substance |
| Mannitol | 23.5 | 47.0 | Filler |
| Dibasic calcium phosphate anhydrous | 10.0 | 20.0 | Filler |
| Low-substitution hydroxypropyl cellulose | 3.5 | 7.0 | Disintegrant |
| Magnesium stearate | 0.5 | 1.00 | Lubricant |
| Core tablet weight | 50.0 | | |

| Tablet coating (B) | mg/tablet | % of coating weight | Function |
|---|---|---|---|
| Polyvinyl alcohol | 0.800 | 40.00 | Film former |
| Titanium dioxide | 0.470 | 23.50 | Opacifier |
| Polyethylene glycol 3350 | 0.404 | 20.20 | Plasticiser |
| Iron oxide yellow | 0.030 | 1.50 | Colouring agent |
| Talc | 0.296 | 14.80 | Anti-tack agent |

| | | % of core weight |
|---|---|---|
| Nominal coating weight | 2.000 | 4.00 |

The tablet cores may be prepared using, for example, the wet granulation process described previously (see Example 7). The tablet cores are then coated using an O'Hara Labcoat II-X coater with Opadry II Yellow (Colorcon 85F32410, 200 g/kg aqueous solution). The total coating solution applied is equivalent to 40 g/kg of Opadry per mass of tablet cores.

A 20 mg tablet composition is shown in Table 13.

TABLE 13

20 mg tablet (20 mg Formula 5a, mannitol/dibasic calcium phosphate anhydrous filler)

| Ingredient Tablet core | mg/tablet | % of core weight | Function |
|---|---|---|---|
| Formula 5a fumarate salt | 25.0 | 25.0 | Drug substance |
| Mannitol | 47.0 | 47.0 | Filler |
| Dibasic calcium phosphate anhydrous | 20.0 | 20.0 | Filler |
| Low-substitution hydroxypropyl cellulose | 7.0 | 7.0 | Disintegrant |
| Magnesium stearate | 1.0 | 1.0 | Lubricant |
| Core tablet weight | 100.0 | | |

| Tablet coating (B) | mg/tablet | % of coating weight | Function |
|---|---|---|---|
| Polyvinyl alcohol | 1.600 | 40.00 | Film former |
| Titanium dioxide | 0.940 | 23.50 | Opacifier |

TABLE 13-continued 20 mg tablet (20 mg Formula 5a, mannitol/dibasic calcium phosphate anhydrous filler)

| | | | |
|---|---|---|---|
| Polyethylene glycol 3350 | 0.808 | 20.20 | Plasticiser |
| Iron oxide yellow | 0.060 | 1.50 | Colouring agent |
| Talc | 0.592 | 14.80 | Anti-tack agent |

| | % of core weight | |
|---|---|---|
| Nominal coating weight | 4.00 | 4.0 |

The 20 mg tablets may be prepared using an analogous method to that described for the preparation of the 10 mg tablet compositions shown in Table 12.

Photostability was assessed for the 10 mg and 20 mg tablet compositions described in Tables 12 and 13 above. An illumination of not less than 1.2 million lux hours and an integrated near ultraviolet energy of not less than 200 watt hours per square metre (Wh/m2) was applied to the 10 mg and 20 mg yellow film coated tablets in an open petri dish, HDPE bottles only and HDPE bottles in secondary pack consisting of a cardboard carton with cardboard liner. The photostability data are presented in Tables 14 and 15.

TABLE 14

10 mg tablets

| Test | Initial | Open | HDPE bottle | HDPE bottle in secondary container |
|---|---|---|---|---|
| Description | Plain, round, biconvex, yellow film-coated tablets | NCH* | NCH* | NCH* |
| Dissolution (45 minutes) | 99 | 99 | 100 | 100 |
| Active agent (mg/tablet) | 9.8 | 9.3 | 9.7 | 9.8 |
| Largest single impurity (%) | 0.13 | 2.50 | 1.13 | 0.12 |
| Total impurities (%) | 0.25 | 3.80 | 1.58 | 0.23 |

*NCH = No change from initial time-point

TABLE 15

20 mg tablets

| Test | Initial | Open | HDPE bottle | HDPE bottle in secondary container |
|---|---|---|---|---|
| Description | Plain, round, biconvex, yellow film-coated tablets | NCH* | NCH* | NCH* |
| Dissolution (45 minutes) | 98 | 98 | 99 | 98 |
| Active agent (mg/tablet) | 19.5 | 18.9 | 19.4 | 19.5 |
| Single impurity (%) | 0.12% w/w | 1.75 | 0.49 | 0.13 |
| Total impurities (%) | 0.18 | 2.47 | 0.76 | 0.24 |

NCH = No change from initial time-point

For the tablets with coating B, degradation occurred in the unpacked tablets and in the tablet packed in the HDPE bottle only. No significant degradation, or changes were observed in tablets packed in HDPE bottles within a secondary cardboard carton. Packaging consisting of a HDPE bottle in a secondary cardboard carton with cardboard liner may therefore ameliorate light effects on tablets with coating B.

Example 9

Stability Study (10, 20 and 100 mg Tablets with Coating B)

Assessment of stability was performed for the 10 mg and 20 mg tablet compositions described in Tables 12 and 13 above, and in addition for a 100 mg tablet composition as shown in Table 16.

TABLE 16

100 mg tablet (100 mg Formula 5a, mannitol/dibasic calcium phosphate anhydrous filler)

| Ingredient Tablet core | mg/ tablet | % of core weight | Function |
|---|---|---|---|
| Formula 5a fumarate salt | 125.0 | 25.0 | Drug substance |
| Mannitol | 235.0 | 47.0 | Filler |
| Dibasic calcium phosphate anhydrous | 100.0 | 20.0 | Filler |
| Low-substitution hydroxypropyl cellulose | 35.0 | 7.0 | Disintegrant |
| Magnesium stearate | 5.0 | 1.00 | Lubricant |
| Core tablet weight | 500.0 | | |

| Tablet coating (B) | mg/ tablet | % of coating weight | Function |
|---|---|---|---|
| Polyvinyl alcohol | 8.000 | 40.00 | Film former |
| Titanium dioxide | 4.700 | 23.50 | Opacifier |
| Polyethylene glycol 3350 | 4.040 | 20.20 | Plasticiser |
| Iron oxide yellow | 0.300 | 1.50 | Colouring agent |
| Talc | 2.960 | 14.80 | Anti-tack agent |

| | % of core weight | |
|---|---|---|
| Nominal coating weight | 20.00 | 4.0 |

The 100 mg tablets may be prepared using an analogous method to that described for the preparation of the 10 mg tablet compositions shown in Table 12.

A stability study covering long-term (25° C./60% RH), accelerated (40° C./75% RH) and stressed (50° C. ambient RH) conditions was performed on batches of yellow film-coated 10, 20 mg and 100 mg tablets prepared as described in Tables 12, 13 and 16 which were stored in US high-density polyethylene (HDPE) bottles with standard, lined, screw-neck closures, and the results are summarised in Table 17.

TABLE 17

Stability data summary for tablet compositions of formula 5a fumarate salt with coating B

| | | | | 4 weeks storage | | |
|---|---|---|---|---|---|---|
| | | Initial | 25° C./ 60% RH | 40° C./ 75% RH (closed) | 40° C./ 75% RH (open) | 50° C. |
| 10 mg tablets | Formula 5a (mg/tablet) | 9.8 | 9.7 | 9.7 | 9.5 | 9.7 |
| | Largest single impurity (%) | 0.13 | 0.12 | 0.12 | 0.12 | 0.15 |
| | Total impurities (%) | 0.25 | 0.25 | 0.27 | 0.23 | 0.34 |

TABLE 17-continued

Stability data summary for tablet compositions of formula 5a fumarate salt with coating B

| | | | 4 weeks storage | | | |
|---|---|---|---|---|---|---|
| | | Initial | 25° C./ 60% RH | 40° C./ 75% RH (closed) | 40° C./ 75% RH (open) | 50° C. |
| | Dissolution (% release after 45 minutes) | 99 | 99 | 100 | 101 | 100 |
| 20 mg tablets | Formula 5a (mg/tablet) | 19.5 | 19.4 | 19.3 | 19.0 | 19.2 |
| | Largest single impurity (%) | 0.12 | 0.12 | 0.12 | 0.12 | 0.15 |
| | Total impurities (%) | 0.18 | 0.24 | 0.26 | 0.23 | 0.33 |
| | Dissolution (% release after 45 minutes) | 98 | 98 | 100 | 99 | 99 |
| 100 mg tablets | Formula 5a (mg/tablet) | 99 | 100 | 101 | 100 | 102 |
| | Largest single impurity (%) | 0.13 | 0.12 | 0.13 | 0.13 | 0.14 |
| | Total impurities (%) | 0.19 | 0.24 | 0.29 | 0.26 | 0.54 |
| | Dissolution (% release after 45 minutes) | 97 | 96 | 95 | 97 | 96 |

No significant change in description, assay, degradation products or dissolution has been observed for tablet compositions of formula 5a fumarate salt with coating B after storage for up to 4 weeks at under the conditions studied. The extent of the observed degradation at the 50° C. condition is considered acceptable for all tested strengths.

REFERENCE LIST

The following documents are all herein incorporated by reference.

1) Brown, et al., *Nature*, 369, 756-758 (1994)
2) Chiu, et al, *Proc Natl Acad Sci*, 91, 12574-12578 (1994)
3) Sabatini, et al., *Cell*, 78, 35-43, (1994)
4) Sabers, et al., *J Biol Chem*, 270, 825-822 (1995)
5) Abraham, *Curr Opin Immunol*, 8, 412-418 (1996)
6) Schmelze and Hall, *Cell*, 103, 253-262 (2000)
7) Burnett, et al., *Proc Natl Acad Sci*, 95, 1432-1437 (1998)
8) Terada, et al., *Proc Natl Acad Sci*, 91, 11477-11481 (1994)
9) Jeffries, et al., *EMBO J*. 16, 3693-3704 (1997)
10) Bjornsti and Houghton, *Nat Rev Cancer*, 4, 335-348 (2004)
11) Gingras, et al., *Genes Dev*, 13, 1422-1437 (1999)
12) Gingras, et al., *Genes Dev*, 15, 807-826 (2001)
13) Neuhaus, et al., *Liver Transplantation*, 7, 473-484 (2001)
14) Woods and Marks, *Ann Rev Med*, 55, 169-178 (2004)
15) Dahia, *Endocrine-Related Cancer*, 7, 115-129 (2000)
16) Cristofano and Pandolfi, *Cell*, 100, 387-390 (2000)
17) Samuels, et al., *Science*, 304, 554 (2004)
18) Huang and Houghton, *Curr Opin Pharmacol*, 3, 371-377 (2003)
19) Sawyers, *Cancer Cell*, 4, 343-348 (2003)
20) Huang and Houghton, *Curr Opin in Invest Drugs*, 3, 295-304 (2002)
21) Brunn, et al., *EMBO J*. 15, 5256-5267 (1996)
22) Edinger, et al., *Cancer Res*, 63, 8451-8460, (2003)
23) Lawrence, et al., *Curr Top Microbiol Immunol*, 279, 199-213 (2004)
24) Eshleman, et al., *Cancer Res*, 62, 7291-7297 (2002)
25) Berge, et al., *J. Pharm. Sci.*, 66, 1-19 (1977).
26) Green, T. and Wuts, P., "Protective Groups in Organic Synthesis", 3rd Edition, John Wiley and Sons (1999).
27) "Handbook of Pharmaceutical Additives", 2nd Edition (eds. M. Ash and I. Ash), 2001 (Synapse Information Resources, Inc., Endicott, N.Y., USA).
28) "Remington's Pharmaceutical Sciences", 20th edition, pub. Lippincott, Williams & Wilkins, 2000.
29) "Handbook of Pharmaceutical Excipients", 2nd edition, 1994.

The invention claimed is:

1. A process for preparing a mTOR kinase inhibitor of Formula 5:

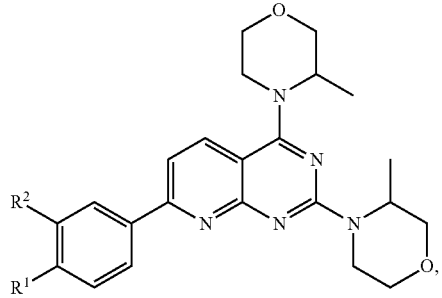

wherein:
$R^1$ is hydrogen or $OR^3$; and
$R^2$ is $CH_2OR^4$, CN, $CO_2R^5$ or $CONR^6R^7$; and wherein,
$R^3$ is a $C_{1-4}$ alkyl group;
$R^4$ is hydrogen or a —$COR^8$ group wherein $R^8$ is a secondary $C_{3-6}$alkyl or tertiary $C_{4-6}$alkyl group;
$R^5$ is a $C_{1-4}$alkyl group
$R^6$ is hydrogen or a $C_{1-4}$ alkyl group; and
$R^7$ is a $C_{1-4}$ alkyl group;
comprising:
(i) reacting a compound of Formula 2a:

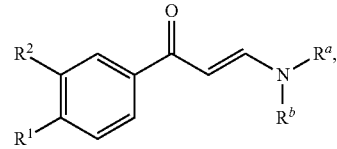

wherein:
$R^2$ is $CH_2OR^4$, CN, $CO_2R^5$ or $CONR^6R^7$; and wherein,
$R^4$ is a —$COR^8$ group wherein $R^8$ is a secondary $C_{3-6}$alkyl or tertiary $C_{4-6}$alkyl group; and
$R^a$ and $R^b$ are each independently hydrogen or a group selected from $C_{1-6}$alkyl, a carbocyclyl, a carbocylC$_{1-6}$ alkyl, a heterocyclyl and heterocyclyC$_{1-6}$alkyl group which group is optionally substituted by one or more substituent groups selected from halo, cyano, nitro, hydroxy, oxo, $C_{1-6}$alkyl, $C_{1-6}$alkoxy, haloC$_{1-6}$alkyl, haloC$_{1-6}$alkoxy, hydroxyC$_{1-6}$alkyl, hydroxyC$_{1-6}$alkoxy, $C_{1-6}$alkoxyC$_{1-6}$alkyl, $C_{1-6}$alkoxyC$_{1-6}$alkoxy, amino, $C_{1-6}$alkylamino, bis($C_{1-6}$alkyl)amino, aminoC$_{1-6}$alkyl, ($C_{1-6}$alkyl)aminoC$_{1-6}$alkyl, bis($C_{1-6}$alkyl)aminoC$_{1-6}$ alkyl, cyanoC$_{1-6}$alkyl, $C_{1-6}$alkylsulfonyl, $C_{1-6}$alkylsulfonylamino, $C_{1-6}$alkylsulfonyl($C_{1-6}$alkyl)amino, sulfamoyl, $C_{1-6}$alkylsulfamoyl, bis($C_{1-6}$alkyl)sulfamoyl, $C_{1-6}$alkanoylamino, $C_{1-6}$alkanoyl($C_{1-6}$alkyl)amino, carbamoyl, $C_{1-6}$alkylcarbamoyl and bis($C_{1-6}$ alkyl)carbamoyl; or $R^a$ and $R^b$ together with the nitrogen atom to which they are attached form a 4- to 10-membered heterocyclic ring wherein 1, 2 or 3 ring carbon atoms is optionally replaced with N, O or S and which ring is optionally substituted by one or more substituent groups selected from halo, cyano, nitro, hydroxy, oxo, $C_{1-6}$alkyl, $C_{1-6}$alkoxy, halo$C_{1-6}$alkyl, halo$C_{1-6}$alkoxy, hydroxy$C_{1-6}$ alkyl, hydroxy$C_{1-6}$alkoxy, $C_{1-6}$alkoxy$C_{1-6}$ alkyl,$C_{1-6}$ alkoxy, amino, $C_{1-6}$alklamino, bis($C_{1-6}$ alkyl) amino, amino$C_{1-6}$alkyl, ($C_{1-6}$alkyl)amino$C_{1-6}$ alkyl, bis ($C_{1-6}$ alkyl)amino$C_{1-6}$alkyl, cyano$C_{1-6}$alkyl, $C_{1-6}$alkylsulfonyl, $C_{1-6}$alkylsulfonylamino, $C_{1-6}$alkylsulfonyl ($C_{1-6}$ alkyl)amino, sulfamoyl, $C_{1-6}$alkylsulfamoyl, bis ($C_{1-6}$ alkyl)sulfamoyl, $C_{1-6}$alkanoylamino, $C_{1-6}$alkanoyl($C_{1-6}$ alkyl)amino, carbamoyl, $C_{1-6}$alkylcarbamol and bis $C_{1-6}$alkyl carbamoyl;

with 6-aminouracil, to give a compound of Formula 1

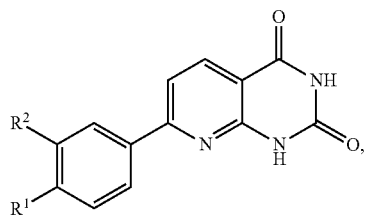

wherein:
$R^2$ is $CH_2OR^4$, CN, $CO_2R^5$ or $CONR^6R^7$; and wherein
  $R^4$ is a —$COR^8$ group, wherein $R^8$ is a secondary $C_{3-6}$alkyl or tertiary $C_{4-6}$alkyl group;

(ii) reacting the compound of Formula 1 with a halogenating agent to give a compound of Formula 4:

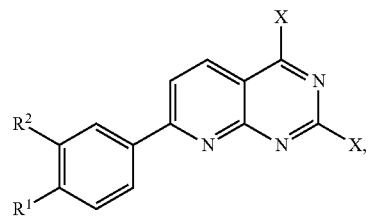

wherein:
$R^2$ is $CH_2OR^4$, CN, $CO_2R^5$ or $CONR^6R^7$, wherein
  $R^4$ is a —$COR^8$ group, and wherein $R^8$ is a secondary $C_{3-6}$alkyl or tertiary $C_{4-6}$alkyl group; and
X is a halogen;
(iii) reacting the compound of Formula 4 with 3-methylmorpholine to give a compound of Formula 5;
(iv) optionally converting the compound of Formula 5 to further compounds of Formula 5 by:
  (a) amidating a compound of Formula 5 wherein $R^2$ is $CO_2R_5$, to give a compound of Formula 5 wherein $R^2$ is $CONR^6R^7$;
  (b) hydrolyzing a compound of Formula 5 wherein $R^2$ is $CH_2OR^4$ and $R^4$ is $COR^8$, to give a compound of Formula 5 wherein $R^2$ is $CH_2OH$; or
  (c) reducing a compound of Formula 5 where $R^2$ is $CO_2R^5$, to a compound of Formula 5 wherein $R^2$ is $CH_2OH$;
(v) and optionally isolating the compound of formula 5 as a salt.

2. The process according to claim 1 wherein the compound of Formula 5 is isolated as a phosphate, sulphate, hydrogensulphate, malate, citrate, tartrate or fumarate salt.

3. The process according to claim 2 wherein the compound of Formula 5 is isolated as a fumarate salt.

* * * * *